(12) United States Patent
Liew et al.

(10) Patent No.: US 7,991,557 B2
(45) Date of Patent: Aug. 2, 2011

(54) COMPUTER SYSTEM AND METHODS FOR CONSTRUCTING BIOLOGICAL CLASSIFIERS AND USES THEREOF

(75) Inventors: Choong-Chin Liew, Toronto (CA); Thomas Yager, Mississauga (CA); Adam Dempsey, Toronto (CA); Samuel Chao, Concord (CA)

(73) Assignee: Genenews Corporation, Ontario (CA)

( * ) Notice: Subject to any disclaimer, the term of this patent is extended or adjusted under 35 U.S.C. 154(b) by 1435 days.

(21) Appl. No.: 10/568,264

(22) PCT Filed: Jun. 20, 2005

(86) PCT No.: PCT/US2005/022071
§ 371 (c)(1),
(2), (4) Date: Feb. 13, 2006

(87) PCT Pub. No.: WO2006/002240
PCT Pub. Date: Jan. 5, 2006

(65) Prior Publication Data
US 2007/0269804 A1    Nov. 22, 2007

Related U.S. Application Data

(60) Provisional application No. 60/663,722, filed on Mar. 22, 2005, provisional application No. 60/643,475, filed on Jan. 12, 2005, provisional application No. 60/581,977, filed on Jun. 21, 2004, provisional application No. 60/581,312, filed on Jun. 19, 2004.

(51) Int. Cl.
*G01N 33/48* (2006.01)

(52) U.S. Cl. ......................................................... 702/19
(58) Field of Classification Search ..................... 702/19
See application file for complete search history.

(56) References Cited

U.S. PATENT DOCUMENTS

| | | |
|---|---|---|
| 2003/0073083 A1 | 4/2003 | Tamayo et al. |
| 2003/0104499 A1 | 6/2003 | Pressman et al. |
| 2004/0110221 A1 | 6/2004 | Twine et al. |

OTHER PUBLICATIONS

International Search Report for PCT Application No. PCT/US05/22071, dated Mar. 16, 2006.
Written Opinion for PCT Application No. PCT/US05/22071, mailed Jul. 18, 2006.

*Primary Examiner* — Jerry Lin
(74) *Attorney, Agent, or Firm* — Jones Day

(57) ABSTRACT

The present invention provides systems and method for constructing classifiers that distinguish between trait subgroups using molecular marker data from blood samples. The invention further encompasses the use of the classifiers and combinations of molecular markers identified by the classifiers in a wide variety of applications including: diagnosis; prognosis; prediction of disease, stage of disease or disease risk; monitoring disease progression and/or regression; monitoring disease reoccurrence and identifying risk of disease reoccurrence; determining and/or predicting response to treatment and/or treatment outcomes; monitoring and/or predicting treatment compliance or non compliance and the like. The invention further provides a variety of selected molecular markers and a means to identify combinations of the selected molecular markers useful for diagnosing particular traits of interest.

18 Claims, 9 Drawing Sheets

| | |
|---|---|
| Model 1 | ⟵ 400-1 |
|   Model name | ⟵ 402-1 |
|   Classifier identity | ⟵ 403-1 |
|   Trait subgroup / trait represented by model | ⟵ 404-1 |
|   Identity of molecular marker 1 | ⟵ 406-1-1 |
|   Molecular marker 1 coefficient | ⟵ 408-1-1 |
|   Identity of molecular marker 2 | ⟵ 406-1-2 |
|   Molecular marker 2 coefficient | ⟵ 408-1-2 |
|   ⋮ | |
|   Identity of molecular marker N | ⟵ 406-1-N |
|   Molecular marker N coefficient | ⟵ 408-1-N |
| Model 2 | ⟵ 400-2 |
| ⋮ | |
| Model N | ⟵ 400-N |

COMPUTER SYSTEM AND METHODS FOR CONSTRUCTING BIOLOGICAL CLASSIFIERS AND USES THEREOF

This application is entitled to and claims priority benefit under 35 U.S.C. Section 119(e) to U.S. provisional application No. 60/581,312, filed Jun. 19, 2004, U.S. provisional application No. 60/581,977, filed Jun. 21, 2004, U.S. provisional application No. 60/643,475, filed Jan. 12, 2005, and U.S. provisional application No. 60/663,722, filed Mar. 22, 2005, each of which is incorporated herein by reference in its entirety.

1. FIELD OF THE INVENTION

The field of this invention relates to computer systems and methods to identify classifiers using data obtained from blood. The invention further encompasses the use of the classifiers and combinations of molecular markers identified by the classifiers in a wide variety of applications including: diagnosis; prognosis; prediction of disease, stage of disease or disease risk; monitoring disease progression and/or regression; monitoring disease reoccurrence and identifying risk of disease reoccurrence; determining and/or predicting response to treatment and/or treatment outcomes; monitoring and/or predicting treatment compliance or non compliance and the like.

Tables 1A-7I, submitted herewith on compact disc, are incorporated herein by reference. The names of each of the files contained on the compact disc along with a description of each of the files, the size of each of the files, and the date of creation of each of the files are recited below.

| Table | DESCRIPTION | SIZE | Date Recorded | Text File Name |
| --- | --- | --- | --- | --- |
| IA | Sequence Related Table regarding Comorbid Hypertension | 96 KB | Jun. 17, 2005 | TABLE1A.TXT |
| IB | Sequence Related Table regarding Comorbid Obesity | 102 KB | Jun. 17, 2005 | TABLE1B.TXT |
| 1C | Sequence Related Table regarding Comorbid Allergies | 49 KB | Jun. 17, 2005 | TABLE1C.TXT |
| ID | Sequence Related Table regarding Comorbid Systemic Steroids | 59 KB | Jun. 17, 2005 | TABLE1O.TXT |
| IE | Sequence Related Table regarding Hypertension (Chondro) | 204 KB | Jun. 17, 2005 | TABLE1E.TXT |
| IF | Sequence Related Table regarding Obesity (Chondro) | 251 KB | Jun. 17, 2005 | TABLE1F.TXT |
| IG | Sequence Related Table regarding CoMorbid Hypertension Only | 57 KB | Jun. 17, 2005 | TABLE1G.TXT |
| IH | Sequence Related Table regarding Hypertension OA Shared | 23 KB | Jun. 17, 2005 | TABLE1H.TXT |
| II | Sequence Related Table regarding Comorbid Obesity Only | 60 KB | Jun. 17, 2005 | TABLE1I.TXT |
| IJ | Sequence Related Table regarding Obesity OA Shared | 18 KB | Jun. 17, 2005 | TABLE1J.TXT |
| IK | Sequence Related Table regarding Comorbid Allergy Only | 28 KB | Jun. 17, 2005 | TABLE1K.TXT |
| IL | Sequence Related Table regarding Allergy OA Shared | 19 KB | Jun. 17, 2005 | TABLE1L.TXT |
| IM | Sequence Related Table regarding Comorbid Steroid Shared | 40 KB | Jun. 17, 2005 | TABLE1M.TXT |
| IN | Sequence Related Table regarding Steroid OA Shared | 23 KB | Jun. 17, 2005 | TABLE1N.TXT |
| 10 | Sequence Related Table regarding Differentiating Systemic Steroids ( | 49 KB | Jun. 17, 2005 | TABLE1O.TXT |
| IP | Sequence Related Table regarding Diabetes | 118 KB | Jun. 17, 2005 | TABLE1P.TXT |
| IQ | Sequence Related Table regarding Hyperlipidemia | 165 KB | Jun. 17, 2005 | TABLE1Q.TXT |
| IR | Sequence Related Table regarding Lung Disease | 102 KB | Jun. 17, 2005 | TABLE1R.TXT |
| IS | Sequence Related Table regarding Bladder Cancer | 830 KB | Jun. 17, 2005 | TABLE1S.TXT |
| IT | Sequence Related Table regarding Bladder Cancer Staging | 483 KB | Jun. 17, 2005 | TABLE1T.TXT |
| IU | Sequence Related Table regarding Coronary Artery Disease | 657 KB | Jun. 17, 2005 | TABLE1U.TXT |
| IV | Sequence Related Table regarding Rheumatoid Arthritis | 380 KB | Jun. 17, 2005 | TABLE1V.TXT |

-continued

| Table | DESCRIPTION | SIZE | Date Recorded | Text File Name |
|---|---|---|---|---|
| IW | Sequence Related Table regarding Rheumatoid Arthritis | 183 KB | Jun. 17, 2005 | TABLE1W.TXT |
| IX | Sequence Related Table regarding Depression | 165 KB | Jun. 17, 2005 | TABLE1X.TXT |
| IY | Sequence Related Table regarding OAStaging | 32 KB | Jun. 17, 2005 | TABLE1Y.TXT |
| IZ | Sequence Related Table regarding Liver Cancer | 19 KB | Jun. 17, 2005 | TABLE1Z.TXT |
| IZb | Seqeuence Related Table regarding Liver Cancer | 430 KB | Jun. 17, 2005 | TABLE1Z.TXT |
| IAA | Sequence Related Table regarding Schizophrenia | 592 KB | Jun. 17, 2005 | TABLE1AA.TXT |
| IAB | Sequence Related Table regarding Chagas Disease | 142 KB | Jun. 17, 2005 | TABLE1AB.TXT |
| IAC | Sequence Related Table regarding Asthma (Chondro) | 64 KB | Jun. 17, 2005 | TABLE1AC.TXT |
| IAD | Sequence Related Table regarding Asthma (Affy) | 57 KB | Jun. 17, 2005 | TABLE1AD.TXT |
| IAE | Sequence Related Table regarding Lung Cancer | 118 KB | Jun. 17, 2005 | TABLE 1AE.TXT |
| IAG | Sequence Related Table regarding Hypertension (Afrymetrix) | 157 KB | Jun. 17, 2005 | TABLE1AG.TXT |
| IAH | Sequence Related Table regarding Obesity (Affymetrix) | 203 KB | Jun. 17, 2005 | TABLE1AH.TXT |
| IAI | Sequence Related Table regarding Ankylosing Spondylitis (Afify) | 267 KB | Jun. 17, 2005 | TABLE1AI.TXT |
| 2 | Sequence Related Table regarding OA Only Subtraction | 19 KB | Jun. 17, 2005 | TABLE2.TXT |
| 3A | Sequence Related Table regarding Schizophrenia v. MDS | 228 KB | Jun. 17, 2005 | TABLE3A.TXT |
| 3B | Sequence Related Table regarding Hepatitis v. Liver Cancer | 347 KB | Jun. 17, 2005 | TABLE3B.TXT |
| 3C | Sequence Related Table regarding Bladder Cancer v. Kidney Cancer | 470 KB | Jun. 17, 2005 | TABLE3C.TXT |
| 3D | Sequence Related Table regarding Bladder Cancer v. Testicular Cancer | 556 KB | Jun. 17, 2005 | TABLE3D.TXT |
| 3E | Sequence Related Table regarding Testicular Cancer v. Kidney Cancer | 588 KB | Jun. 17, 2005 | TABLE3E.TXT |
| 3F | Sequence Related Table regarding Liver Cancer v. Stomach Cancer | 84 KB | Jun. 17, 2005 | TABLE3F.TXT |
| 3G | Sequence Related Table regarding Liver Cancer v. Colon Cancer | 149 KB | Jun. 17, 2005 | TABLE3G.TXT |
| 3H | Sequence Related Table regarding Stomach Cancer v. Colon Cancer | 166 KB | Jun. 17, 2005 | TABLE3H.TXT |
| 31 | Sequence Related Table regarding OA v. RA | 214 KB | Jun. 17, 2005 | TABLE3I.TXT |
| 3K | Sequence Related Table regarding Chagas Disease v. Heart Failure | 16 KB | Jun. 17, 2005 | TABLE3K.TXT |
| 3L | Sequence Related Table regarding Chagas Disease v. CAD | 19 KB | Jun. 17, 2005 | TABLE3L.TXT |
| 3N | Sequence Related Table regarding CAD v. Heart Failure | 13 KB | Jun. 17, 2005 | TABLE3N.TXT |
| 3P | Sequence Related Table regarding Asymptomatic Chagas v. Symptomatic Chagas | 68 KB | Jun. 17, 2005 | TABLE3P.TXT |
| 3Q | Sequence Related Table regarding Alzheimers' v. Schizophrenia | 56 KB | Jun. 17, 2005 | TABLE3Q.TXT |
| 3R | Sequence Related Table regarding Alzheimers' v. Manic Depression | 51 KB | Jun. 17, 2005 | TABLE3R.TXT |

-continued

| Table | DESCRIPTION | SIZE | Date Recorded | Text File Name |
|---|---|---|---|---|
| 4A | Sequence Related Table regarding OA v. Control (ChondroChip) | 538 KB | Jun. 17, 2005 | TABLE4A.TXT |
| 4B | Sequence Related Table regarding OA v. Control (Affy) | 550 KB | Jun. 17, 2005 | TABLE4B.TXT |
| 4C | Sequence Related Table regarding OA mild v. Control (ChondroChip) | 321 KB | Jun. 17, 2005 | TABLE4C.TXT |
| 4D | Sequence Related Table regarding OA mild v. Control (Affy) | 587 KB | Jun. 17, 2005 | TABLE 4D.TXT |
| 4E | Sequence Related Table regarding OA moderate v. Control (ChondroChip) | 198 KB | Jun. 17, 2005 | TABLE4E.TXT |
| 4F | Sequence Related Table regarding OA moderate v. Control (Affy) | 576 KB | Jun. 17, 2005 | TABLE4F.TXT |
| 4G | Sequence Related Table regarding OA marked v. Control (ChondroChip) | 203 KB | Jun. 17, 2005 | TABLE4G.TXT |
| 4H | Sequence Related Table regarding OA marked v. Control (Affy) | 679 KB | Jun. 17, 2005 | TABLE4H.TXT |
| 4I | Sequence Related Table regarding OA severe v. Control (ChondroChip) | 291 KB | Jun. 17, 2005 | TABLE4I.TXT |
| 4J | Sequence Related Table regarding OA severe v. Control (Affy) | 607 KB | Jun. 17, 2005 | TABLE4J.TXT |
| 4K | Sequence Related Table regarding OA mild v. moderate (ChondroChip) | 113 KB | Jun. 17, 2005 | TABLE4K.TXT |
| 4L | Sequence Related Table regarding OA mild v. moderate (Affy) | 488 KB | Jun. 17, 2005 | TABLE4L.TXT |
| 4M | Sequence Related Table regarding OA mild v. marked (ChondroChip) | 93 KB | Jun. 17, 2005 | TABLE4M.TXT |
| 4N | Sequence Related Table regarding OA mild v. marked (Affy) | 373 KB | Jun. 17, 2005 | TABLE4N.TXT |
| 4O | Sequence Related Table regarding OA mild v. severe (ChondroChip) | 177 KB | Jun. 17, 2005 | TABLE4O.TXT |
| 4P | Sequence Related Table regarding OA mild v. severe (Affy) | 687 KB | Jun. 17, 2005 | TABLE4P.TXT |
| 4Q | Sequence Related Table regarding OA moderate v. marked (ChondroChip) | 103 KB | Jun. 17, 2005 | TABLE4Q.TXT |
| 4R | Sequence Related Table regarding OA moderate v. marked (Affy) | 450 KB | Jun. 17, 2005 | TABLE4R.TXT |
| 4S | Sequence Related Table regarding OA moderate v. severe (ChondroChip) | 79 KB | Jun. 17, 2005 | TABLE4S.TXT |
| 4T | Sequence Related Table regarding OA moderate v. severe (Affy) | 627 KB | Jun. 17, 2005 | TABLE4T.TXT |
| 4U | Sequence Related Table regarding OA marked v. severe (ChondroChip) | 66 KB | Jun. 17, 2005 | TABLE4U.TXT |
| 4V | Sequence Related Table regarding OA marked v. severe (Affy) | 758 KB | Jun. 17, 2005 | TABLE4V.TXT |
| 5A | Sequence Related Table regarding Psoriasis v. Control | 80 KB | Jun. 17, 2005 | TABLE5A.TXT |
| 5B | Sequence Related Table regarding Thyroid Disorder v. Control | 373 KB | Jun. 17, 2005 | TABLE5B.TXT |
| 5C | Sequence Related Table regarding Irritable Bowel Syndrome v. Control | 87 KB | Jun. 17, 2005 | TABLE5C.TXT |
| 5D | Sequence Related Table regarding Osteoporosis v. Control | 79 KB | Jun. 17, 2005 | TABLE5D.TXT |

-continued

| Table | DESCRIPTION | SIZE | Date Recorded | Text File Name |
|---|---|---|---|---|
| 5E | Sequence Related Table regarding Migraine Headaches v. Control | 231 KB | Jun. 17, 2005 | TABLE5E.TXT |
| 5F | Sequence Related Table regarding Eczema v. Control | 56 KB | Jun. 17, 2005 | TABLE5F.TXT |
| 5G | Sequence Related Table regarding NASH v. Control | 349 KB | Jun. 17, 2005 | TABLE5G.TXT |
| 5H | Sequence Related Table regarding Alzheimers' v. Control | 268 KB | Jun. 17, 2005 | TABLE5H.TXT |
| 5I | Sequence Related Table regarding Manic Depression v. Control | 298 KB | Jun. 17, 2005 | TABLE5I.TXT |
| 5J | Sequence Related Table regarding Crohns' Colitis v. Control | 45 KB | Jun. 17, 2005 | TABLE5J.TXT |
| 5K | Sequence Related Table regarding Chronic Cholecystis v. Control | 53 KB | Jun. 17, 2005 | TABLE5K.TXT |
| 5L | Sequence Related Table regarding Heart Failure v. Control | 160 KB | Jun. 17, 2005 | TABLE5L.TXT |
| 5M | Sequence Related Table regarding Cervical Cancer v. Control | 304 KB | Jun. 17, 2005 | TABLE5M.TXT |
| 5N | Sequence Related Table regarding Stomach Cancer v. Control | 185 KB | Jun. 17, 2005 | TABLE5N.TXT |
| 5O | Sequence Related Table regarding Kidney Cancer v. Control | 404 KB | Jun. 17, 2005 | TABLE5O.TXT |
| 5P | Sequence Related Table regarding Testicular Cancer v. Control | 486 KB | Jun. 17, 2005 | TABLE5P.TXT |
| 5Q | Sequence Related Table regarding Colon Cancer v. Control | 380 KB | Jun. 17, 2005 | TABLE5Q.TXT |
| 5R | Sequence Related Table regarding Hepatitis B v. Control | 140 KB | Jun. 17, 2005 | TABLE5R.TXT |
| 5S | Sequence Related Table regarding Pancreatic Cancer v. Control | 177 KB | Jun. 17, 2005 | TABLE5S.TXT |
| 5T | Sequence Related Table regarding Asymptomatic Chagas v. Control | 63 KB | Jun. 17, 2005 | TABLE5T.TXT |
| 5U | Sequence Related Table regarding Symptomatic Chagas v. Control | 77 KB | Jun. 17, 2005 | TABLE5U.TXT |
| 5V | Sequence Related Table regarding Bladder Cancer v. Control | 383 KB | Jun. 17, 2005 | TABLE5V.TXT |
| 6A | Sequence Related Table regarding Cancer (all types) v. Control | 163 KB | Jun. 17, 2005 | TABLE6A.TXT |
| 6B | Sequence Related Table regarding Cardiovascular Disease v. Control | 73 KB | Jun. 17, 2005 | TABLE6B.TXT |
| 6c | Sequence Related Table regarding Neurological Diseases v. Control | 337 KB | Jun. 17, 2005 | TABLE6C.TXT |
| 7A | Sequence Related Table regarding Celebrex ® v. all Cox inhibitors except Celebrex | 55 KB | Jun. 17, 2005 | TABLE7A.TXT |
| 7B | Sequence Related Table regarding Celebrex ® v. Control | 57 KB | Jun. 17, 2005 | TABLE7B.TXT |
| 7C | Sequence Related Table regarding Vioxx ® v. Control | 53 KB | Jun. 17, 2005 | TABLE7C.TXT |
| 7D | Sequence Related Table regarding Vioxx ® v. All Cox Inhibitors except Vioxx ® | 49 KB | Jun. 17, 2005 | TABLE7D.TXT |
| 7E | Sequence Related Table regarding NSAIDS v. Control | 72 KB | Jun. 17, 2005 | TABLE7E.TXT |
| 7F | Sequence Related Table regarding Cortisone v. Control | 208 KB | Jun. 17, 2005 | TABLE7F.TXT |

-continued

| Table | DESCRIPTION | SIZE | Date Recorded | Text File Name |
|---|---|---|---|---|
| 7G | Sequence Related Table regarding Visco Supplement v. Control | 316 KB | Jun. 17, 2005 | TABLE7G.TXT |
| 7H | Sequence Related Table regarding Lipitor ® v. Control | 131 KB | Jun. 17, 2005 | TABLE7H.TXT |
| 7I | Sequence Related Table regarding Smoker v. Non-Smoker | 23 KB | Jun. 17, 2005 | TABLE7I.TXT |

LENGTHY TABLES

The patent contains a lengthy table section. A copy of the table is available in electronic form from the USPTO web site (http://seqdata.uspto.gov/?pageRequest=docDetail&DocID=US07991557B2). An electronic copy of the table will also be available from the USPTO upon request and payment of the fee set forth in 37 CFR 1.19(b)(3).

2. BACKGROUND OF THE INVENTION

The prior art is deficient in simple, non-invasive and effective methods of identifying molecular markers and the use of said molecular markers for purposes of: diagnosis; prognosis; prediction of disease, stage of disease or disease risk; monitor disease progression and/or regression; monitor disease reoccurrence and identifying risk of disease reoccurrence or the like. The prior art is also deficient in simple non-invasive methods of identifying molecular markers and use of said molecular markers to determine and/or predict response to treatment and/or treatment outcomes, monitor and/or predict treatment compliance or non-compliance, etc. Although progress has been made in identifying molecular markers by detecting the products of putative molecular markers using expression arrays in a variety of diagnostic areas and therapeutic areas, such progress has been primarily limited to studying non-blood tissue samples, such as primary tumors, that are difficult to obtain and thus have limited potential as a diagnostic. What is even more unsatisfactory is that retrieval of such tissue samples often requires invasive medical procedures such as surgery. Prediction of response to treatment is also a significant problem. It is well understood that, for many currently recognized treatments, only a small percentage of the population (for example approximately 20-30%) will respond positively. Amongst the remainder of the population, there are those who do not improve, and others who display a negative or toxic response to the treatment. As a result of these detrimental effects to some, many effective treatments do not get to market. The prior art is thus deficient in simple, non-invasive methods to analyze and predict treatment and response to treatment.

Such drawbacks have made identification of molecular markers unsatisfactorily difficult. See, for example, Alon et al, 1999, Proc. Natl. Acad. Sci. USA 96, pp. 6745-6750; Schummer et al, 1999, Gene 238, pp. 375-385; and van't Veer, 2002, Nature 415, pp. 530-536.

Even where progress has been made in identifying molecular markers by monitoring molecular marker products using expression arrays—whether in blood or using tissue—the techniques utilized merely identify large number of molecular markers two or more of which may be required so as to permit categorizing an unknown sample for diagnosis. It is not clear, however, which of these molecular markers are most useful to accurately diagnose an unknown sample. In addition, techniques currently available in the art are not sufficiently robust (ie high levels of reproducibility) in accordance with scientific and regulatory standards so as to be used reliably to diagnose a test individual. Thus what is required in the art is a means to select smaller subsets of useful molecular markers which when used in combination permit the accurate and reproducible diagnosis of an unknown sample for a particular trait of interest. Further what is required in the art is a means of translating the molecular marker data from these selected combinations so as to convert these into a diagnosis.

Discussion or citation of a reference herein will not be construed as an admission that such reference is prior art to the present invention.

3. SUMMARY OF THE INVENTION

Thus what is needed in the art is a method to identify useful combinations of molecular markers and a means of using said combinations of molecular markers (or more accurately measurement of the products of said molecular markers) so as to permit diagnosis of a test sample. Embodiments of the present invention address many of the shortcomings and drawbacks found in the prior art by the novel approach of using molecular marker measurement data from blood and methods of processing such data to screen the large numbers of candidate molecular markers in blood so as to identify useful combinations of these molecular markers. Embodiments of the present invention involve the construction of classifiers and use of these classifiers. In addition, embodiments of the invention involve the use of the molecular markers identified by these classifiers to diagnose or otherwise determine whether a test subject has a specific trait of interest. Blood offers a surprisingly informative alternative to tissues as a source of information. Blood includes numerous cell types including monocytes, leukocytes, lymphocytes, erythrocytes, platelets, as well as possibly many other cell types. The turnover of cells in the human circulatory system is rapid. As a consequence of continuous interactions between the blood and the body, it has been hypothesized that the changes that occur within the cells or tissues of the body will trigger specific changes in gene expression within blood. See, for example, U.S. patent application Ser. No. 10/601,518, filed Jun. 20, 2003, U.S. patent application Ser. No. 10/802,875, filed Mar. 12, 2004, U.S. patent application Ser. No. 10/809,675, filed Mar. 25, 2004, U.S. patent application Ser. No. 10/268,730, filed Oct. 9, 2002, U.S. patent application Ser. No. 09/477,148, filed Jan. 4, 2000, and U.S. patent application Ser. No. 60/115,125, filed Jan. 6, 1999, which are hereby incorporated herein by reference in their entirety. Thus, blood has the potential to provide a powerful indicator of what is happening in the human body at any given time, but provides unique challenges to harness this vast amount of potential information available. Embodiments of the current invention help address this challenge.

4. BRIEF DESCRIPTION OF THE DRAWINGS

FIG. 5 illustrates a data structure for storing a plurality of classifiers in accordance with one embodiment of the present invention.

DESCRIPTION OF TABLES

Figure 1:
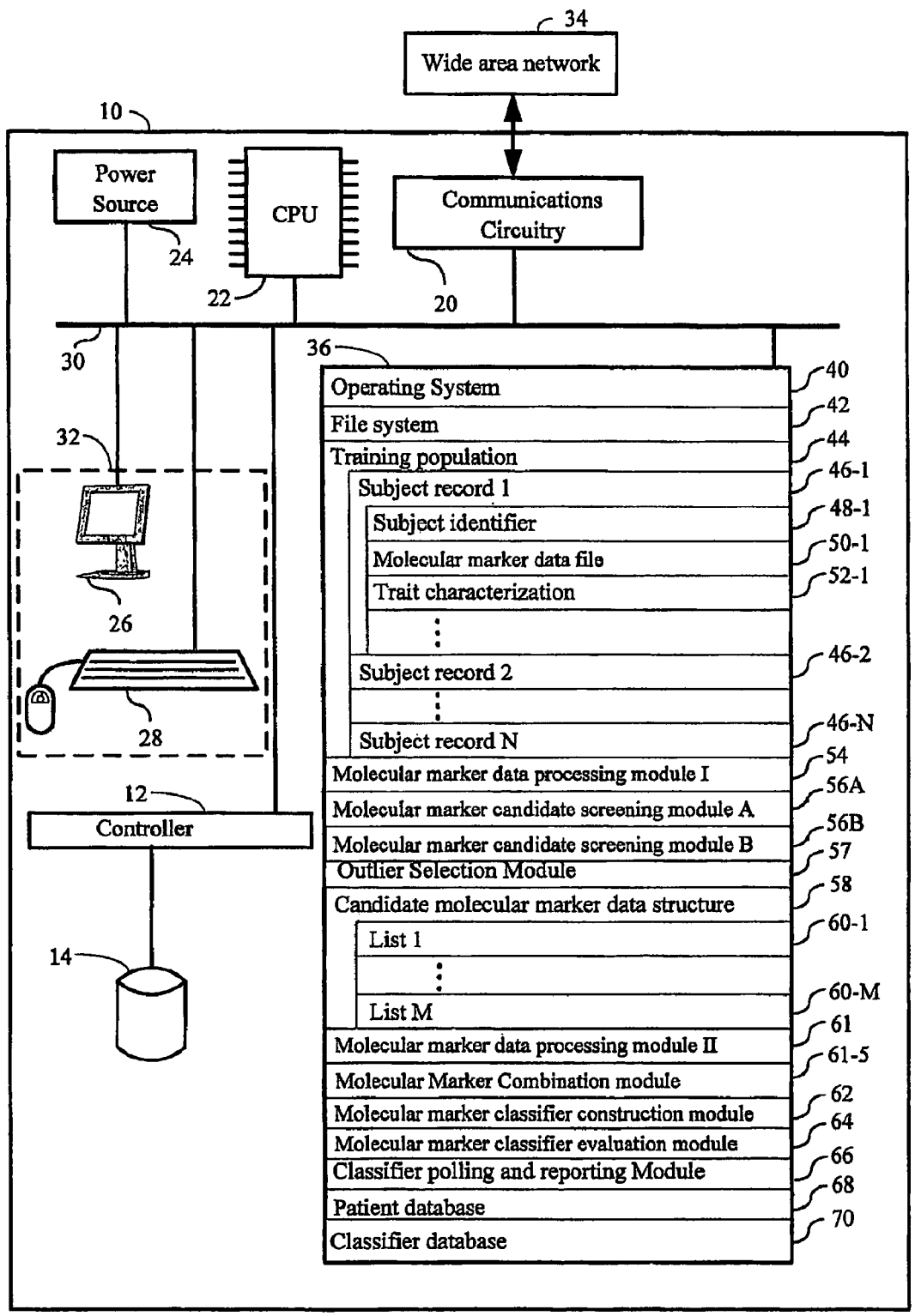
FIG. 1 illustrates a computer system for determining and selecting useful biological classifiers.

Table 1 as a group of tables identifies the molecular markers that are differentially expressed in blood samples from patients with a disease or patients who are co-morbid as compared to blood samples from healthy patients or patients without said disease, or with only one of said co-morbid diseases and also shows the sequences of selected products of the identified molecular markers. Molecular marker data from the molecular markers listed in each table or a subset of these molecular markers can be used can be used in steps 214-218 as outlined in FIG. 2B so as to identify classifiers and the combinations of molecular markers which form the classifiers useful in diagnosis.

Table IA identifies the molecular markers which are differentially expressed in blood samples from a training population comprised of a first trait subgroup where each member of the subgroup has both osteoarthritis and hypertension as compared with a second trait subgroup wherein each member of the second trait subgroup has neither osteoarthritis nor hypertension using the ChondroChip™ platform. The table also shows the sequences of selected products of the identified molecular markers.

Table IB shows the identity of those molecular markers that are differentially expressed in blood samples from a training population comprised of a first trait subgroup where each member of the subgroup has both osteoarthritis and obesity as compared with a second trait subgroup wherein each member of the second trait subgroup has neither osteoarthritis nor obesity using the ChondroChip™ platform. The table also shows the sequences of selected products of the identified molecular markers.

Table 1C shows the molecular markers that are differentially expressed in blood samples from a training population comprised of a first trait subgroup where each member of the subgroup has both osteoarthritis and allergies as compared with a second trait subgroup wherein each member of the second trait subgroup has neither osteoarthritis nor allergies using the ChondroChip™ platform. The table also shows the sequences of selected products of the identified molecular markers.

Table ID shows the molecular markers that are differentially expressed in blood samples from a training population comprised of a first trait subgroup where each member of the subgroup has both osteoarthritis and subject to systemic steroids as compared with normal patients using the ChondroChip™ platform. The table also shows the sequences of selected products of the identified molecular markers.

Table IE shows the molecular markers that are differentially expressed in blood samples from a training population comprised of a first trait subgroup where each member of the subgroup has hypertension as compared to a second trait subgroup wherein each member of the second trait subgroup did not have hypertension using the ChondroChip™ platform. The table also shows the sequences of selected products of the identified molecular markers.

Table IF shows the molecular markers that are differentially expressed in blood samples from a training population comprised of a first trait subgroup where each member of the subgroup has obesity as compared to a second trait subgroup wherein each member of the second trait subgroup did not have obesity using the ChondroChip™ platform. The table also shows the sequences of selected products of the identified molecular markers.

Table IG shows the molecular markers that are differentially expressed in blood samples from a training population comprised of a first trait subgroup where each member of the subgroup has hypertension and OA when compared with a second trait subgroup wherein each member of the second trait subgroup have OA only wherein molecular markers identified in Table IA have been removed so as to identify molecular markers which are unique to hypertension. The table also shows the sequences of selected products of the identified molecular markers.

Table IH shows the molecular markers which were identified in Table IA which are shared with those molecular markers differentially expressed in blood samples from a training population comprised of a first trait subgroup where each member of the subgroup has both hypertension and OA when compared with a second trait subgroup wherein each member of the second trait subgroup have OA only. The table also shows the sequences of selected products of the identified molecular markers.

Table II shows the molecular markers that are differentially expressed in blood samples from a training population comprised of a first trait subgroup where each member of the subgroup has both obesity and have OA when compared with a second trait subgroup wherein each member of the second trait subgroup have OA only and wherein molecular markers identified in Table IB have been removed so as to identify molecular markers which are unique to obesity. The table also shows the sequences of selected products of the identified molecular markers.

Table IJ shows the molecular markers identified in Table IB which are shared with those molecular markers differentially expressed in blood samples from patients who are obese and have OA when compared with patients who have OA. The table also shows the sequences of selected products of the identified molecular markers.

Table IK shows the molecular markers that are differentially expressed in blood samples from a training population comprised of a first trait subgroup where each member of the subgroup has both allergies and OA when compared with a second trait subgroup wherein each member of the second trait subgroup have OA only wherein molecular markers identified in Table IC have been removed so as to identify molecular markers which are unique to allergies. The table also shows the sequences of selected products of the identified molecular markers.

Table IL shows the identify of those molecular markers identified in Table 3C which are shared with those molecular markers differentially expressed in blood samples from a training population comprised of a first trait subgroup where each member of the subgroup has both allergies and OA when compared with a second trait subgroup wherein each member of the second trait subgroup having OA only. The table also shows the sequences of selected products of the identified molecular markers.

Table IM shows the molecular markers that are differentially expressed in blood samples from a training population comprised of a first trait subgroup where each member of the subgroup is taking systemic steroids and has OA when compared with a second trait subgroup wherein each member of the second trait subgroup have OA only wherein molecular markers identified in Table ID have been removed so as to identify molecular markers which are unique to patients on systemic steroids. The table also shows the sequences of selected products of the identified molecular markers.

Table IN shows the identify of those molecular markers identified in Table ID which are shared with those molecular markers differentially expressed in blood samples from a training population comprised of a first trait subgroup where each member of the subgroup who are on systemic steroids and have OA when compared with a second trait subgroup wherein each member of the second trait subgroup have OA only. The table also shows the sequences of selected products of the identified molecular markers.

Table IO shows the molecular markers that are differentially expressed in blood from a training population comprised of a first trait subgroup where each member of the subgroup are either taking birth control, on prednisone or on hormone replacement therapy and presenting with OA using the ChondroChip™ platform. The table also shows the sequences of selected products of the identified molecular markers.

Table IP shows the molecular markers that are differentially expressed in blood samples from a training population comprised of a first trait subgroup where each member of the subgroup has both type II diabetes as compared to a second trait subgroup wherein each member of the second trait subgroup does not have type II diabetes using the ChondroChip™ platform. The table also shows the sequences of selected products of the identified molecular markers.

Table IQ shows the molecular markers that are differentially expressed in blood samples from a training population comprised of a first trait subgroup where each member of the subgroup has Hyperlipidemia as compared to a second trait subgroup wherein each member of the second trait subgroup does not have Hyperlipidemia using the ChondroChip™ platform. The table also shows the sequences of selected products of the identified molecular markers.

Table IR shows the molecular markers that are differentially expressed in blood samples from a training population comprised of a first trait subgroup where each member of the subgroup has lung disease as compared to a second trait subgroup wherein each member of the second trait subgroup does not have lung disease using the ChondroChip™ platform. The table also shows the sequences of selected products of the identified molecular markers.

Table IS shows the molecular markers that are differentially expressed in blood samples from a training population comprised of a first trait subgroup where each member of the subgroup has bladder cancer as compared to a second trait subgroup wherein each member of the second trait subgroup does not have bladder cancer using the ChondroChip™ platform. The table also shows the sequences of selected products of the identified molecular markers.

Table IT shows the molecular markers that are differentially expressed in blood samples from a training population comprised of a first trait subgroup where each member of the subgroup has early stage bladder cancer, late stage bladder cancer with a second trait subgroup wherein each member of the second trait subgroup does not have bladder cancer using the ChondroChip™ platform. The table also shows the sequences of selected products of the identified molecular markers.

Table IU shows the molecular markers that are differentially expressed in blood samples from a training population comprised of a first trait subgroup where each member of the subgroup has coronary artery disease (CAD) as compared to a second trait subgroup wherein each member of the second trait subgroup does not have not having CAD using the ChondroChip™ platform. The table also shows the sequences of selected products of the identified molecular markers.

Table IV shows the molecular markers that are differentially expressed in blood samples from a training population comprised of a first trait subgroup where each member of the subgroup has rheumatoid arthritis as compared to a second trait subgroup wherein each member of the second trait subgroup does not have rheumatoid arthritis using the ChondroChip™ platform. The table also shows the sequences of selected products of the identified molecular markers.

Table IW shows the molecular markers that are differentially expressed in blood samples from a training population comprised of a first trait subgroup where each member of the subgroup has rheumatoid arthritis as compared to a second trait subgroup wherein each member of the second trait subgroup does not have rheumatoid arthritis using the Affymetrix® platform. The table also shows the sequences of selected products of the identified molecular markers.

Table IX shows the molecular markers that are differentially expressed in blood samples from a training population comprised of a first trait subgroup where each member of the subgroup has depression as compared with a second trait subgroup wherein each member of the second trait subgroup does not having depression using the ChondroChip™ platform. The table also shows the sequences of selected products of the identified molecular markers.

Table IY shows the molecular markers that are differentially expressed in blood samples from a training population comprised of a first trait subgroup where each member of the subgroup has one of various stages of osteoarthritis as compared with a second trait subgroup wherein each member of the second trait subgroup does not have osteoarthritis using the ChondroChip™ platform. The table also shows the sequences of selected products of the identified molecular markers.

Table IZ shows the molecular markers that are differentially expressed in blood samples from a training population comprised of a first trait subgroup where each member of the subgroup has liver cancer as compared with a second trait subgroup wherein each member of the second trait subgroup does not have liver cancer using the ChondroChip™ platform. The table also shows the sequences of selected products of the identified molecular markers.

Table IZ(B) shows the molecular markers that are differentially expressed in blood samples from a training population comprised of a first trait subgroup where each member of the subgroup has liver cancer as compared with a second trait subgroup wherein each member of the second trait subgroup does not have liver cancer using the Affymetrix® platform. The table also shows the sequences of selected products of the identified molecular markers.

Table IAA shows the molecular markers that are differentially expressed in blood samples from a training population comprised of a first trait subgroup where each member of the subgroup has schizophrenia as compared with a second trait subgroup wherein each member of the second trait subgroup does not have schizophrenia using the Affymetrix® platform. The table also shows the sequences of selected products of the identified molecular markers.

Table IAB shows the molecular markers that are differentially expressed in blood samples from a training population comprised of a first trait subgroup where each member of the subgroup has Chagas disease as compared with a second trait subgroup wherein each member of the second trait subgroup does not have Chagas disease using the Affymetrix® platform. The table also shows the sequences of selected products of the identified molecular markers.

Table IAC shows the molecular markers that are differentially expressed in blood samples from a training population comprised of a first trait subgroup where each member of the subgroup has both asthma and osteoarthritis as compared a second trait subgroup wherein each member of the second trait subgroup has only osteoarthritis using the ChondroChip™. The table also shows the sequences of selected products of the identified molecular markers.

Table IAD shows the molecular markers that are differentially expressed in blood samples from a training population comprised of a first trait subgroup where each member of the subgroup has asthma as compared with a second trait subgroup wherein each member of the second trait subgroup does not have asthma using the Affymetrix® platform. The table also shows the sequences of selected products of the identified molecular markers.

Table IAE shows the molecular markers that are differentially expressed in blood samples from a training population comprised of a first trait subgroup where each member of the subgroup has lung cancer as compared with a second trait subgroup wherein each member of the second trait subgroup does not have lung cancer using the Affymetrix® platform. The table also shows the sequences of selected products of the identified molecular markers.

Table IAG shows the molecular markers that are differentially expressed in blood samples from a training population comprised of a first trait subgroup where each member of the subgroup has hypertension as compared with a second trait subgroup wherein each member of the second trait subgroup does not have hypertension using the Affymetrix® platform. The table also shows the sequences of selected products of the identified molecular markers.

Table IAH shows the molecular markers that are differentially expressed in blood samples from a training population comprised of a first trait subgroup where each member of the subgroup has obesity as compared with a second trait subgroup wherein each member of the second trait subgroup does not have obesity using the Affymetrix® platform. The table also shows the sequences of selected products of the identified molecular markers.

Table IAI shows the molecular markers that are differentially expressed in blood samples from a training population comprised of a first trait subgroup where each member of the subgroup has ankylosing spondylitis as compared with a second trait subgroup wherein each member of the second trait subgroup does not have ankylosing spondylitis using the Affymetrix® platform. The table also shows the sequences of selected products of the identified molecular markers.

Table 2 shows the molecular markers that are differentially expressed in blood from a training population comprised of a first trait subgroup where each member of the subgroup has either mild or severe OA, but for which molecular markers relevant to asthma, obesity, hypertension, systemic steroids and allergies have been removed. The table also shows the sequences of selected products of the identified molecular markers.

Table 3 is a group of tables wherein each table shows those molecular markers that are differentially expressed in blood samples from a training population comprised of a first trait subgroup where each member of the subgroup has a first disease as compared to blood samples from a second trait subgroup wherein each member of the second trait subgroup has a second disease so as to allow differential diagnosis as between said first and second disease.

Table 3A shows the molecular markers that are differentially expressed in blood from a training population comprised of a first trait subgroup where each member of the subgroup has schizophrenia as compared with a second trait subgroup wherein each member of the second trait subgroup has manic depression syndrome (MDS) using the Affymetrix® platform. The table also shows the sequences of selected products of the identified molecular markers.

Table 3B shows the molecular markers that are differentially expressed in blood from a training population comprised of a first trait subgroup where each member of the subgroup has hepatitis as compared with a second trait subgroup wherein each member of the second trait subgroup has liver cancer using the Affymetrix® platform. The table also shows the sequences of selected products of the identified molecular markers.

Table 3C shows the molecular markers that are differentially expressed in blood from a training population comprised of a first trait subgroup where each member of the subgroup has bladder cancer as compared with a second trait subgroup wherein each member of the second trait subgroup has liver cancer using the Affymetrix® platform. The table also shows the sequences of selected products of the identified molecular markers.

Table 3D shows the molecular markers that are differentially expressed in blood from a training population comprised of a first trait subgroup where each member of the subgroup has bladder cancer as compared with a second trait subgroup wherein each member of the second trait subgroup has testicular cancer using the Affymetrix® platform. The table also shows the sequences of selected products of the identified molecular markers.

Table 3E shows the molecular markers that are differentially expressed in blood from a training population comprised of a first trait subgroup where each member of the subgroup has testicular cancer as compared with a second trait subgroup wherein each member of the second trait subgroup has kidney cancer using the Affymetrix® platform. The table also shows the sequences of selected products of the identified molecular markers.

Table 3F shows the molecular markers that are differentially expressed in blood from a training population comprised of a first trait subgroup where each member of the subgroup has liver cancer as compared with a second trait subgroup wherein each member of the second trait subgroup has stomach cancer using the Affymetrix® platform. The table also shows the sequences of selected products of the identified molecular markers.

Table 3 G shows the molecular markers that are differentially expressed in blood from a training population comprised of a first trait subgroup where each member of the subgroup has liver cancer as compared with a second trait subgroup wherein each member of the second trait subgroup has colon cancer using the Affymetrix® platform. The table also shows the sequences of selected products of the identified molecular markers.

Table 3H shows the molecular markers that are differentially expressed in blood from a training population comprised of a first trait subgroup where each member of the subgroup has stomach cancer as compared with a second trait subgroup wherein each member of the second trait subgroup has colon cancer using the Affymetrix® platform. The table also shows the sequences of selected products of the identified molecular markers.

Table 3I shows the molecular markers that are differentially expressed in blood from a training population comprised of a first trait subgroup where each member of the subgroup has Rheumatoid Arthritis as compared with a second trait subgroup wherein each member of the second trait subgroup has Osteoarthritis using the Affymetrix® platform. The table also shows the sequences of selected products of the identified molecular markers.

Table 3K shows the molecular markers that are differentially expressed in blood from a training population comprised of a first trait subgroup where each member of the subgroup has Chagas Disease as compared with a second trait subgroup wherein each member of the second trait subgroup has Heart Failure using the Affymetrix® platform. The table also shows the sequences of selected products of the identified molecular markers.

Table 3L shows the molecular markers that are differentially expressed in blood from a training population comprised of a first trait subgroup where each member of the subgroup has Chagas Disease as compared with a second trait subgroup wherein each member of the second trait subgroup has Coronary Artery Disease using the Affymetrix® platform. The table also shows the sequences of selected products of the identified molecular markers.

Table 3N shows the molecular markers that are differentially expressed in blood from a training population comprised of a first trait subgroup where each member of the subgroup has Coronary Artery Disease as compared with a second trait subgroup wherein each member of the second trait subgroup has Heart Failure using the Affymetrix® platform. The table also shows the sequences of selected products of the identified molecular markers.

Table 3P shows the molecular markers that are differentially expressed in blood from a training population comprised of a first trait subgroup where each member of the subgroup has Asymptomatic Chagas Disease as compared with a second trait subgroup wherein each member of the second trait subgroup has Symptomatic Chagas Disease using the Affymetrix® platform. The table also shows the sequences of selected products of the identified molecular markers.

Table 3Q shows the molecular markers that are differentially expressed in blood from a training population comprised of a first trait subgroup where each member of the subgroup has Alzheimer's as compared with a second trait subgroup wherein each member of the second trait subgroup has Schizophrenia using the Affymetrix® platform. The table also shows the sequences of selected products of the identified molecular markers.

Table 3R shows the molecular markers that are differentially expressed in blood from a training population comprised of a first trait subgroup where each member of the subgroup has Alzheimer's as compared with a second trait subgroup wherein each member of the second trait subgroup has Manic Depression Syndrome using the Affymetrix® platform. The table also shows the sequences of selected products of the identified molecular markers.

Table 4 tables are those which shows molecular markers that are differentially expressed in blood samples from a training population comprised of a first trait subgroup where each member of the subgroup has a stage of Osteoarthritis as compared to blood samples from a second trait subgroup wherein each member of the second trait subgroup has a second stage of Osteoarthritis so as to allow monitoring of progression and/or regression of disease. Each table also shows the sequences of selected products of the identified molecular markers.

Table 4A shows the molecular markers that are differentially expressed in blood from a training population comprised of a first trait subgroup where each member of the subgroup has Osteoarthritis as compared with a second trait subgroup wherein each member of the second trait subgroup is without Osteoarthritis using the ChondroChip™ platform. The table also shows the sequences of selected products of the identified molecular markers.

Table 4B shows the molecular markers that are differentially expressed in blood from a training population comprised of a first trait subgroup where each member of the subgroup has Osteoarthritis as compared with a second trait subgroup wherein each member of the second trait subgroup is without Osteoarthritis using the Affymetrix® platform. The table also shows the sequences of selected products of the identified molecular markers.

Table 4C shows the molecular markers that are differentially expressed in blood from a training population comprised of a first trait subgroup where each member of the subgroup has mild Osteoarthritis as compared with a second trait subgroup wherein each member of the second trait subgroup is without mild Osteoarthritis using the ChondroChip™ platform. The table also shows the sequences of selected products of the identified molecular markers.

Table 4D shows the molecular markers that are differentially expressed in blood from a training population comprised of a first trait subgroup where each member of the subgroup has mild Osteoarthritis as compared with a second trait subgroup wherein each member of the second trait subgroup is without Osteoarthritis using the Affymetrix® platform. The table also shows the sequences of selected products of the identified molecular markers.

Table 4E shows the molecular markers that are differentially expressed in blood from a training population comprised of a first trait subgroup where each member of the subgroup has moderate Osteoarthritis as compared with patients without Osteoarthritis using the ChondroChip™ platform. The table also shows the sequences of selected products of the identified molecular markers.

Table 4F shows the molecular markers that are differentially expressed in blood from a training population comprised of a first trait subgroup where each member of the subgroup has moderate Osteoarthritis as compared a second trait subgroup wherein each member of the second trait subgroup is without Osteoarthritis using the Affymetrix® platform. The table also shows the sequences of selected products of the identified molecular markers.

Table 4G shows the molecular markers that are differentially expressed in blood from a training population comprised of a first trait subgroup where each member of the subgroup has marked Osteoarthritis as compared with a second trait subgroup wherein each member of the second trait subgroup is without Osteoarthritis using the ChondroChip™ platform. The table also shows the sequences of selected products of the identified molecular markers.

Table 4H shows the molecular markers that are differentially expressed in blood from a training population comprised of a first trait subgroup where each member of the subgroup has marked Osteoarthritis as compared with a second trait subgroup wherein each member of the second trait subgroup is without Osteoarthritis using the Affymetrix® platform. The table also shows the sequences of selected products of the identified molecular markers.

Table 4I shows the molecular markers that are differentially expressed in blood from a training population comprised of a first trait subgroup where each member of the subgroup has severe Osteoarthritis as compared with a second trait subgroup wherein each member of the second trait subgroup is without Osteoarthritis using the ChondroChip™ platform. The table also shows the sequences of selected products of the identified molecular markers.

Table 4J shows the molecular markers that are differentially expressed in blood from a training population comprised of a first trait subgroup where each member of the subgroup has severe Osteoarthritis as compared with a second trait subgroup wherein each member of the second trait subgroup is without Osteoarthritis using the Affymetrix® platform. The table also shows the sequences of selected products of the identified molecular markers.

Table 4K shows the molecular markers that are differentially expressed in blood from a training population comprised of a first trait subgroup where each member of the subgroup has mild Osteoarthritis as compared with a second trait subgroup wherein each member of the second trait subgroup has moderate Osteoarthritis using the ChondroChip™ platform. The table also shows the sequences of selected products of the identified molecular markers.

Table 4L shows the molecular markers that are differentially expressed in blood from a training population comprised of a first trait subgroup where each member of the subgroup has mild Osteoarthritis as compared with a second trait subgroup wherein each member of the second trait subgroup has moderate Osteoarthritis using the Affymetrix® platform. The table also shows the sequences of selected products of the identified molecular markers.

Table 4M shows the molecular markers that are differentially expressed in blood from a training population comprised of a first trait subgroup where each member of the subgroup has mild Osteoarthritis as compared with a second trait subgroup wherein each member of the second trait subgroup has marked Osteoarthritis using the ChondroChip™ platform. The table also shows the sequences of selected products of the identified molecular markers.

Table 4N shows the molecular markers that are differentially expressed in blood from a training population comprised of a first trait subgroup where each member of the subgroup has mild Osteoarthritis as compared with a second trait subgroup wherein each member of the second trait subgroup has marked Osteoarthritis using the Affymetrix® platform. The table also shows the sequences of selected products of the identified molecular markers.

Table 4O shows the molecular markers that are differentially expressed in blood from a training population comprised of a first trait subgroup where each member of the subgroup has mild Osteoarthritis as compared with a second trait subgroup wherein each member of the second trait subgroup has severe Osteoarthritis using the ChondroChip™ platform. The table also shows the sequences of selected products of the identified molecular markers.

Table 4P shows the molecular markers that are differentially expressed in blood from a training population comprised of a first trait subgroup where each member of the subgroup has mild Osteoarthritis as compared with a second trait subgroup wherein each member of the second trait subgroup has severe Osteoarthritis using the Affymetrix® platform. The table also shows the sequences of selected products of the identified molecular markers.

Table 4Q shows the molecular markers that are differentially expressed in blood from a training population comprised of a first trait subgroup where each member of the subgroup has moderate Osteoarthritis as compared with a second trait subgroup wherein each member of the second trait subgroup has marked Osteoarthritis using the ChondroChip™ platform. The table also shows the sequences of selected products of the identified molecular markers.

Table 4R shows the molecular markers that are differentially expressed in blood from a training population comprised of a first trait subgroup where each member of the subgroup has moderate Osteoarthritis as compared with a second trait subgroup wherein each member of the second trait subgroup has marked Osteoarthritis using the Affymetrix® platform. The table also shows the sequences of selected products of the identified molecular markers.

Table 4S shows the molecular markers that are differentially expressed in blood from a training population comprised of a first trait subgroup where each member of the subgroup has moderate Osteoarthritis as compared with patients a second trait subgroup wherein each member of the second trait subgroup has severe Osteoarthritis using the ChondroChip™ platform. The table also shows the sequences of selected products of the identified molecular markers.

Table 4T shows the molecular markers that are differentially expressed in blood from a training population comprised of a first trait subgroup where each member of the subgroup has moderate Osteoarthritis as compared with a second trait subgroup wherein each member of the second trait subgroup has severe Osteoarthritis using the Affymetrix® platform. The table also shows the sequences of selected products of the identified molecular markers.

Table 4U shows the molecular markers that are differentially expressed in blood from a training population comprised of a first trait subgroup where each member of the subgroup has marked Osteoarthritis as compared with a second trait subgroup wherein each member of the second trait subgroup has severe Osteoarthritis using the ChondroChip™ platform. The table also shows the sequences of selected products of the identified molecular markers.

Table 4V shows the molecular markers that are differentially expressed in blood from a training population comprised of a first trait subgroup where each member of the subgroup has marked Osteoarthritis as compared with a second trait subgroup wherein each member of the second trait subgroup has severe Osteoarthritis using the Affymetrix® platform. The table also shows the sequences of selected products of the identified molecular markers.

Table 5 tables are those which identify molecular markers that are differentially expressed in blood samples from a training population comprised of a first trait subgroup where each member of the subgroup has a disease or condition of interest as compared to blood samples from a second trait subgroup wherein each member of the second trait subgroup is without said disease or condition. The tables also shows the sequences of selected products of the identified molecular markers.

Table 5A shows the molecular markers that are differentially expressed in blood samples from a training population comprised of a first trait subgroup where each member of the subgroup has psoriasis as compared with a second trait subgroup wherein each member of the second trait subgroup does not have psoriasis using the Affymetrix® platform. The table also shows the sequences of selected products of the identified molecular markers.

Table 5B shows the molecular markers that are differentially expressed in blood samples from a training population comprised of a first trait subgroup where each member of the subgroup has thyroid disorder as compared with a second trait subgroup wherein each member of the second trait subgroup does not have thyroid disorder using the Affymetrix® platform. The table also shows the sequences of selected products of the identified molecular markers.

Table 5C shows the molecular markers that are differentially expressed in blood samples from a training population comprised of a first trait subgroup where each member of the subgroup has irritable bowel syndrome as compared with a second trait subgroup wherein each member of the second trait subgroup does not have irritable bowel syndrome using the Affymetrix® platform. The table also shows the sequences of selected products of the identified molecular markers.

Table 5D shows the molecular markers that are differentially expressed in blood samples from a training population comprised of a first trait subgroup where each member of the subgroup has osteoporosis as compared with a second trait subgroup wherein each member of the second trait subgroup does not have osteoporosis using the Affymetrix® platform. The table also shows the sequences of selected products of the identified molecular markers.

Table 5E shows the molecular markers that are differentially expressed in blood samples from a training population comprised of a first trait subgroup where each member of the subgroup has migraine headaches as compared with a second trait subgroup wherein each member of the second trait subgroup does not have migraine headaches using the Affymetrix® platform. The table also shows the sequences of selected products of the identified molecular markers.

Table 5F shows the molecular markers that are differentially expressed in blood samples from a training population comprised of a first trait subgroup where each member of the subgroup has eczema as compared with a second trait subgroup wherein each member of the second trait subgroup does not have eczema using the Affymetrix® platform. The table also shows the sequences of selected products of the identified molecular markers.

Table 5G shows the molecular markers that are differentially expressed in blood samples from a training population comprised of a first trait subgroup where each member of the subgroup has NASH as compared with a second trait subgroup wherein each member of the second trait subgroup does not have NASH using the Affymetrix® platform. The table also shows the sequences of selected products of the identified molecular markers.

Table 5H shows the molecular markers that are differentially expressed in blood samples from a training population comprised of a first trait subgroup where each member of the subgroup has Alzheimers' disease as compared with a second trait subgroup wherein each member of the second trait subgroup does not have Alzheimer's disease using the Affymetrix® platform. The table also shows the sequences of selected products of the identified molecular markers.

Table 5I shows the molecular markers that are differentially expressed in blood samples from a training population comprised of a first trait subgroup where each member of the subgroup has Manic Depression Syndrome as compared with a second trait subgroup wherein each member of the second trait subgroup does not have Manic Depression Syndrome using the Affymetrix® platform. The table also shows the sequences of selected products of the identified molecular markers.

Table 5J shows the molecular markers that are differentially expressed in blood samples from a training population comprised of a first trait subgroup where each member of the subgroup has Crohn's Colitis as compared with a second trait subgroup wherein each member of the second trait subgroup does not have Crohn's Colitis using the Affymetrix® platform. The table also shows the sequences of selected products of the identified molecular markers.

Table 5K shows the molecular markers that are differentially expressed in blood samples from a training population comprised of a first trait subgroup where each member of the subgroup has Chronic Cholecystis as compared with a second trait subgroup wherein each member of the second trait subgroup does not have Chronic Cholecystis using the Affymetrix® platform. The table also shows the sequences of selected products of the identified molecular markers.

Table 5L shows the molecular markers that are differentially expressed in blood samples from a training population comprised of a first trait subgroup where each member of the subgroup has Heart Failure as compared with a second trait subgroup wherein each member of the second trait subgroup does not have Heart Failure using the Affymetrix® platform. The table also shows the sequences of selected products of the identified molecular markers.

Table 5M shows the molecular markers that are differentially expressed in blood samples from a training population comprised of a first trait subgroup where each member of the subgroup has Cervical Cancer as compared with a second trait subgroup wherein each member of the second trait subgroup does not have Cervical Cancer using the Affymetrix® platform. The table also shows the sequences of selected products of the identified molecular markers.

Table 5N shows the molecular markers that are differentially expressed in blood samples from a training population comprised of a first trait subgroup where each member of the subgroup has Stomach Cancer as compared with a second trait subgroup wherein each member of the second trait subgroup does not have Stomach Cancer using the Affymetrix® platform. The table also shows the sequences of selected products of the identified molecular markers.

Table 5O shows the molecular markers that are differentially expressed in blood samples from a training population comprised of a first trait subgroup where each member of the subgroup has Kidney Cancer as compared with a second trait subgroup wherein each member of the second trait subgroup does not have Kidney Cancer using the Affymetrix® platform. The table also shows the sequences of selected products of the identified molecular markers.

Table 5P shows the molecular markers that are differentially expressed in blood samples from a training population comprised of a first trait subgroup where each member of the subgroup has Testicular Cancer as compared with a second trait subgroup wherein each member of the second trait subgroup does not have Testicular Cancer using the Affymetrix® platform. The table also shows the sequences of selected products of the identified molecular markers.

Table 5Q shows the molecular markers that are differentially expressed in blood samples from a training population comprised of a first trait subgroup where each member of the subgroup has Colon Cancer as compared a second trait subgroup wherein each member of the second trait subgroup does not have Colon Cancer using the Affymetrix® platform. The table also shows the sequences of selected products of the identified molecular markers.

Table 5R shows the molecular markers that are differentially expressed in blood samples from a training population comprised of a first trait subgroup where each member of the subgroup has Hepatitis B as compared with a second trait subgroup wherein each member of the second trait subgroup does not have Hepatitis B using the Affymetrix® platform. The table also shows the sequences of selected products of the identified molecular markers.

Table 5S shows the molecular markers that are differentially expressed in blood samples from a training population comprised of a first trait subgroup where each member of the subgroup has Pancreatic Cancer as compared with a second trait subgroup wherein each member of the second trait subgroup does not have Pancreatic Cancer using the Affymetrix® platform. The table also shows the sequences of selected products of the identified molecular markers.

Table 5T shows the molecular markers that are differentially expressed in blood samples from a training population comprised of a first trait subgroup where each member of the subgroup has Asymptomatic Chagas as compared with a second trait subgroup wherein each member of the second trait subgroup does not have Chagas using the Affymetrix® platform. The table also shows the sequences of selected products of the identified molecular markers.

Table 5U shows the molecular markers that are differentially expressed in blood samples from a training population comprised of a first trait subgroup where each member of the subgroup has Symptomatic Chagas as compared with a second trait subgroup wherein each member of the second trait subgroup does not have Chagas using the Affymetrix® platform. The table also shows the sequences of selected products of the identified molecular markers.

Table 5V shows the molecular markers that are differentially expressed in blood samples from a training population comprised of a first trait subgroup where each member of the subgroup has Bladder Cancer as compared with patients not having Bladder Cancer using the Affymetrix® platform. The table also shows the sequences of selected products of the identified molecular markers.

Table 6 tables are those tables which show those molecular markers that are differentially expressed in blood samples from a training population comprised of a first trait subgroup where each member of the subgroup has any one of a series of related conditions as compared to blood samples a second trait subgroup wherein each member of the second trait subgroup does not have said related conditions. The table also shows the sequences of selected products of the identified molecular markers.

Table 6A shows the molecular markers that are differentially expressed in blood samples from a training population comprised of a first trait subgroup where each member of the subgroup has Cancer as compared with a second trait subgroup wherein each member of the second trait subgroup does not have Cancer using the Affymetrix® platform. The table also shows the sequences of selected products of the identified molecular markers.

Table 6B shows the molecular markers that are differentially expressed in blood samples from a training population comprised of a first trait subgroup where each member of the subgroup with Cardiovascular Disease as compared with a second trait subgroup wherein each member of the second trait subgroup does not have a Cardiovascular Disease using the Affymetrix® platform. The table also shows the sequences of selected products of the identified molecular markers.

Table 6C shows the molecular markers that are differentially expressed in blood samples from a training population comprised of a first trait subgroup where each member of the subgroup has a Neurological Disease as compared with a second trait subgroup wherein each member of the second trait subgroup does not have a Neurological Disease using the Affymetrix® platform. The table also shows the sequences of selected products of the identified molecular markers.

Table 7 tables are those tables which show molecular markers that are differentially expressed in blood samples from with a condition wherein said condition is a treatment as compared to blood samples from patients without said treatment or with a different said treatment.

Table 7A shows the molecular markers that are differentially expressed in blood samples from a training population comprised of a first trait subgroup where each member of the subgroup is taking Celebrex® as compared a second trait subgroup wherein each member of the second trait subgroup is taking a Cox Inhibitor which was not Celebrex® using the ChondroChip™ platform. The table also shows the sequences of selected products of the identified molecular markers.

Table 7B shows the molecular markers that are differentially expressed in blood samples from a training population comprised of a first trait subgroup where each member of the subgroup is taking Celebrex® as compared with a second trait subgroup wherein each member of the second trait subgroup is not taking Celebrex® using the ChondroChip™ platform. The table also shows the sequences of selected products of the identified molecular markers.

Table 7C shows the molecular markers that are differentially expressed in blood samples from a training population comprised of a first trait subgroup where each member of the subgroup is taking Vioxx® as compared a second trait subgroup wherein each member of the second trait subgroup is not taking Vioxx® using the ChondroChip™ platform. The table also shows the sequences of selected products of the identified molecular markers.

Table 7D shows the molecular markers that are differentially expressed in blood samples from a training population comprised of a first trait subgroup where each member of the subgroup is taking Vioxx® as compared with a second trait subgroup wherein each member of the second trait subgroup on a Cox inhibitor but not on Vioxx® using the ChondroChip™ platform. The table also shows the sequences of selected products of the identified molecular markers.

Table 7E shows the molecular markers that are differentially expressed in blood samples from a training population comprised of a first trait subgroup where each member of the subgroup is taking NSAIDS as compared with patients not on NSAIDS using the ChondroChip™ platform. The table also shows the sequences of selected products of the identified molecular markers.

Table 7F shows the molecular markers that are differentially expressed in blood samples from a training population comprised of a first trait subgroup where each member of the subgroup is taking Cortisone as compared with a second trait subgroup wherein each member of the second trait subgroup on not on Cortisone using the ChondroChip™ platform. The table also shows the sequences of selected products of the identified molecular markers.

Table 7G shows the molecular markers that are differentially expressed in blood samples from a training population comprised of a first trait subgroup where each member of the subgroup is taking Visco Supplement as compared with a second trait subgroup wherein each member of the second trait subgroup not on Visco Supplement using the ChondroChip™ platform. The table also shows the sequences of selected products of the identified molecular markers.

Table 7H shows the molecular markers that are differentially expressed in blood samples from a training population comprised of a first trait subgroup where each member of the subgroup is taking Lipitor® as compared with a second trait subgroup wherein each member of the second trait subgroup not on Lipitor® using the ChondroChip™ platform. The table also shows the sequences of selected products of the identified molecular markers.

Table 7I shows the molecular markers that are differentially expressed in blood samples from a training population comprised of a first trait subgroup where each member of the subgroup is who are smokers as compared with a second trait subgroup wherein each member of the second trait subgroup who are not smokers using the ChondroChip™ platform. The table also shows the sequences of selected products of the identified molecular markers.

To further clarify, Tables IAA; IAB; IAD; IAE; IAG; IAH; IAT; IS; IT; IU; IW; 1Z(b); 3A; 3B; 3C; 3D; 3E; 3F; 3G; 3H; 31; 3K; 3L; 3P; 3Q; 3R; 4B; 4D; 4F; 4H; 4J; 4L; 4N; 4P; 4R; 4T; 4V; 5A; 5B; 5C; 5D; 5EE; 5F; 5G; 5H; 51; 5J; 5K; 5L; 5M; 5N; 50; 5P 5Q; 5R; 5S; 5T; 5U; 5V; 6A; 6B; 6C; 7F; and 7G each identify the molecular markers identified using the Affymetrix® genechip to screen the products of the majority of molecular markers of the human genome in accordance with step 202.

Tables IA; 1 AC; IB; 1C; ID; IE; IF; IG; IH; II; U; IK; IL; IM; IN; 10; IP; IQ; IR; IV; IX; IY; IZ; 2; 4A; 4C; 4E; 4G; 41; 4K; 4M; 40; 4Q; 4S; 4V; 7A; 7B; 7C; 7D; 7E; 7H; and 71 each identify molecular markers identified using our own ChondroChip™ genechip to screen the products of the majority of the molecular markers of the human genome.

Like reference numerals refer to corresponding parts throughout the several views of the drawings.

5. DETAILED DESCRIPTION

The embodiments of the present invention use novel approaches to screen and select molecular markers and develop classifiers that can be used to harness the use of molecular marker data from blood. The present invention thus provides systems and methods for constructing biological classifiers using molecular marker data from blood by providing a method to screen and select from a large variety of potential molecular markers so as to identify a small subset of molecular markers. The classifiers and the combinations of molecular markers identified using aspects of the current invention are useful for a wide variety of purposes including: diagnosis; prognosis; prediction of disease, stage of disease or disease risk; monitoring disease progression and/or regression; monitoring disease reoccurrence and identifying risk of disease reoccurrence; determining and/or predicting response to treatment and/or treatment outcomes; monitoring and/or predicting treatment compliance or non-compliance and the like. As used herein, a "condition" includes a mode or state of being including a physical, emotional, psychological or pathological state. A condition can be as a result of both "genetic" (ie genetically inherited) and/or "environmental" factors (ie the result of exposure to internal or external influences). In one embodiment of the invention, a condition is a disease. In another embodiment of the invention, a condition is a stage of a disease. In yet another embodiment of the invention, a condition is a mode or state of being which is not a disease. For example in one embodiment, a condition which is not a disease is a condition resulting from the progression of time. A condition resulting from progression of time can include, but is not limited to: memory loss, loss of skin elasticity, loss of muscle tone, and loss of sexual desire. In a further embodiment of the invention a condition which is not a disease is the response to treatment. A treatment can include, but is not limited to disease modifying treatments as well as treatments useful in mitigating the symptoms of disease. For example treatments can include drugs specific for a disease of the invention.

As used herein, the term "data" or "molecular marker data" generally refers to data reflective of the abundance of a product of a molecular marker in blood including either or both of RNA and protein.

As used herein, "diagnosis" includes the ability to determine that an individual has or does not have a specific condition or conditions. Diagnosis also refers to the ability to determine that an individual has one condition or conditions as compared with one or more other condition or conditions. In some embodiments, diagnosis refers to the ability to demonstrate an increased likelihood that an individual has a specific condition. "diagnosis" refers to the ability to demonstrate an increased likelihood that an individual has one condition as compared to a second condition. More particularly "diagnosis" refers to a process whereby there is an increased likelihood that an individual is properly characterized as having a condition ("true positive") or is properly characterized as not having a condition (or is properly characterized as having the second condition where the diagnosis is as between two conditions) ("true negative") while minimizing the likelihood that the individual is improperly characterized with said condition ("false positive") or improperly characterized as not being afflicted with said condition (or improperly characterized as having the second condition) ("false negative").

As used herein, the term "differential expression" refers to a difference in the level of expression of the RNA and/or protein products of a molecular marker of the invention, as measured by the amount or level of RNA or protein. In reference to RNA, it can include difference in the level of expression of mRNA, and/or one or more spliced variants of mRNA of the biomarker in one sample as compared with the level of expression of the same one or more biomarkers of the invention as measured by the amount or level of RNA, including mRNA and/or one or more spliced variants of mRNA in a second sample. "Differentially expressed" or "differential expression" can also include a measurement of the protein, or one or more protein variants encoded by a molecular marker of the invention in a sample or population of samples as compared with the amount or level of protein expression, including one or more protein variants of a molecular marker of the invention. Differential expression can be determined as described herein and as would be understood by a person skilled in the art. The term "differentially expressed" or "changes in the level of expression" refers to an increase or decrease in the measurable expression level of a given product of a molecular marker as measured by the amount of RNA and/or the amount of protein in a sample as compared with the measurable expression level of a given product of the molecular marker in a second sample. The first sample and second sample need not be from different patients, but can be samples from the same patient taken at different time points. The term "differentially expressed" or "changes in the level of expression" can also refer to an increase or decrease in the measurable expression level of a given molecular marker in a population of samples as compared with the measurable expression level of the molecular marker in a second population of samples. As used herein, "differentially expressed" when referring to a single sample can be measured using the ratio of the level of expression of a given molecular marker in said sample as compared with the mean expression level of the given molecular marker of a control population wherein the ratio is not equal to 1.0. Differentially expressed can also be used to include comparing a first population of samples as compared with a second population of samples or a single sample to a population of samples using either a ratio of the level of expression or using p-value. When using p-value, a nucleic acid transcript including hnRNA and mRNA is identified as being differentially expressed as between a first and second population when the p-value is less than 0.1, less than 0.05, less than 0.01, less than 0.005, less than 0.001 etc. When determining differential expression on the basis of the ratio of the level of molecular marker product—expression of an RNA or protein product of the molecular marker is differentially expressed if the ratio of the level of the RNA or protein product in a first sample as compared with that in a second sample is greater than or less than 1.0. For instance, a ratio of greater than 1, for example 1.2, 1.5, 1.7, 2, 3, 4, 10, 20, or a ratio of less than 1, for example 0.8, 0.6, 0.4, 0.2, 0.1. 0.05, of RNA or protein product of a molecular marker would be indicative of differential expression. In another embodiment of the invention, a molecular marker is differentially expressed if the mean level of expression of a nucleic acid transcript including the hnRNA and/or mRNA transcript in a first population as compared with its mean level of expression of the transcript in a second population is greater than or less than 1.0. For instance, a ratio of greater than 1, for example 1.2, 1.5, 1.7, 2, 3, 4, 10, 20, or a ratio less than 1, for example 0.8, 0.6, 0.4, 0.2, 0.1. 0.05 would be indicative of differential expression. In another embodiment of the invention a molecular marker is differentially expressed if the ratio of the level of the hnRNA and/or mRNA transcript in a first sample as compared with the mean level of the transcript of the second population is greater than or less than 1.0 and includes for example, a ratio of greater than 1, for instance 1.2, 1.5, 1.7, 2, 3, 4, 10, 20, or a ratio less than 1, for example 0.8, 0.6, 0.4, 0.2, 0.1. 0.05. "Differentially increased expression" refers to 1.1 fold, 1.2 fold, 1.4 fold, 1.6 fold, 1.8 fold, or more, relative to a standard, such as the mean of the expression level of the second population. "Differentially decreased expression" refers to less than 1.0 fold, 0.8 fold, 0.6 fold, 0.4 fold, 0.2 fold, 0.1 fold or less, relative to a standard, such as the mean of the expression level of the second population.

As used herein, the term "molecular marker" (or sometimes referred to as a "biomarker") refers to a gene or a genetic element. In some embodiments, the molecular marker of interest is identified by the Gene ID (formerly Locus Link ID) as is published by the National Center for Biotechnology Information (NCBI) Database as would be understood by a person skilled in the art.

As used herein, the term "oligonucleotide" is defined as a molecule comprised of two or more deoxyribonucleotides and/or ribonucleotides, and preferably more than three. Its exact size will depend upon many factors which, in turn, depend upon the ultimate function and use of the oligonucleotide. The oligonucleotides may be from about 8 to about 1,000 nucleotides long. Although oligonucleotides of 8 to 100 nucleotides are useful in the invention, preferred oligonucleotides range from about 8 to about 15 bases in length, from about 8 to about 20 bases in length, from about 8 to about 25 bases in length, from about 8 to about 30 bases in length, from about 8 to about 40 bases in length or from about 8 to about 50 bases in length.

The term, "primer", as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and the method used. For example, for diagnostic applications, depending on the complexity of the target sequence, the oligonucleotide primer typically contains 15-25 or more nucleotides, although it may contain fewer nucleotides. The factors involved in determining the appropriate length of primer are readily known to one of ordinary skill in the art. In general, the design and selection of primers embodied by the instant invention is according to methods that are standard and well known in the art, see Dieffenbach, C. W., Lowe, T. M. J., Dveksler, G. S. (1995) General Concepts for PCR Primer Design. In: PCR Primer, A Laboratory Manual (Eds. Dieffenbach, C W, and Dveksler, G. S.) Cold Spring Harbor Laboratory Press, New York, 133-155; Innis, M. A., and Gelfand, D. H. (1990) Optimization of PCRs. In: PCR protocols, A Guide to Methods and Applications (Eds. Innis, M. A., Gelfand, D. H., Sninsky, J. J., and White, T J.) Academic Press, San Diego, 3-12; Sharrocks, A. D. (1994) The design of primers for PCR. In: PCR Technology, Current Innovations (Eds. Griffin, H. G., and Griffin, A. M, Ed.) CRC Press, London, 5-11.

As used herein, the term "probe" means oligonucleotides and analogs thereof and refers to a range of chemical species that recognise polynucleotide target sequences through hydrogen bonding interactions with the nucleotide bases of the target sequences. The probe or the target sequences may be single- or double-stranded RNA or single- or double-stranded DNA or a combination of DNA and RNA bases. A probe is at least 8 nucleotides in length and less than the length of a complete gene. A probe may be 10, 20, 30, 50, 75, 100, 150, 200, 250, 400, 500 and up to 2000 nucleotides in length. Probes can include oligonucleotides modified so as to have a tag which is detectable by fluorescence, chemiluminescence and the like. The probe can also be modified so as to have both a detectable tag and a quencher molecule, for example Taqman® and Molecular Beacon® probes.

As used herein, the term "product of the molecular marker" or "molecular marker product" refers to the RNA or protein found in blood which corresponds to the molecular marker (ie is transcribed from the gene or genetic element or is translated from RNA which is transcribed from the gene or genetic element). For example, in some embodiments RNA resulting from the molecular marker can include one or more of the following species; hnRNA, niRNA, and/or one or more spliced variants of mRNA. In some embodiments, proteins resulting from the molecular marker can include any proteins found in blood which correspond to the RNA resulting from the molecular marker.

As used herein, the term "selectively amplified" or "selective amplification", refers to a process whereby one or more copies of a particular target nucleic acid sequence is selectively generated from a template nucleic acid. Selective amplification or selectively amplified is to be compared with amplification in general which can be used as a method in combination with, for example, random primers and an oligodT primer to amplify a population of nucleic acid sequences (e.g. mRNA). Selective amplification is preferably done by the method of polymerase chain reaction (Mullis and Faloona, 1987, Methods Enzymol. 155:335).

As used herein, the term "selectively binds" in the context of proteins encompassed by the invention refers to the specific interaction of any two of a peptide, a protein, a polypeptide, and an antibody, wherein the interaction preferentially occurs as between any two of a peptide, protein, polypeptide and antibody preferentially as compared with any other peptide, protein, polypeptide and antibody. For example, when the two molecules are protein molecules, a structure on the first molecule recognises and binds to a structure on the second molecule, rather than to other proteins. "Selective binding", "Selective binding", as the term is used herein, means that a molecule binds its specific binding partner with at least 2-fold greater affinity, and preferably at least 10-fold, 20-fold, 50-fold, 100-fold or higher affinity than it binds a non-specific molecule.

As used herein "selective hybridization" in the context of this invention refers to a hybridization which occurs as between a polynucleotide encompassed by the invention and an RNA, and its complement thereof (ie a cDNA copy), of the molecular marker of the invention, wherein the hybridization is such that the polynucleotide preferentially binds to the RNA products of the molecular marker of the invention relative to the RNA products of other molecular markers or other genes in the genome in question. In a preferred embodiment a polynucleotide which "selectively hybridizes" is one which hybridizes with a selectivity of greater than 70%, greater than 80%, greater than 90% and most preferably of 100% (i.e. cross hybridization with other RNA species preferably occurs at less than 30%, less than 20%, less than 10%). As would be understood to a person skilled in the art, a polynucleotide which "selectively hybridizes" to the RNA product of a biomarker of the invention can be determined taking into account the length and composition.

As used herein, "specifically hybridizes", "specific hybridization" refers to hybridization which occurs when two nucleic acid sequences are substantially complementary (at least about 65% complementary over a stretch of at least 14 to 25 nucleotides, preferably at least about 75% complementary, more preferably at least about 90% complementary). See Kanehisa, M., 1984, Nucleic acids Res., 12:203, incorporated herein by reference. As a result, it is expected that a certain degree of mismatch is tolerated. Such mismatch may be small, such as a mono-, di- or tri-nucleotide. Alternatively, a region of mismatch can encompass loops, which are defined as regions in which there exists a mismatch in an uninterrupted series of four or more nucleotides. Numerous factors influence the efficiency and selectivity of hybridization of two nucleic acids, for example, the hybridization of a nucleic acid member on an array to a target nucleic acid sequence. These factors include nucleic acid member length, nucleotide sequence and/or composition, hybridization temperature, buffer composition and potential for steric hindrance in the region to which the nucleic acid member is required to hybridize. A positive correlation exists between the nucleic acid length and both the efficiency and accuracy with which a nucleic acid will anneal to a target sequence. In particular, longer sequences have a higher melting temperature (TM) than do shorter ones, and are less likely to be repeated within a given target sequence, thereby minimizing non-specific hybridization. Hybridization temperature varies inversely with nucleic acid member annealing efficiency. Similarly the concentration of organic solvents, e.g., formamide, in a hybridization mixture varies inversely with annealing efficiency, while increases in salt concentration in the hybridization mixture facilitate annealing. Under stringent annealing conditions, longer nucleic acids, hybridize more efficiently than do shorter ones, which are sufficient under more permissive conditions.

As used herein, the term "specifically binds" refers to the interaction of two molecules, e.g., a ligand and a protein or peptide, or an antibody and a protein or peptide wherein the interaction is dependent upon the presence of particular structures on the respective molecules. For example, when the two molecules are protein molecules, a structure on the first molecule recognises and binds to a structure on the second molecule, rather than to proteins in general. "Specific binding", as the term is used herein, means that a molecule binds its specific binding partner with at least 2-fold greater affinity, and preferably at least 10-fold, 20-fold, 50-fold, 100-fold or higher affinity than it binds a non-specific molecule.

As herein used, the term "standard stringent conditions" and "stringent conditions" means hybridization will occur only if there is at least 95% and preferably, at least 97% identity between the sequences, wherein the region of identity comprises at least 10 nucleotides. In one embodiment, the sequences hybridize under stringent conditions following incubation of the sequences overnight at 42 DC, followed by stringent washes (0.2×SSC at 65 D C). The degree of stringency of washing can be varied by changing the temperature, pH, ionic strength, divalent cation concentration, volume and duration of the washing. For example, the stringency of hybridization may be varied by conducting the hybridization at varying temperatures below the melting temperatures of the probes. The melting temperature of the probe may be calculated using the following formulas:

For oligonucleotide probes, between 14 and 70 nucleotides in length, the melting temperature (Tm) in degrees Celcius may be calculated using the formula: $Tm=81.5+16.6(\log [Na+])+0.41 (\text{fraction } G+C)-(600/N)$ where N is the length of the oligonucleotide.

For example, the hybridization temperature may be decreased in increments of 5° C. from 68° C. to 42° C. in a hybridization buffer having a Na+ concentration of approximately IM. Following hybridization, the filter may be washed with 2×SSC, 0.5% SDS at the temperature of hybridization. These conditions are considered to be "moderate stringency" conditions above 50° C. and "low stringency" conditions below 50° C. A specific example of "moderate stringency" hybridization conditions is when the above hybridization is conducted at 55° C. A specific example of "low stringency" hybridization conditions is when the above hybridization is conducted at 45° C.

If the hybridization is carried out in a solution containing formamide, the melting temperature of the annealing nucleic acid strands may be calculated using the equation $Tm=81.5+16.6(\log [Na+])+0.41(\text{fraction } G+C)-(0.63\% \text{ formamide})-(600/N)$, where N is the length of the probe.

If the hybridization is carried out in a solution containing formamide, the melting temperature of the annealing nucleic acid strands may be calculated using the equation $Tm=81.5+$ 16.6(log [Na$^+$])+0.41(fraction G+C)−(0.63% formamide)−(600/N), where N is the length of the probe.

For example, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50 DC. Hybridization conditions are considered to be "moderate stringency" conditions when hybridization fluids are comprised of above 25% formamide and "low stringency" conditions when hybridization fluids are comprised of below 25% formamide. A specific example of "moderate stringency" hybridization conditions is when the above hybridization is conducted at 30% formamide. A specific example of "low stringency" hybridization conditions is when the above hybridization is conducted at 10% formamide.

As used herein, the term "responder" is used to mean an individual who responds to treatment. The use of the term "responds to treatment" depends upon the context of the treatment and the disease or condition, but in some embodiments indicate a sufficiently effective and safe response by an individual to the administration of treatment.

As used herein, the term "non-responder" is used to mean an individual who does not respond positively to treatment. The use of the phrase "does not respond to treatment" also depends upon the context of the treatment and the disease or condition, but in some embodiments indicates an ineffective or unsafe response by an individual to the administration of treatment.

As used herein, the term "trait" is a mode or state of being including a physical, emotional, psychological or pathological state. A trait can include both "genetic" and/or "environmentally" influenced factors. The term "genetic factors" means genetically inherited elements which affect one or more traits as a result of the genetic makeup of the individual. The term "environmental factors" includes exposure to internal or external influences including but not limited to medical treatments, non-medical drugs, pollution, environmental toxins, lead poisoning, mercury poisoning, exposure to genetically modified organisms, radioactivity, pesticides, insecticides, cigarette smoke, alcohol, or exercise and can affect abundance of RNA or affect gene expression as a result of epigenetic mutations and/or non genetic mutations. A physiological or pathological trait can include the status with regards to a condition including having a condition including a disease, having risk factors of a disease having a certain stage of disease or having a certain response to treatment or a risk of a certain response to treatment. In some cases a displayed trait can actually be the result of one or more underlying traits. A trait also includes clinically measurable parameters including those clinically measurable parameters which are indicators of state of health or disease. For example, a clinically measurable parameter includes blood pressure, lung capacity, electrolyte level, enzyme levels (e.g. Serum Glutamic Oxaloacetic Transaminase, alkaline phosphatase, Gamma-Glutamyltransferase or Gamma-Glutamyl Transpeptidase, Lactic dehydrogenase) hormone levels (e.g. thyroid stimulating hormone); protein levels (e.g. Prostate specific antigen PSA) and the like. Clinically measurable parameters can include disease specific clinical indicators, for example prostate specific antigen as an indicator of prostate cancer; insulin levels as an indicator of diabetes; thyroid stimulating hormone levels as an indicator of thyroid disorder and the like.

As used herein, the term "trait subgroup" is used to define a group of subjects where each subject has at least one trait or group of traits in common, for example, each subject has a disease, a specific stage of disease, same response to treatment, taking the same drug, etc.

As used herein, the terms "treatment", "treat", and "treating" includes administration of one or more compounds, combination of one or more compounds, application of a non-compound based therapeutic regimen, or any combination thereof where administration includes application of a single treatment, a regiment or course of treatment etc. to reduce or amelioration of the progression, severity and/or duration of a disease or condition and/or the reduction or amelioration of the symptoms of a disease or condition resulting from the use of a treatment and/or treatment regime.

5.1 Inventive Systems and Algorithms

FIG. 1 shows an exemplary system according to an embodiment of the invention that supports the functionality described herein. The system is preferably a computer system 10 having:

one or more central processors 22;

a main non-volatile storage unit 14, for example a hard disk drive, for storing software and data, the storage unit 14 controlled by storage controller 12;

a system memory 36, preferably high speed random-access memory (RAM), for storing system control programs, data, and application programs, comprising programs and data loaded from non-volatile storage unit 14; system memory 36 may also include read-only memory (ROM);

an optional user interface 32, comprising one or more input devices (e.g., keyboard 28) and a display 26 or other output device;

an optional network interface card 20 for connecting to any wired or wireless communication network 34 (e.g., a wide area network such as the Internet);

an internal bus 30 for interconnecting the aforementioned elements of the system; and a power source 24 to power the aforementioned elements.

Operation of computer 10 is controlled primarily by operating system 40, which is executed by central processing unit 22. Operating system 40 can be stored in system memory 36. In addition to operating system 40, in a typical implementation, system memory 36 includes various components described below. Those of skill in the art will appreciate that such components can be wholly resident in RAM 36 or non-volatile storage unit 14. Furthermore, at any given time, such components can partially reside both in RAM 36 and non-volatile storage unit 14. Further still, some of the components shown in FIG. 1 as being resident in RAM 36 can be resident in another computer (a remote computer) that is addressable by computer 10 over wide area network 34. It will be appreciated that such a remote computer may physically be resident in the same room as computer 10 or in another physical location. As illustrated in FIG. 1, in one exemplary embodiment of the invention, RAM 36 comprises programs and data to interact with components in the computer system 10 for configuring:

file system 42 for controlling access to the various files and data structures used by embodiments of the present invention;

a training population 44 for use in construction of one or more classifiers;

a molecular marker data processing module I-54 for processing molecular marker data representative of a genome or a portion thereof for members of training population 44;

a molecular marker screening module A (56A) for identifying molecular markers whose molecular marker data individually discriminates between two or more trait subgroups of the training population using molecular marker data of module 54;

a molecular marker screening module B (56B) for identifying molecular markers whose molecular marker data do not individually discriminate, but demonstrate ability to differentiate between two or more trait subgroups of the training population when used in combination using molecular marker data of module 54;

a candidate molecular marker data structure 58 for storing information about candidate molecular markers identified by molecular marker candidate screening module 56A and optionally molecular marker candidate screening module 56B;

a second molecular marker data processing module II 61 for processing additional molecular marker data for a selection of the candidate molecular markers identified in screening module 56A and, optionally, screening module 56B for members of a training population;

an outlier selection module 57 for evaluating molecular marker data identified in either module 56A and/or 56B or module 61 so as to remove one or more individuals from the training population as outliers;

a combination module 61-5 which selects combinations of molecular markers from candidate molecular markers identified in module 56A and optionally module 56B a molecular marker classifier construction module 62 for constructing candidate classifiers from combinations of molecular markers identified by molecular marker combination module 61-5;

a molecular marker classifier evaluation module 64 for evaluating and selecting candidate classifiers constructed by molecular marker construction module 62;

a classifier polling and reporting module 66 for receiving patient or subject molecular marker data and polling one or more classifiers selected by evaluation module 64 in order to determine whether a patient or subject has the disease or trait associated with each of the respective classifiers;

a patient database 68 for storage of molecular marker data for diagnostic, prognostic or predictive use; and a classifier database 70 for storage of one or more classifiers selected by molecular marker classifier evaluation module 64.

As illustrated in FIG. 1, computer 10 comprises software program modules and data structures. The data structures either stored in computer 10 or accessible to computer 10 include a training population 44, candidate molecular marker data structures 58, patient database 68, and classifier database 70. Each of these data structures can comprise any form of data storage system including, but not limited to, a flat ASCII or binary file, an Excel spreadsheet, a relational database (e.g. SQL), or an on-line analytical processing (OLAP) database (MDX and/or variants thereof). In some specific embodiments, such data structures are each in the form of one or more databases that include hierarchical structure (e.g., a star schema). In some embodiments, such data structures are each in the form of databases that do not have explicit hierarchy (e.g., dimension tables that are not hierarchically arranged). In some embodiments, each of the data structures stored or accessible to system 10 are single data structures. In other embodiments, such data structures in fact comprise a plurality of data structures (e.g., databases, files, archives) that may or may not all be hosted by the same computer 10. For example, in some embodiments, training population 44 comprises a plurality of Excel spreadsheets that are stored either on computer 10 and/or on computers that are addressable by computer 10 across wide area network 34. In another example, patient database 68 comprises a database that is either stored on computer 10 or is distributed across one or more computers that are addressable by computer 10 across wide area network 34. Section 5.9 describes exemplary architectures for training population 44, candidate molecular marker data structure 58, patient database 68, and/or classifier database 70.

It will be appreciated that many of the modules and data structures illustrated in FIG. 1 can be located on one or more remote computers. For example, some embodiments of the present application are web service-type implementations. In such embodiments, classifier polling and reporting module 66 and other modules can be used by a physician to treat a patient and can reside on a client computer that is in communication with computer 10 via network 34. In some embodiments, for example, classifier polling and reporting module 66 can be an interactive web page.

In some embodiments, training population 44, candidate molecular marker data structure 58, patient database 68 and/or classifier database 70 and modules (e.g. modules 54, 56A, 56B, 57, 61, 61-5, 62, 64, and 66) illustrated in FIG. 1 are on a single computer (computer 10) and in other embodiments one or more of such data structures and module are hosted by one or more remote computers (not shown). Any arrangement of the data structures and software modules illustrated in FIG. 1 on one or more computers is within the scope of the present invention so long as these data structures and software modules are addressable with respect to each other across network 34 or by other electronic means. Thus, the present invention fully encompasses a broad array of computer systems.

Now that an overview of a system in accordance with one embodiment of the present invention has been described, various advantageous methods in accordance with embodiments of the present invention will now be disclosed in conjunction with FIGS. 2 through 5. FIG. 2 is a flowchart showing a method of selecting molecular markers and developing one or more classifiers or groups of classifiers according to an embodiment of the invention.

Step 202.

Figure 2A:
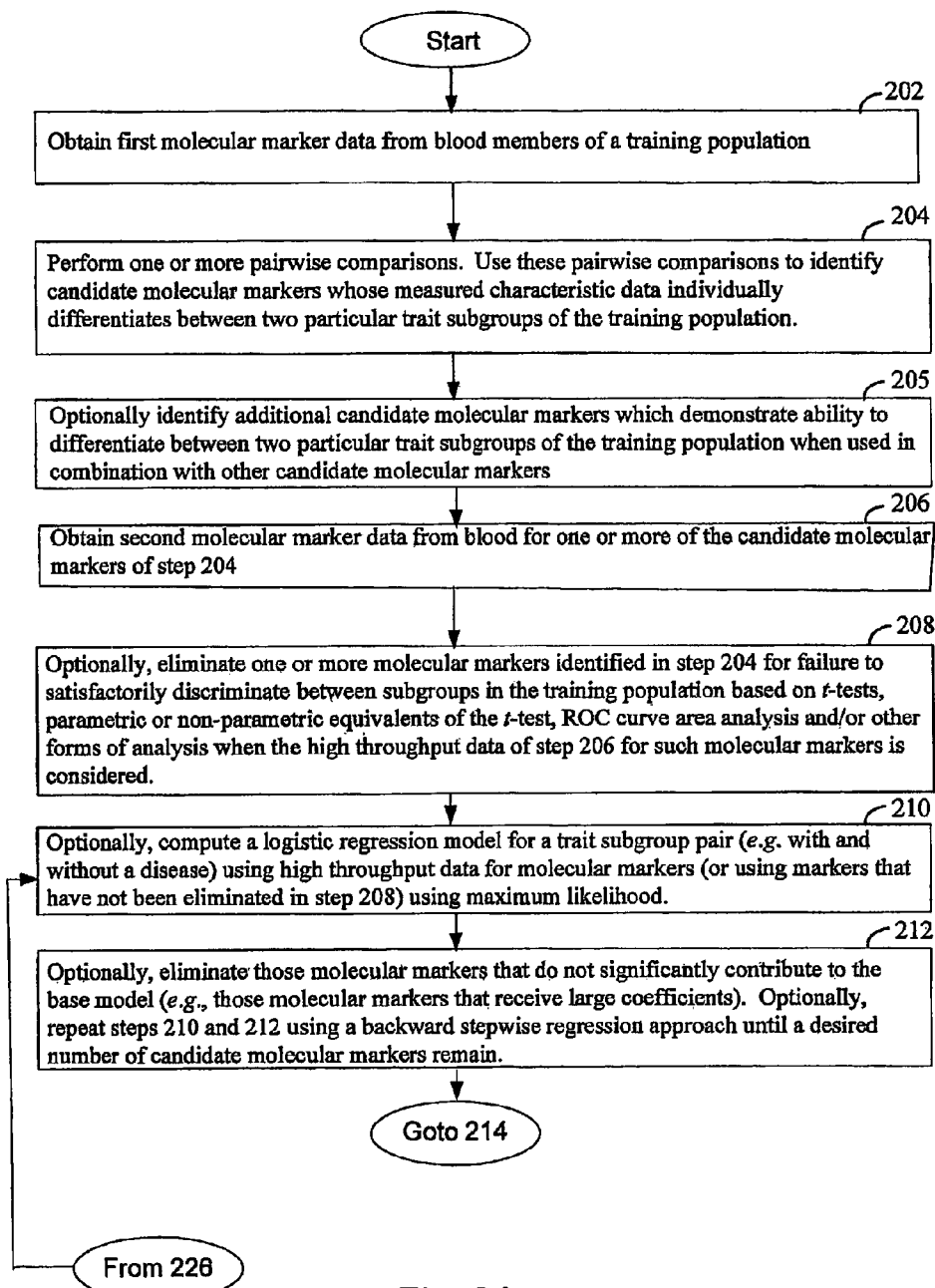
FIG. 2 illustrates a method for deriving biological classifiers in accordance with an embodiment of the present invention.
Figure 2B:
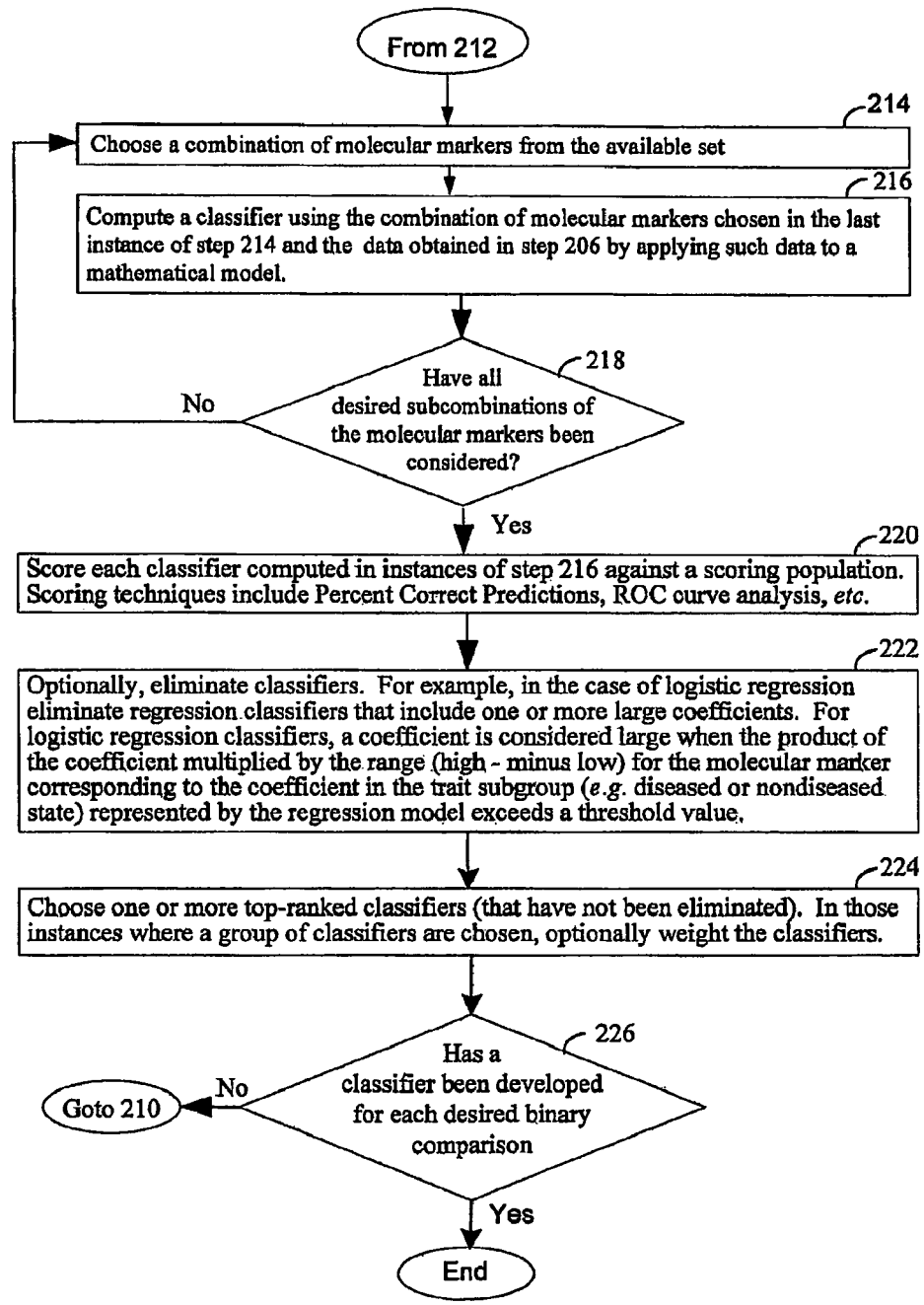

Referring to FIG. 2A, in step 202, molecular marker data reflective of the abundance of each of a plurality of RNA and/or proteins found in the blood for members of training population 44 is obtained using one or more of the techniques as described in Section 5.3 and/or 5.4. In some embodiments, the data is reflective of the abundance of RNA products of the molecular marker. In some embodiments, the RNA products are those expressed in blood. In other embodiments, the RNA products are those which are found in blood, but may not necessarily be expressed in blood (e.g. in instances where sufficient mRNA is transported into the blood to be detected. In some embodiments, the data is reflective of the abundance of protein products of the molecular markers. In some embodiments, the data is reflective of the level of proteins expressed in blood. In other embodiments, the data is reflective of proteins found in blood in sufficient quantity to be detected. Measuring of molecular marker data (ie data reflective of the level of the product of the molecular marker) can be done using those techniques known to persons skilled in the art. Note that in some embodiments, data may be obtained using public sources or other sources of data rather than performing one or more of the techniques described. For example, it is anticipated that databases of microarray data collected from blood may be available in future.

In some embodiments, the molecular marker data for each molecular marker is obtained using the same technique to allow greater comparability. In some instances a priori information is known about all or a portion of such genes and in some embodiments apriori information about such genes is either not known or not considered in step 202. In some embodiments the molecular markers resulting from step are those molecular markers identified in Tables IA through to 71.

Measurement of molecular marker data of a plurality of the molecular markers in the blood of each member of training population 44 can be done using any known technique and preferably is done using large scale techniques which allow for the ability to obtain data for a large number of molecular markers and/or for a large number of individuals quickly and efficiently and at a relatively low cost. For example, microarray techniques and RT-PCR and/or Quantitative RT-PCR can be useful large scale techniques. For example, a high throughput or large scale technique is a technique which allows one to obtain data for large numbers of genes concurrently e.g. 1,000 genes, 5,000 genes, 10,000 genes, 15,000 genes 30,000 genes; or all of the genes of the genome of interest. It is expected that additional techniques are being developed and are also useful in embodiments of the invention to screen large numbers of genes quickly and efficiently.

Training population 44 includes a population of individuals made up of one or more trait subgroups with each individual in such trait subgroups having one or more traits.

In some embodiments, each trait subgroup represented in training population 44 includes molecular marker data from at least 3-4 different subjects. More preferably, each trait subgroup represented in training population 44 includes molecular marker data for at least ten different subjects. Still more preferably each trait subgroup represented in the training population 44 includes molecular marker data for at least 30, 40, 50, 100, 200, 500, 1000 or more subjects.

Each training population is selected to include two or more trait subgroups, each subgroup comprising trait subgroup members. Each of these two or more trait subgroups differs with respect to a trait of interest and/or an aspect of a trait of interest. In one embodiment, the members of each of the trait subgroups have been diagnosed as having or not having the trait of interest by one or more known techniques. In another embodiment, the members of each trait subgroup are diagnosed for having or not having the trait of interest using a well accepted methodology for diagnosing of said trait.

For example, each member of a first trait subgroup of the training population has liver cancer, whereas each member of a second trait subgroup of the training population does not have liver cancer. In another embodiment, each member of a first trait subgroup of the training population has Alzheimer's, whereas each member of a second trait subgroup of the training population has manic depressive disorder, and each member of a third trait subgroup of the training population has schizophrenia, and each member of a fourth trait subgroup does not have any of the above conditions. In another example, the trait of interest is a disease such as prostate cancer, and the aspect of interest is the degree of advancement of the prostate cancer. Thus, each member of the first trait subgroup can be those subjects that have early stage prostate cancer, each member of a second trait subgroup can be those subjects that have later stage prostate cancer and each member of a third trait subgroup can be those subjects that do not have prostate cancer. In another example, the trait of interest is responsiveness of individuals having musculoskeletal disorders to a Cox 2 inhibitor. A first trait subgroup is comprised of individuals who are responsive to a treatment, a second trait subgroup is comprised of individuals who are responsive to treatment but demonstrate a toxic side-effect, and a third trait subgroup is comprised of individuals who are nonresponsive to treatment. In another embodiment, one trait subgroup can include those subjects that have not yet undergone treatment but who are later identified as being responders to treatment and a second trait subgroup can include those subjects that have not yet undergone treatment but who are later identified as non responders (e.g. demonstrates a toxic side-effect, demonstrates no improvement in condition, demonstrates a worsening of condition, etc.).

In some embodiments, members of each trait subgroup of the training population 44 are preferably selected such that each trait subgroup of the training population 44 has a similar distribution with respect to at least one, two, three, four, five, six, one or more, two or more, three or more, four or more, five or more, six or more, between one and 1000 other traits. For example, age, sex, body mass index (BMI), genetic variation information (e.g., gene SNP mutations, restriction fragment length polymorphisms, microsatellite markers, restriction fragment length polymorphisms, and presence, absence or characterization of short tandem repeats), treatment regimens; co-morbidities; concentrations of metabolites, blood chemistry levels, and/or other indicators of health and/or wellness.

A treatment can include, but is not limited to, disease modifying treatments as well as treatments useful in mitigating the symptoms of disease and includes administration of one or more compounds, combinations of one or more compounds, application of a non-compound based therapeutic regimen, or any combination thereof where administration includes application of a single treatment, a regimen or course of treatment and the like. For example, treatments can include drugs specific for a disease such as drugs specific for Alzheimer's, cardiovascular disease, manic depression syndrome, schizophrenia, diabetes cancers including liver cancer, testicular cancer, bladder cancer, prostate cancer, kidney cancer, breast cancer, colon cancer, osteoarthritis, rheumatoid arthritis, osteoporosis, ankylosing spondylitis, or any other disease including those listed herein. For example, treatments can include but are not limited to administration of VIOXX®, Celebrex®, non-steroidal anti-inflammatory drugs (NSAIDS), cortisone, visco supplement, Lipitor®, Adriamycin®, Cytoxan®, Herceptin®, Nolvadex®, Avastin®, Erbitux®, Fluorouracil®, Largactil®, Sparine®, Vesprin®, Stelazine®, Fentazine®, Prolixin®, Compazine®, Tindal®, Modecate®, Moditen®, Mellarin, Serentil, Norvane®, Fluanxol®, Clopixol®, Taractan®, Depixol®, Clopixol®, Haldol®, Haldol®, Decanoate, Orap®, Inapsine®, Imap®, Semap®, Loxitane®, Daxol®, lithium, anticonvulsants (e.g., carbamazepine), antidepressants, and/or Moban®. More generally, a treatment can include any treatment or drug described in the *Compendium of Pharmaceuticals and Specialties*, Canadian Pharmaceutical Association; 26th edition, June, 1991; Krogh, *Compendium of Pharmaceuticals and Specialties*, Canadian Pharmaceutical Association; 27th edition, April, 1992. In another embodiment, a treatment can include administration of any compound described in the United States Food and Drug Administration list of approved drug products (the "Orange Book") that is found at http://www.mco.edu/research/fda.html.

In some embodiments, molecular marker data is not obtainable from each member of a training population or each member of a trait subgroup (for example, using microarray technology there may be an insufficient signal for one or more molecular markers for any particular member of the training population). Nevertheless, as would be understood by a person skilled in the art, candidate molecular markers can still be selected on the basis of the molecular marker data so long as data is obtainable for a sufficient number of molecular markers from a sufficient number of members of the training population. For example, for each molecular marker, it is sufficient if data is available for at least 75%, 80%, 85%, 90% or 95% of the each trait subgroup of the training population.

Section 5.2 provides details on the types of blood samples from subjects in the training population that can be used to obtain data for molecular markers. Section 5.2 further provides details on how such blood samples can be obtained. Section 5.2 also provides details on the types of subjects that can be used to form training population 44 and the types of subpopulations that can be used in the training population.

Figure 4:
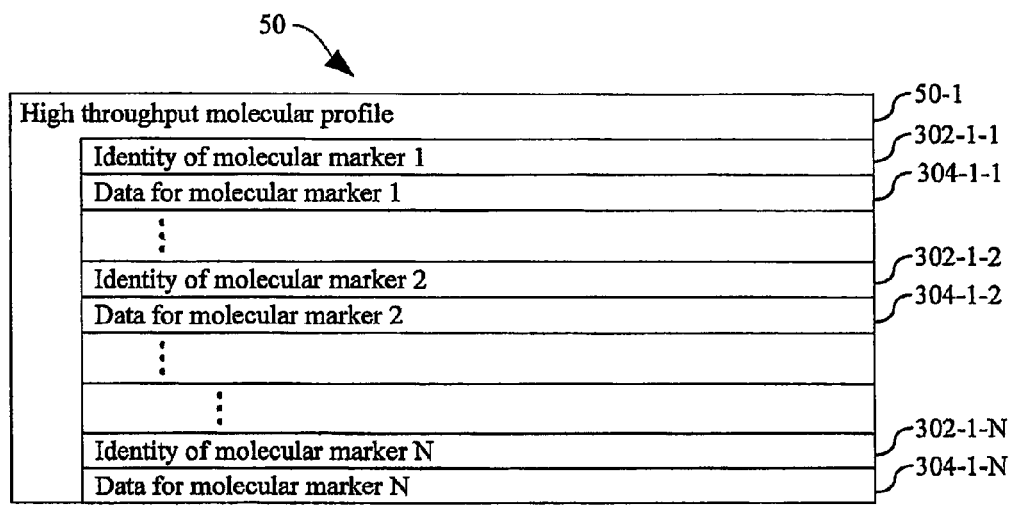
FIG. 4 illustrates a data structure for storing high throughput information for a plurality of molecular markers in accordance with one embodiment of the present invention.

FIG. 1 illustrates the data structure of a training population 44 in accordance with one embodiment of the present invention. There is a record 46 for each subject in training population 44. Each record 46 includes an optional subject identifier 48 for uniquely identifying the subject. Each record 46 includes a molecular marker data file 50 for storage of the molecular marker data measured in step 202. FIG. 4 provides more details on a molecular profile 50 resulting from Molecular Marker data processing module I in accordance with one embodiment of the present invention. The molecular profile 50 of FIG. 4 includes an identifier 302 for each molecular marker 302 tracked by profile 50. Then, for each respective molecular marker 302 in profile 50, there exists one or more measurements of molecular marker data 304. In some embodiments, more than one data point is measured for molecular markers 302. If more than one data point is measured for a molecular marker, then a statistical measure of central tendency (e.g. mean, median, average etc.) can be computed. Accordingly, such measurements for molecular marker data 304 can be stored in data structure 50.

There exists a trait characterization field 52 for each subject in training population 44. Preferably as many as possible traits of each member of training population 44 are documented in a trait characterization record (52). Documented traits include known condition or clinically measurable parameters; genetic likelihood of disease or condition; medications both past and current; environmental exposures, ethnicity, age, sex and the like. In some embodiments, training population 44 includes only two trait subgroups and trait characterization 52 is a binary choice between two values, where one value indicates that the corresponding subject belongs in a first trait subgroup and a second value indicates that the subject belongs in a second trait subgroup. In some embodiments, training population 44 is divided into a plurality of lists, where each list in the plurality of lists represents a different trait subgroup. In such embodiments, there is no need for a phenotypic characterization field 52.

Although not illustrated in FIG. 1, in some embodiments, there exists a scoring population in addition to the training population. The scoring population is used to evaluate each of the classifiers derived from the training population. The scoring population is made up of one or more individuals that have at least two trait subgroups in common with the training population. In some embodiments, multiple scoring populations are generated from the training population using one or more resampling or cross validation procedures including: bootstrapping; leave one out; leave n out; percent split and the like so as to evaluate the classifiers derived from the training population. In preferred embodiments, the members of the scoring population are not the members used in the training population.

In some embodiments, some aspects of step 202 are performed by first data molecular processing module I 54. As such, first data molecular processing module 54 can be a known software program, such as commercially available and/or academically available data processing programs.

Step 204.

In step 204, using the data measured in step 202, individual candidate molecular markers are identified, where the molecular marker data allows the differentiation as between two of the trait subgroups of the training population. In some embodiments, step 204 represents a series of pairwise comparisons, where each pairwise comparison is between molecular marker data for subjects from two different trait subgroups. In other words, data associated with molecular markers from a population of samples having one aspect of a trait of interest (a first trait subgroup) are compared with a population of samples having a second aspect of a trait of interest (a second trait subgroup) so as to identify molecular markers that are able to differentiate between the two trait subgroups (ie the molecular marker data enables the ability to differentiate between the two trait subgroups.

In instances where more than two trait subgroups are represented by a training population 44, more than two pairwise comparisons can be performed on the molecular marker data to identify lists of candidate molecular markers for each of the possible pairwise comparison.

A number of statistical techniques can be used to perform the pairwise comparisons of step 204. In some embodiments, standard statistical techniques such as a t-test are used. Methods based on conventional t-tests provide the probability (P) that a difference in measured values for the data of a molecular marker between two different trait subgroups occurs by chance. See, for example, Baldi et al, 2001, Bioinformatics 17, pp. 509-519, 2001, which is hereby incorporated herein by reference in its entirety. The t-test compares the actual difference between two means in relation to the variation in the data (expressed as the standard deviation of the difference between the means). For instance, to determine whether a particular molecular marker discriminates between a first trait subgroup and a second trait subgroup, the mean of the data for the molecular marker in the first trait subgroup is compared to the mean of the data for the molecular marker in the second subgroup in accordance with the t-test. In some embodiments, the molecular marker data is such that it is deemed to discriminate between two trait subgroups when the t-test yields a score that matches or exceeds the $p=0.05$ level (95% confidence, "significant confidence"), the/?=0.01 level (99% confidence, "highly significant confidence") or $p=0.001$ (99.9% confidence, "very highly significant confidence"). In some embodiments, the t-test is applied with a Bonferroni correction or similar form of correction. In some embodiments, rather than using a t-test, nonparametric equivalents such as the Wald-Wolfowitz runs test, the Mann-Whitney U test, the Kolmogorov-Smirnov two-sample test or ROC are used.

In some embodiments, training population molecular marker data is obtained using a microarray and the Significant Analysis of Microarrays technique of Tusher et al. is used to identify molecular markers whose data discriminates between trait subgroups. See, for example, Tusher et al, 2001, Proc. Natl. Acad. Sci. USA 98, 5116-5121. In some embodiments, Manduchis' algorithms for assigning confidence to differentially expressed genes is used to identify molecular markers whose data discriminates trait subgroups. See, for example, Manduchi et al, 2000, Bioinformatics 16, 685-598.

In some embodiments, there are a number of different trait subgroups represented within the training population. Thus, in such embodiments, application of a series of pairwise t-test can become computationally intensive and prone to underinclusiveness in the identification of discriminating molecular markers resulting for each binary comparison since the number of pairwise comparisons that must be performed grows quickly as a function of the number of trait subgroups present in training population 44. For example, if there are seven trait subgroups present in training population 44, a total of 21 pairwise (t-test class) test can be performed. In such embodiments, analysis of variance (ANOVA) can be used to simultaneously consider whether the data for a molecular marker produces statistically different means for each of the phenotypic data structures. ANOVA considers the data for a given molecular marker from each of the trait subgroups present in training population 44 and produces a single number (the F-statistic) that can be evaluated for significance at any desired confidence value (e.g., the/?=0.05 level, the/?=0.01 level, the/?=0.001 level, etc). ANOVA is described, for example, in Draghici, *Data Analysis Tools For DNA Microarrays*, 2003, Chapman & Hall, CRC Press, New York, pp. 155-187, which is hereby incorporated herein by reference in its entirety. In some embodiments, nonparametric equivalents to ANOVA, such as the *Kruskal-Wallis analysis of ranks test*, the Median test, Friedman's two-way analysis of variance, or the Cochran Q test, are used to identify molecular markers that have statistically different means as between two of the rait subgroups. In some embodiments, after running ANOVA, a means comparisons test such as Duncan's, Student-Newman-Keuls (SNK), Tukey-Kramer, Tukey's HSD, or Least Significant Difference (LSD) are run to determine which molecular markers have data that statistically differentiates as between one or more of the trait subgroups tested (e.g. has statistically different values in one or more of the trait subgroups tested). In some embodiments, such tests are performed instead of ANOVA or pairwise t-tests to identify molecular markers that discriminate two or more trait subgroups.

In some embodiments, a parametric test and a nonparametric test are run in step 204. If there are only two trait subgroups being compared (e.g., non-disease versus disease) then a Welch t-test (parametric test) and a Mann-Whitney test are used without multiple test corrections at decreasing p-values {e.g., $p<0.05$, $p<0.01$, $p<0.005$, $p<0.001$, etc.) until the number of candidate molecular markers is less than 50, less than 100, less than 150, less than 200, less than 250 etc. If three or more trait subgroups are being compared, the Kruskal-Wallis (nonparametric) and Welch ANOVA (parametric) tests are used. Following the same procedure for instances where only two trait subgroups are being compared, additional molecular marker sets are produced in conjunction with multiple test corrections. An example of a test correction is the Benjamin-Hochberg false discovery rate. In some embodiments the post-hoc statistical tests for groups of three or more provided in GeneSpring version 6.1+ is used. The post-hoc test provides a means for determining which molecular markers are different between particular trait subgroups. Such post-hoc tests include the Student Newman Keuls test and the Tukey test.

In some embodiments, data for a test molecular marker from all possible trait subgroups in training population 44 is not used. Rather, similar to the case where pairwise t-tests are used, ANOVA is used to determine whether the data for a molecular marker can discriminate between some or all of the trait subgroups. For example, consider the case in which training population 44 includes five trait subgroups. In one approach, a pairwise t-test can be used to identify molecular markers that statistically discriminate (e.g. p=0.05) between one of the possible pairs of trait subgroups in the training population. Similarly, ANOVA can be used to identify molecular markers that statistically discriminate between one of the possible triplets in the training population. Alternatively, ANOVA can be used to identify molecular markers that statistically discriminate between one of the possible quadruplets in the training population.

In some embodiments, either in addition to using statistical methods, or independently of statistical methods such as described herein, processing step 204 to select candidate molecular markers is done by looks for differential data abundances (e.g., differential expression). Such methods differ from those described above in the sense that variance as between the level of expression as between members of the same trait subgroup are not necessarily considered. In order to compare differential expression as between two or more trait subgroups, a statistical measure of central tendency (e.g. mean, median, average etc.) can be computed for each molecular marker within any trait subgroup. In some embodiments, the measure of differential data abundance (or differential expression) for a molecular marker product as between a first trait subgroup and a second trait subgroup is determined by measuring the fold change, for example a fold change of greater than 1.5, 2.0, 2.5, 3.0, 4.0 or higher can be selected. In another embodiment, the measure of differential data abundance need not be quantified, but molecular markers products which on visual inspection display a clear difference in expression (ie abundance levels) as between two trait subgroups can be selected. To illustrate, consider a population P' that comprises trait subgroups "A" and "B". That is, each member of P' is classified into either subgroup "A" or "B" based on whether or not they exhibit or have a particular trait. In this situation, products of molecular markers that are present in large quantities/abundance in one group ("A" or "B") but not the other group are identified. For instance, molecular markers that strongly express in subgroup "A" but not in subgroup "B" can be identified from the measurements taken for each member of each subgroup in step 202. Likewise, molecular markers that express strongly in subgroup "B" but not subgroup "A" can be identified. These patterns of differential abundance of the products of the molecular markers can be used to identify candidate molecular markers. For an illustration of this approach, see Glob et al. 1999, Science 286: 531.

In embodiments where molecular markers are identified in select pairwise tests, such as pairwise t-tests or ANOVA tests of subsets of the total number of trait subgroups in training population 44, there might be several different lists of molecular markers. For example, molecular marker list A might include molecular markers whose measured data (including normalized data etc.) discriminates between a first and second trait subgroup as determined by a first pairwise t-test. Molecular marker list B might include molecular markers whose data discriminates between a first and third trait subgroup as determined by a second pairwise t-test. Molecular marker list C might include molecular markers whose data discriminates between a first, second and third trait subgroup as determined by ANOVA. In some embodiments, each candidate molecular marker list 60 is preserved as an independent list in candidate molecular marker data structure 58 (FIG. 1).

In some embodiments, processing step 204 identifies a total of between 10 and 4000 candidate molecular markers for any particular training population. In other embodiments, step 204 identifies a total of between 500 and 2000 candidate molecular markers. In yet another embodiments, processing step 204 identified a total of between 100 and 1000 candidate molecular markers.

In some embodiments, some aspects of step 204 are performed by molecular marker candidate identification module 56A. Additionally, there exist known programs that can perform some of the functionality described in step 204. Such programs include those formerly sold by Silicon Genetics (e.g. GeneSpring™); now Agilent Technologies.

In some embodiments, candidate molecular markers identified using the above-described statistical or nonstatistical tests are clustered in order to visualize relationships between the genes. For example, in some embodiments GeneSpring™ is used to perform hierarchical clustering using the Spearman correlation statistic. In some embodiments, QT clustering is used to identify genes that have a similar pattern of expression across the specimens in training population 44. Clustering that can be employed in step 204 is described generally in Section 5.12. Further, Section 5.12 gives examples of some clustering techniques that can be used in step 204. Molecular markers for use in subsequent sections (e.g., for quantitative measurement using methods as described in step 206 below) can be ranked and selected by one or more criteria, including, but not limited to, fold change differences in molecular marker data between two or more trait subgroups, standard deviations of molecular marker data as between two or more trait subgroups using the above-described statistical tests, coefficient of variation, statistical significance (e.g., p-value from ANOVA and/or Mest, or other tests described above), level of expression as determined using molecular marker data, gene function, reproducibility of molecular marker data (includes intra- and inter-experimental), elucidated pathways/networks of the molecular markers as would be understood by a person skilled in the art (e.g. selecting a molecular marker on the basis of an understanding of how said gene is known to function in the body) and the like. Thus in some embodiments, molecular markers for use in subsequent sections are chosen on the basis of the p value identified as a result of step 204 as a measure of the likelihood that the molecular marker data can distinguish as between the two trait subgroups and more particularly molecular markers are chosen wherein the p value is less than 0.5; less than 0.1, less than 0.05, less than 0.01, less than 0.005, less than 0.001, less than 0.0005, less than 0.0001, less than 0.00005, less than 0.00001, less than 0.000005, less than 0.000001 etc. In some embodiments, molecular markers for subsequent steps are chosen on the basis of the level of differential expression displayed by the molecular marker products as between the two or more trait subgroups. Note that in measuring differential fold change in blood, the fold change differences can be quite small, thus in some embodiments, selection of molecular markers is based on a differential fold change where the fold change is greater than 1.2, greater than 1.3, greater than 1.4, greater than 1.5, greater than 1.6, greater than 1.7, greater than 1.8, greater than 1.9, greater than 2.0, greater than 2.1, greater than 2.2, greater than 2.3, greater than 2.4, greater than 2.5, greater than 2.6, greater than 2.7, greater than 2.8, greater than 2.9, greater than 3.0, greater than 3.1, greater than 3.2. greater than 3.3, greater than 3.4 greater than 3.5, greater than 4.0 and the like. In some embodiments, it is helpful to select molecular markers on a basis of the combination of both p value and fold change as would be understood by a person skilled in the art. Thus in some embodiments, molecular markers are first selected as outlined above on the basis of the p value resulting from the molecular marker data and then a subselection of said molecular markers is chosen on the basis of the differential fold change determined from the molecular marker data. In other embodiments, molecular markers are first selected on the basis of differential fold change, and then subselection is made on the basis of p value, In some embodiments, the use of one or more of the selection criteria and subsequent ranking permits the selection of the top 2.5%, 5%, 7.5%, 10%, 12.5%, 15%, 17.5%, 20%, 30%, 40%, 50% or more of the ranked molecular markers for use in subsequent steps. In other embodiments, the selection criteria noted above can be set on the basis of the desired number of selected molecular markers for use in steps 206 and or other steps leading to the selection of the available set of markers for step 214. As would be understood, a selection criteria based on the desired number of selected molecular markers will depend upon the resources available for obtaining the molecular marker data for step 206 and/or the computer resources available for calculating and evaluating classifiers of all or a portion of possible combinations of the selected molecular markers. In some embodiments, the desired number of selected molecular markers for use in step 214 can be 4,000; 3,000; 2,000; 1,000; 900; 800; 700; 600; 500; 400; 300; 200; 190; 180; 170; 160; 150; 140; 130; 120; 110; 100; 90; 80; 70; 60; 50; 40; 30; 20; 10. The more molecular markers which can be selected for use in step 214; the greater the likelihood of identifying classifier or classifiers which are particularly useful for diagnosis.

In some embodiments, one or more subjects of the training population are identified as outliers and are removed prior to identifying individual candidate molecular markers as described herein. These outlier members can then be removed from the training population prior to proceeding to later steps. As described herein, in one embodiment a neural network is used to identify such outliers. A neural network has a layered structure that includes, at a minimum, a layer of input units (and the bias) connected by a layer of weights to a layer of output units. Such units are also referred to as neurons. For output along a single dimension, the layer of output units includes just one output unit. However, neural networks can handle multiple quantitative responses (outputs along multiple dimensions) in a seamless fashion by providing multiple units in the layer of output units.

In multilayer neural networks, there are input units (input layer), hidden units (hidden layer), and output units (output layer). There is, furthermore, a single bias unit that is connected to each unit other than the input units. Neural networks are described in Duda et al, 2001, *Pattern Classification*, Second Edition, John Wiley & Sons, Inc., New York; and Hastie et al, 2001, *The Elements of Statistical Learning*, Springer-Verlag, New York.

The basic approach to the use of neural networks to identify outliers is to start with an untrained network. A training pattern is then presented to the untrained network. This training pattern comprises a training population and, for each respective member of the training population, an association of the respective member with a specific trait subgroup. Thus, the training pattern specifies measured molecular marker data from blood for molecular markers for each member of a training population as well as an indication as to which trait subgroup each member of the training population belongs. In preferred embodiments, training of the neural network is best achieved when the training population includes members from more than one trait subgroup.

In the training process, individual weights in the neural network are seeded with arbitrary weights and then the molecular marker data for each member of the training population is applied to the input layer. Signals are passed through the neural network and the output determined. The output is used to adjust individual weights. A neural network trained in this fashion classifies each individual of the training population with respect to one of the input trait subgroups. In typical instances, the initial neural network does not correctly classify each member of the training population. Those individuals in the training population that are misclassified identify and determine an error or criterion function for the initial neural network. This error or criterion function is some scalar function of the trained neural network weights and is minimized when the network outputs match the desired outputs. In other words, the error or criterion function is minimized when the network correctly classifies each member of the training population into the correct trait subgroup. Thus, as part of the training process, the neural network weights are adjusted to reduce this measure of error. For regression, this error can be sum-of-squared errors. For classification, this error can be either squared error or cross-entropy (deviation). See, e.g. Hastie et al., 2001, *The Elements of Statistical Learning*, Springer-Verlag, New York. Those individuals of the training population which are still incorrectly classified by the trained neural network, once training of the network has been completed, are identified as outliers and can be removed prior to proceeding.

In some embodiments, an ensemble of neural networks can be used on the training population and individuals ranked on the basis of the number of times an individual is misclassified by each neural network. In order to create the ensemble, each neural network can differ with respect to the initial seeded weighting. In another embodiment, each neural network can differ on the basis of randomly generated noise added to the molecular marker data for one or more molecular markers of each individual of the training population added to the input layer. In such an embodiment, this randomly generated noise can be applied by changing the amount of each of the measured molecular marker data of each member of the training population by a scaled random amount. When larger amounts of noise are required, the magnitude of the scaled random amount is increased. In any of these embodiments, the number of layers and the number of units in each layer can be adjusted in order to provide optimal results for any given set of conditions. In this manner, one can identify outliers which are misclassified in as many as 1 0%, 20%, 30%, 40%, 50%, 60%, 70%, 80%, 90% or more of the neural networks used.

Step 205.

Step 205 is optional. We have surprisingly found that certain molecular markers whose molecular marker data fails to discriminate individually as between two trait subgroups in step 204, are still more than incrementally useful when utilized in combinations with other candidate molecular markers selected in step 204. In particular we have been able to identify molecular markers whose data fails to individually discriminate as between two trait subgroups in the pairwise comparison of step 204 but contribute to a classifier identified in step 216 from a combination which includes one or more candidate molecular markers identified in step 204 ("combination friendly molecular markers"). Thus, in order to ensure that molecular markers which may be useful in combinations are not removed prematurely, optional step 205 is performed.

In step 205, all or a portion of the molecular markers for which data has been or can be obtained in at least two of the trait subgroups of the training population are utilized ("putative combination molecular markers"). For purposes of step 205, in one embodiment, the data is obtained using a technique which allows for fast and efficient data generation for all of the molecular markers of the genome of interest chosen. In another embodiment the data is obtained using one or more of the techniques as described in Section 5.3 and/or 5.4. In another embodiment, the data is obtained using microarray technology. In a preferred embodiment, the data used is the data obtained for step 202

In order to identify additional candidate molecular markers, combinations of molecular markers are chosen and a mathematical model applied to the molecular marker data for each molecular marker of the combination resulting in a classifier for each combination. The mathematical model applied can be selected from those defined in Section 5.14. In some embodiments, each possible combination of 2, and/or 3, and/or 4, and/or 5, and/or 6, and/or 7, and/or 8, and/or 9 and/or 10 or more of the putative combination friendly molecular markers are tested. For example, if there are 8,000 putative combination friendly molecular markers, each possible combination of 8 or less molecular markers can be written as follows:

$$8.000!/((8,OQO-8)1(8)!)$$

ach classifier resulting from each combination is scored as described more fully in step 220. In some embodiments, the classifiers are scored using the training population so as to permit time and cost savings. In other embodiments, the classifiers are scored using a scoring population. In yet other embodiments, the classifiers are scored using other resampling or cross validation procedures so as to generate multiple scoring populations. Having scored the classifiers, a subset of classifiers are then selected based on the score.

In some embodiments, the subset of classifiers is any number less than the total number of combinations evaluated. In some embodiments, the top 10%, top 20%, top 30%, top 40%, or top 50% of the classifiers generated are chosen. In some embodiments, wherein scoring is done using ROC area under the curve, those classifiers with an ROC area under the curve of 0.5, 0.6, 0.7, 0.8, 0.9 or 1.0 are selected.

Having selected a number of classifiers, each representing a combination of molecular markers, the number of occurrences of each putative combination friendly molecular marker in the combinations of the selected classifiers are determined. Putative combination friendly molecular markers can then be selected as combination friendly molecular markers so as to used as candidate molecular markers based on the number of reoccurrences of said molecular marker in the selection of combinations evaluated. In one embodiment, 5, 10, 15, 20, 30, 50, 100, 150, 200 or more additional candidate molecular markers not previously selected in step 204 are chosen to proceed to step 206. In other embodiments, the top 10%, top 20%, top 30%, top 40%, or top 50% of combination friendly molecular markers as determined by reoccurrence statistics are selected to be included in the selected set of candidate molecular markers for purposes of choosing combinations to create classifiers in accordance with steps 214 to 218.

Step 206.

In step 206, second molecular marker data is obtained for the candidate molecular markers identified in step 204. In one embodiment, the second molecular marker data is measured using any technique described in Section 5.3 or 5.4 or equivalents thereof. In another embodiment, the same technique used to measure the first molecular marker data in step 202 is used to obtain the second molecular marker data. In other embodiments, an alternative technique is used to measure the second molecular marker data. In other embodiments, the first molecular marker data is obtained using one of the following techniques: microarray, and/or RT-PCR and the second molecular marker data is obtained using any technique but microarray. In other embodiments, the first molecular marker data is obtained using microarray and the second molecular marker data is obtained using any technique except for microarray. The use of second molecular marker data is preferred because the changes in differential expression or abundance of the product of the molecular marker in blood as between trait subgroups can be as low as a 1.1 fold, 1.2 fold, 1.3 fold, 1.4 fold, 1.5 fold etc. which makes less sensitive and reproducible techniques less reliable. In addition, techniques which are preferable for the data collection to allow large scale screening in step 202 such as microarray have been shown to have significant inherent reproducibility issues with high standard deviation as between experiments. As such it is necessary to obtain second molecular marker data so as to ensure the accuracy of the ultimate classifiers identified.

Techniques utilized to obtaining second molecular marker data for the plurality of molecular marker products are those techniques known to measure abundance of RNA and/or protein including the techniques described in Section 5.3 and 5.4.

In some embodiments, it is helpful to obtain a third series of molecular marker data (ie third molecular marker data, fourth molecular marker data etc.) which can be molecular marker data of the training population used in steps 202 or of a different training or scoring population using any known technique including those techniques described in sections 5.3 and 5.4. Preferably more expensive and/or time consuming techniques are used once smaller numbers of candidate molecular markers have been identified In some embodiments, some aspects of step 206 are performed by molecular marker data processing module 11-61. The exact nature of the functionality of molecular processing module 61 will depend on the type of measurement assay used in step 206. However, it is contemplated that module 61 will be used to record measurement values for molecular marker data in a profile similar to molecular marker data processing module I-50, perform any necessary error correction techniques, normalization techniques (e.g., techniques described in Bevington and Robinson, *Data Reduction and Error Analysis for the Physical Sciences*, Second Edition, WCB/McGraw-Hill, 1992, etc.) and/or perform any measurement techniques that can be coded in a digital computer.

Step 208.

Step 208 is optional and allows for the selection of individual candidate molecular markers of step 206 which can be removed prior to the process of selecting and evaluating combinations of molecular markers in steps 214/216. In optional step 208, one or more candidate molecular markers in data structure 58 (FIG. 1) are eliminated. In optional step 208, the same types of tests that were performed in step 204 can be performed. The main difference is that in step 208, the quantitative data measured in step 206 using low throughput methods is used whereas in step 204, the high throughput data measured in step 202 is used. Data measured in step 206 is used in step 208 to validate the candidate molecular markers.

In one specific embodiment, training population 44 consists of a first trait subgroup and a second trait subgroup and step 208 comprises performing a t-test or a nonparametric equivalent of the t-test on each candidate molecular marker using the molecular marker data measured in step 206 to verify for each candidate molecular marker that the molecular marker data differentiates between the first trait subgroup and the second trait subgroup with some measure of statistical confidence. Candidate molecular markers whose molecular marker data are less effective in differentiating between the two trait subgroups (e.g. have a p value that is greater than 0.05) are removed from data structure 58 and are no longer considered as candidate molecular markers.

In another specific embodiment, training population 44 consists of a first trait subgroup, a second trait subgroup, and a third trait subgroup. In this specific embodiment, ANOVA or a nonparametric equivalent is performed independently on each candidate molecular marker in data structure 58 to verify that each molecular marker differentiates between the three subgroups using the molecular marker data. Candidate molecular markers whose molecular marker data are less effective in differentiating between the three trait subgroups (e.g. have a p value that is greater than 0.05) are removed from data structure 58 and are no longer considered as candidate molecular markers.

In some embodiments, each molecular marker is validated by using the data for each molecular marker to generate a Receiver Operating Characteristic (ROC) curve.

ROC curves are generally discussed in Park et al., Korean J. Radiol. 5, p. 11, which is hereby incorporated herein by reference in its entirety. In one embodiment of the present invention, an ROC curve is computed for each candidate molecular marker in training population 44 using the molecular marker data measured in step 206. As noted in step 202, training population 44 includes, for each specimen in the training population, an indication 52 as to whether or not the specimen has a particular trait under study.

Each respective ROC curve graphs the True Positive Fraction (TPF) as compared with 1/the False Positive Fraction (FPF). For example, consider the case in which molecular marker A is being validated and the data for molecular marker A that was measured in step 206 is expression level of the molecular marker A in blood samples from subjects. Table B provides hypothetical values for the abundance of A across training population 44.

TABLE B

Values for molecular marker data of A across training set 44.

| [A] | Presence/Absence of Disease |
|---|---|
| 453 | Y |
| 437 | Y |
| 424 | Y |
| 374 | Y |
| 202 | N |
| 158 | Y |
| 102 | N |
| 37 | N |
| 0.54 | N |

In Table B, each line represents a different specimen in the training population. If the relationship between [A] (data of cellular constituent A) and the presence of disease in subjects in the training population is statistically very significant, all positive results (where specimens have the disease) would be at the top of Table B and all negative results (where biological specimens do not have the disease) at the bottom of the Table B.

To plot the ROC curve corresponding to the test illustrated in Table B, the table is divided into a number of cutoff levels. Then, the sensitivity (TPF) and specificity (TNF) of each cutoff level is computed. Sensitivity and specificity are defined with reference to the decision matrix of Table C.

TABLE C

Decision matrix.

| Test result | True Feature Status | | |
|---|---|---|---|
| | Positive | Negative | Total |
| Positive | TP | FP | T+ |
| Negative | FN | TN | T− |
| Total | D+ | D− | |

In Table C, TP means the number of true positives, FP means the number of false positives, FN means the number of false negatives, and TN means the number of true negatives.

Sensitivity is the proportion of subject with a trait {e.g., a disease or particular biological phenotype) who test positive for the feature. In probability notation sensitivity is $P(T^+|D^+)$ =TP/(TP+FN). Specificity is the proportion of patients without the trait who test negative for the feature. In probability notation specificity is $P(T^-|D^-)$=TN/(TN+FP).

The ROC curve is defined as a plot of the sensitivity as the y-coordinate versus 1-specificity (false positive rate) as the x-coordinate. Thus, for Table B, where each line of the Table B represents an independent cutoff level, the following ROC data points are derived.

TABLE D

ROC data points for Table B.

| Ratio Cutoff Level | Sensitivity | 1-Specificity |
|---|---|---|
| No row | 0 | 0 |
| First row | 0.2 | 0 |
| First two rows | 0.4 | 0 |
| First three rows | 0.6 | 0 |
| First four rows | 0.8 | 0 |
| First five rows | 0.8 | 025 |
| First six rows | 1 | 0.25 |
| First seven rows | 1 | 0.5 |
| First eight rows | 1 | 0.75 |
| First nine rows | 1 | 1 |

Figure 7:
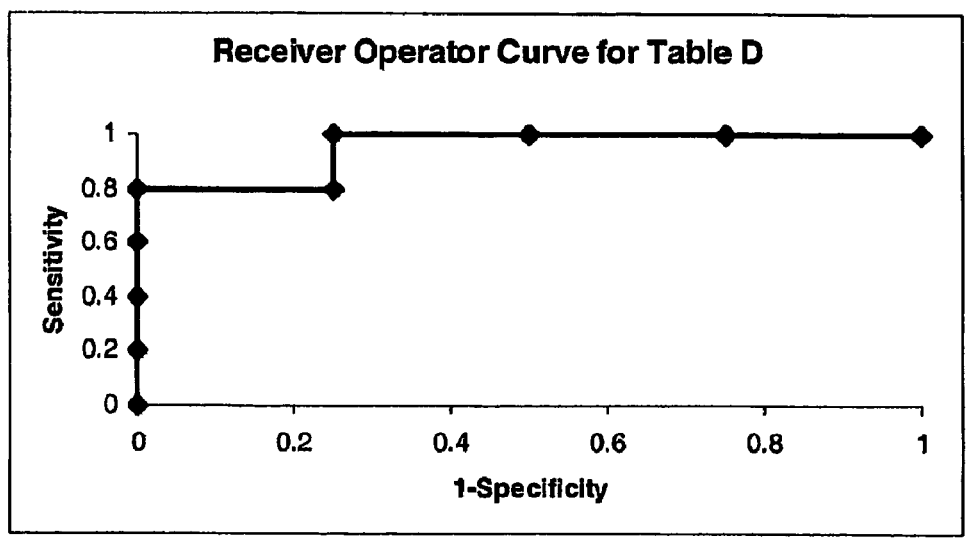
FIG. 7 illustrates a Receiver Operating Characteristic (ROC) curve that is used to assess the discriminating ability of a molecular marker or a classifier in accordance with one embodiment of the present invention.

To compute the last row of Table D, the number of TP, FP, FN, and TN are counted in Table B when the condition is imposed that the classifier predicts that no specimen in Table B is positive for presence of the trait (e.g., disease or a particular biological phenotype). This, of course, is not an accurate classifier as reflected in the respective sensitivity and specificity values of 0 and 1. Plotting sensitivity by 1-specificity yields the coordinate (0,0) as illustrated in the last row of Table D. FIG. 7 illustrates the ROC curve based upon the data points illustrated in Table D. As illustrated in FIG. 7, a ROC curve begins at coordinate (0,0) and ends at coordinate (1,1).

Once an ROC curve has been computed for a molecular marker, in one embodiment, the area under the ROC curve can be quantified. Generally, an area of 1.0 represents a molecular marker that is a perfect diagnostic indicator of the presence of absence of the trait. Preferably an area of greater than 0.5 is desired for a diagnostic indicator, but it will depend upon the trait of interest. For example measurement of protein PSA levels currently used to diagnose prostate cancer has an ROC of 0.47.

In some embodiments there are as many as fifty candidate molecular markers in data structure 58 at this stage of the inventive method. In some embodiments there are more than fifty candidate molecular markers. In practice, the number of candidate molecular markers that remain can be set to any desired number by raising or lowering the criteria for eliminating molecular markers. For example, smaller p values from ANOVA or t-tests, or larger ROC curve areas can be required if the total number of molecular markers is too large. Steps 210 and 212.

Step 210 is optional and allows the additional removal of individual candidate molecular markers of step 206 by evaluating how each individual candidate molecular marker performs within a model which evaluates a combination of molecular markers prior to performing the evaluation of combinations in step 214/216.

In optional step 210 all or a portion of the remaining candidate molecular markers in data structure 58 are used to generate a regression classifier. To compute the regression classifier, measured data from step 206 for the molecular markers in two different trait subgroups in training population 44 are used. In some embodiments, the two different trait subgroups respectively represent a diseased and nondiseased state. In some embodiments, the two different trait subgroups respectively represent a first diseased state (e.g. cancer) and a second unrelated diseased state (e.g., Alzheimer's disease). In some embodiments, the two different trait subgroups represent those subjects that are responsive to drug therapy and those subjects that are not responsive to drug therapy. In still other embodiments, the two different trait subgroups from which molecular marker data is obtained represent data from subjects obtained apriori to treatment, but that have been classified into different trait subgroups on the basis of the ultimate response to treatment. In some embodiments, the two different trait subgroups respectfully represent two different stages of a disease (e.g., moderate versus advanced).

In some embodiments, data for between ten and thirty candidate molecular markers in the two select trait subgroups is used in the logistic regression. In some embodiments, between twenty and one hundred candidate molecular makers in the two select trait subgroups is used in the logistic regression. In still other embodiments, all the candidate molecular markers in the two select trait subgroups are used in the logistic regression.

In step 210 logistic regression can be used because one of the dependent variables is binary—absence or presence of a particular phenotype. For example, consider the case in which molecular marker data from a first trait subgroup and molecular marker data from a second trait subgroup is used in step 210. The first trait subgroup is characterized by a first disease and the second trait subgroup is characterized by a second disease. In such instances, what can be considered by logistic regression is absence or presence of the first disease in subjects. Alternatively, what can be considered by logistic regression is absence or presence of the second disease in subjects.

In general, the multiple regression equation of interest can be written $$Y = a + \beta_1 X_1 + \beta_2 X_2 + \cdots + \beta_k X_k + \epsilon$$

where Y, the dependent variable, is presence (when Y is positive) or absence (when Y is negative) of the trait (e.g., phenotype, condition) associated with the first trait subgroup considered in step 204. This classifier says that the dependent variable Y depends on k explanatory variables (the measured data values for the k candidate molecular markers from subjects in the first and second trait subgroups in training population 44), plus an error term that encompasses various unspecified omitted factors. In the above-identified classifier, the parameter $\beta_1$ gauges the effect of the first explanatory variable $X_1$ on the dependent variable Y, holding the other explanatory variables constant. Similarly, $\beta_2$ gives the effect of the explanatory variable $X_2$ on Y, holding the remaining explanatory variables constant.

In general, in the multiple regression procedure, estimates for $\beta_1$ are obtained by taking into account how uncontrolled changes in other variables influence Y. Thus, in specific embodiments of the present invention, regression is used to eliminate at least some of the candidate molecular markers rather than relying entirely on the tests described in step 208 because the regression takes into account patterns in which multiple molecular markers influence the dependent variable (absence or presence of a trait) in a concerted fashion.

Because the dependent variable data is binary, logistic regression can be used. The logistic regression classifier is a non-linear transformation of the linear regression. The logistic regression classifier is termed the "logit" classifier and can be expressed as $$\ln [p/(1-p)] = cc + \beta_1 X_1 + \beta_2 X_2 + \cdots + \beta_k X_k + \epsilon \text{ or}$$

$$[p/(1-p)] = \exp^\alpha \exp^{\beta_1 X_1} \exp^{\beta_2 X_2} x \ldots x \exp^{\beta_k X_k} \exp^\epsilon$$

where,

In is the natural logarithm, $\log_e$, where $e = 2.71828\ldots$, p is the probability that the event Y occurs, $p(Y=1)$, $(1-p)$, the probability that the event Y does not occur, $p(Y \ne )0$, $p/(1-p)$ is the "odds ratio", $\ln [p/(1-p)]$ is the log odds ratio, or "logit", and all other components of the classifier are the same as the general regression equation described above. It will be appreciated by those of skill in the art that the term for $\alpha$ and $\epsilon$ can be folded into a single constant. Indeed, in preferred embodiments, a single term is used to represent $\alpha$ and $\epsilon$. The "logistic" distribution is an S-shaped distribution function. The logit distribution constrains the estimated probabilities (p) to lie between 0 and 1.

In some embodiments of the present invention, the logistic regression classifier is fit by maximum likelihood estimation (MLE). In other words, the coefficients {e.g., $\alpha$, $\beta i$, $\beta_2$, ...} are determined by maximum likelihood. A likelihood is a conditional probability (e.g., $P(Y|X)$, the probability of Y given X). The likelihood function (L) measures the probability of observing the particular set of dependent variable values $(Y_1, Y_2, \ldots, Y_n)$ that occur in the sample data set. It is written as the probability of the product of the dependent variables:

$$L = \text{Prob}(Y_1 * Y_2 *** Y_n)$$

The higher the likelihood function, the higher the probability of observing the Ys in the sample. MLE involves finding the coefficients ($\alpha$, $\beta i$, $\beta_2$, ...) that makes the log of the likelihood function (LL<0) as large as possible or $-2$ times the log of the likelihood function ($-2LL$) as small as possible. In MLE, some initial estimates of the parameters $\alpha$, $\beta i$, $\beta_2$, . . . are made. Then the likelihood of the data given these parameter estimates is computed. The parameter estimates are improved the likelihood of the data is recalculated. This process is repeated until the parameter estimates do not change much (for example, a change of less than 0.01 or 0.001 in the probability). Examples of logistic regression and fitting logistic regression classifiers are found in Hastie, *The Elements of Statistical Learning*, Springer, N.Y., 2001, pp. 95-100, which is hereby incorporated by reference in its entirety.

Step 212.

In specific embodiments, all or a portion of the candidate molecular markers are used and the molecular marker data fit using logistic regression. Then, in a stepwise fashion, some of the molecular markers are eliminated from the classifier using backward stepwise regression. Backward stepwise regression begins with a full or saturated classifier and variables are eliminated from the classifier in an iterative process. The fit of the classifier is tested after the elimination of each variable (molecular marker) to ensure that the classifier still adequately fits the molecular marker data. When no more variables can be eliminated from the classifier or a desired number of molecular markers remain in the classifier, the analysis has been completed. In specific embodiments, the regression applied in step 210 is used to refine the candidate molecular marker list to less than 25, less than 24, less than 23, less than 22, less than 21, or less than 20 molecular markers.

In one embodiment, a logistic regression classifier is computed using all or a portion of the available candidate molecular markers in data structure 58. Then, coefficients are tested for significance for inclusion or elimination from the classifier using a Wald test, a likelihood-ratio test (chi-squared statistic), a Hosmer-Lemshow Goodness of Fit Test, or the like. For example, the likelihood-ratio test uses the ratio of the maximized value of the likelihood function for the full classifier ($L_1$) over the maximized value of the likelihood function for the simpler classifier ($L_0$) in which one or more molecular markers have been removed. The likelihood-ratio test statistic equals:

$$-2\log\left(\frac{L_0}{L_1}\right)$$

This log transformation of the likelihood functions yields a chi-squared statistic.

Step 213.

Step 213 is optional. We have found that performing optional step 213 provides a significant improvement in identifying classifiers which are particularly useful in diagnosis of a disease or condition of interest. In optional step 213, clinically measurable parameters are identified which are thought to be relevant to the trait of interest for which a classifier is desired. For example, where the trait of interest is prostate cancer, clinically measurable parameters chosen are those that are known or are shown to be relevant to the trait of interest. For example in one embodiment, clinically measurable parameters relevant to prostate cancer can include age of subject, level of prostate specific antigen (PSA); and volume of prostate. In yet another embodiment, where the trait of interest is osteoarthritis, some relevant clinically measurable parameters are age and body mass index (BMI). The selected clinically measurable parameters are then included as part of the "selected set of candidate molecular markers" and are treated as molecular markers for the purpose of selecting combinations and developing classifiers in step 214 through 218 as described below.

In order to treat the clinically measurable parameter as a molecular marker for purposes of step 214 through 218, the clinically measurable parameter must have associated data. In some embodiments, where the clinically measurable parameter is one which has an associated value—for example age, blood glucose level, PSA level, blood pressure, body mass index, etc., the value can be treated as the molecular marker data for purposes of steps 214 through 218. In some embodiments there is no value associated with the clinically measurable parameter, for example where the relevant clinical parameter is determinable but does not provide a value. In those cases, a value can be assigned to represent each aspect of the clinically measurable parameter. For example where the sex of a person is the clinically measurable parameter, a value of 1 can be assigned to represent that the person is male, and a value of 0 can be assigned to represent that the person is female. As yet another example, where the relevant clinically measurable parameter is ethnicity, a different value can be assigned to each ethnicity (e.g. 1 Caucasian, 2 asian, 3 ashkanazi jew etc. and said value can be used as the molecular marker data associated with ethnicity for purposes of step 214 through 218.

Step 214.

Steps 214 through 218 provide an approach in which all or a portion of the possible combinations of the selected set of candidate molecular markers resulting from steps 202-213 are chosen. Molecular marker data from each candidate molecular marker in a elected combination is applied to a mathematical model as described more fully in Section 5.14. If there are N selected molecular markers at this stage then, in some embodiments, as many as 2N−1 different combinations can be selected and classifiers can be computed for each of these combinations. For example, consider the case in which three molecular markers are selected after any combination of steps 201 through 212 have been performed and logistic regression is used in step 216. In this case, the following 2³−1 mathematical models can be used to form 2³−1 corresponding classifiers:

$$\ln[p/(1-p)] = a + \beta_1 X_1 + \beta_2 X_2 + \beta_3 X_3 + \epsilon$$

$$\ln[p/(1-p)] = \alpha + \beta_1 X_1 + \beta_2 X_2 + \epsilon,$$

$$\ln[p/(1-p)] = a + \beta_x X_x + \beta_3 X_3 + \epsilon,$$

$$\ln[p/(1-p)] = \alpha + \beta_2 X_2 + \beta_3 X_3 + \epsilon,$$

$$\ln[\rho/(1-\rho)] = \alpha + \beta_1 X_1 + \epsilon_5$$

$$\ln[p/(1-p)] = tf + \beta_2 X_2 + \epsilon, \text{ and}$$

$$\ln[p/(1-p)] = a + \beta_3 X_3 + \epsilon.$$

In these mathematical models, α, βi, β₂, ..., $\beta_N$ represent coefficients that are regressed against molecular marker data whereas $X_1, X_2, \ldots, X^N$ each represent a different RNA or protein (or more generally, a molecular marker) for which molecular marker data is available. In some embodiments any one of elements $X_1, X_2, \ldots, X^N$ can represent a clinically measurable parameters. In a preferred embodiment for each combination chosen, at least one of the molecular markers of the series Of $X_1, X_2, \ldots, X^N$ does not represent a clinically measurable parameter. In some embodiments, additional interaction terms are also considered, producing non linear behaviour and resulting in greater than or less than as $2^{N-1}$ different combinations. In some embodiments, additional interaction terms are also considered, producing non linear behaviour. For instance, in the example above, another mathematical model to which molecular marker data can be applied in order to form a classifier is:

$$\ln[p/(1-p)] = \alpha + \beta_2 X_2 + \beta_3 X_3 + \beta_4 X_a X_3 + \epsilon$$

where the coefficient β₄ represents the interaction between molecular marker $X_2$ and $X_3$. In such embodiments, more than $2^N-1$ "combinations" and thus more than $2^N-1$ classifiers are considered. In addition to the possibility of interaction terms, the present invention encompasses nonlinear variables. Examples of nonlinear variables include variables that are squared, squared rooted, or in fact, taken to any power. For instance, additional examples of mathematical models to which molecular marker data can be applied include:

$$\ln[p/(1-p)] = a + \beta_2 (X_2)^2 + \beta_3 X_3 + \beta_4 X_2 X_3 + \epsilon$$

$$\ln[p/(1-p)] = \alpha + \beta_2 (X_2)^{1/2} + \beta_3 X_3 + \beta_4 X_2 X_3 + \epsilon$$

In some embodiments, a logarithmic or exponential function is applied to one or more of the variables. In some embodiments, ratios of molecular marker data can be used as a mathematical model. For example, consider the case in which regression is used to apply molecular marker data to the following equation in order to develop a classifier:

$$\ln[p/(1-p)] = a + \beta_e X_1 + \beta_2 X_2 + \beta_3 X_3 + \epsilon$$

Above, it was noted that $X_1, X_2, \ldots, X_N$ each represent the product of a different gene (or more generally, a molecular marker or molecular marker like element) for which molecular marker data is available. However, in the case where ratios are selected for use in mathematical models which are subsequently scored, each $X_1, X_2, \ldots, X_N$ can in fact represent a ratio of abundance and/or expression levels for two different molecular marker products e.g. RNA or proteins, or any other type of molecular marker. For example, $X_1$ can represent the ratio between molecular marker data measured in step 206 representative of gene (molecular marker) A and data for gene B in training population 44. Mixed forms of mathematical models are also possible. For example, some variables X can represent ratios between the molecular marker data of two molecular markers whereas other variables X can represent molecular marker data of discrete molecular markers as opposed to ratios of molecular marker data. In one specific embodiment a "ratio" of the RNA products of two molecular markers can be used and all or some of the possible combinations of said "ratios" can be utilized. For example, where the molecular marker data is a measure of abundance of RNA is determined using quantitative RT-PCR, the measure of the expression level of gene (molecular marker) A and the measure of the expression level of gene B can be used as a single term. In some embodiments this is done by first determining the level of expression of each gene individually as compared with an internal housekeeping control such as β-actin:

$$\text{e.g. } \Delta Ct = Ct\text{gene}A - Ct\beta\text{actin}$$

where CtgeneA is the threshold cycle of amplification of GeneA and Ctβactin is the threshold cycle of amplification of the internal control β-actin. Similarly the level of expression of gene B is also determined in comparison with an internal housekeeping control $$\text{e.g. } \Delta Ct = Ct\text{gene}B'' Ct\beta\text{actin}$$

In order to combine the terms into a single term for purposes of creating a classifier using "ratios" of the two terms—the terms are combined as follows to form a single variable (e.g. X).

$$\Delta Ct = Ct\text{gene}A - Ct_{gene}B$$

This is commonly described as the use of ratios given the logarithmic nature of the measure of Ct. Thus in some embodiments, the $X_1, X_2, \ldots, X_N$ of a classifier, each term represents the "ratio" of two molecular markers. In other embodiments the Ct scores are compared directly rather than compared with an internal control.

For example, consider the case in which the desire is to form a classifier that discriminates between a first trait subgroup and a second trait subgroup wherein each term of the classifier represents molecular marker data which is derived from a combination of molecular markers using ratios as outlined above (e.g. $\Delta Ct = Ct_{geneA} - Ct_{geneB}$)—In such a case, each variable actually represents two molecular markers—the ratio of the molecular marker data for two molecular markers. Therefore in instances, for example, where 10 molecular markers have been identified by the funneling process of steps 202-210, 45 possible combinations of "ratios" of molecular markers can be formed $$e.g. \frac{n!}{(n-2)!2!}$$

where n is the number of possible molecular markers (e.g. 10).

In some embodiments it is particularly useful to select molecular markers where the molecular marker data will work well in the form of a "ratio" thus, as part of step 214, in one embodiment, prior to selecting combinations of molecular markers, molecular markers whose molecular marker data can be combined as ratios are first identified.

The use of molecular marker data as variables in which the variable representing the product of the molecular marker is in the form of ratios or raised to some arbitrary power {e.g., $\alpha$, 2, N, etc.) is not limited to mathematical models based on regression. Such variables can be used in any of the mathematical models described herein (e.g., neural networks). For example, consider the case in which the desire is to form a classifier that discriminates between a first trait subgroup and a second trait subgroup wherein each term of the classifier is a combination of molecular markers evaluated as a ratio. In step 214, in one embodiment, prior to selecting ratios of molecular markers, molecular markers which can be combined as ratios are first identified. Molecular markers which can be combined as ratios are those molecular markers wherein the ratio as between said molecular markers is a value which is not equal 11.0 (or in one embodiment wherein $\Delta Ct = Ct_{gene\,A} - Ct_{gene\,B}$ does not equal zero. In one embodiment, a first set of molecular markers and a second set of molecular markers are selected to create ratios such that the first set of molecular marker data demonstrates the molecular marker is upregulated in the first trait subgroup (relative to the second trait subgroup) in training population 44 and a second set of molecular marker data demonstrates that the molecular marker is downregulated in the first trait subgroup in training population 44 (relative to the second trait subgroup). Thus, for example an upregulated gene is one in which $\Delta Ct = Ct_{gene}$ B-$Ctp_{ac}tin > 0$ and a downregulated gene is one in which $\Delta Ct = Ct_{gen}eA - Ctpactin < 0$, Here, the term upregulated or downregulated generally means that such up or down regulation is observed in the training population with some measure of statistical confidence, for example a Mest having ap value of 0.05, less than 0.01, less than 0.005, less than 0.001, less than 0.0005, less than 0.0001, less than 0.00005, less than 0.00001, or less. Then, ratios of molecular markers can be formed using one molecular marker from the first set and a second molecular marker from the second set.

In another embodiment, a ratio for use in a selected combination is one in which the numerator represents the molecular marker data that demonstrates the molecular marker is upregulated in a first trait subgroup (as compared with a second trait subgroup) and the denominator represents the molecular marker data that demonstrates the molecular marker is upregulated in a second trait subgroup (as compared with a first trait subgroup). With such a ratio, a value greater than "1" indicates that the organism from which the molecular marker data was measured is a member of the first trait subgroup whereas a value less than "1" indicates that this organism is a member of the second trait subgroup. Thus, in some embodiments, step 214 comprises obtaining combinations of ratios of molecular marker data. In some embodiments, step 214 comprises obtaining some multiple of molecular markers and forming a plurality of ratios of the molecular marker data so as to generate a plurality of combinations of molecular markers.

In step 214, a combination of molecular markers is selected. In some embodiments, this combination of molecular markers consists of a single molecular marker. In some embodiments, this combination of molecular markers comprises 2, 3, 4, 5, 6, 7, 8, 9, 10, 11, 12, 13, 14, 15, 16, 17, 18, 19, 20, as many as 30, as many as 40, as many as 50 or more molecular markers. In some embodiments, this combination of molecular markers consists of a combination of ratios of molecular markers wherein the combination comprises 2, 3, 4, 5, 6, 7, 8, 9, 10, 11, 12, 13, 14, 15, 16, 17, 18, 19, 20, as many as 30, as many as 40, as many as 50 or more molecular markers. For each candidate molecular marker added, the number of possible combinations grows exponentially. The limitation to the number of combinations selected for evaluation is dependent upon the capacity of the computer, network of computers or supercomputers utilized. In one embodiment, all possible combinations of molecular markers resulting from steps 202-213 (or resulting from some subset of steps 202-213) are chosen. In another embodiment, all possible combinations of ratios of molecular markers resulting from steps 202-213 (or resulting from some subset of steps 202-213) are chosen. In another embodiment, one can subject all possible pairs of candidate molecular markers; all possible combinations of three molecular markers, all possible combinations of four molecular markers; all possible combinations of five molecular markers, all possible combinations of six molecular markers, all possible combinations of seven molecular markers etc. In another embodiment, all possible combinations of two sets of ratios are chosen, in another embodiment, all possible combinations of three sets of ratios are chosen, in another embodiment, all possible combinations of four sets of ratios are chosen, in another embodiment, all possible combinations of five sets of ratios are chosen. Each of the combinations of molecular markers is evaluated in subsequent processing steps.

Step 216.

In step 216, a classifier is computed using each combination of molecular markers chosen in the last instance of step 214 and by applying the classifier to the molecular marker data measured for each molecular marker of this combination of molecular markers to a mathematical model, such as the mathematical models defined in Section 5.14 resulting in one or more classifiers for each combination. As described more thoroughly in Step 204, in some embodiments, one or more subjects of the training population are identified as outliers and are removed prior to computing classifiers for each combination of molecular markers chosen.

In order to compute a classifier, in some embodiments, the mathematical model is a regression model, a neural network, a clustering model, principal component analysis, nearest neighbor classifier analysis, linear discriminant analysis, quadratic discriminant analysis, a support vector machine, a decision tree, a genetic algorithm, classifier optimization using bagging, classifier optimization using boosting, classifier optimization using the Random Subspace Method, Bayesian Networks (see F. V. Jensen. "Bayesian Networks and Decision Graphs". Springer. 2001, which is incorporated herein by reference in its entirety), a projection pursuit, weighted voting, a ratio or combination of ratios, or any combination of the above. Representative mathematical models that can be used in the present invention are described in Section 5.14. In the case where the mathematical model is a ratio or combination of ratios, steps 214 and 216 involve using the low throughput molecular marker data from training population 44 that was measured in step 206 to determine which molecular markers should be in the numerator of the ratios and which molecular markers should be in the denominator of the ratios. In some embodiments, the mathematical model used comprises a plurality of ratios of the molecular marker data. In such embodiments, the molecular marker data used in the numerators of the plurality of ratios can be the same or different than the molecular marker data used in the denominators of the plurality of ratios. In other words, a given molecular marker can be represented in the numerator of more than one ratio in the plurality of ratios or represented in the denominator of more than one ratio in the plurality of ratios.

Step 218.

In optional step 218 a determination is made as to whether all of the possible desired combinations of molecular markers to be tested have been considered. As discussed above in step 214, all or a portion of possible combinations may be tested. If not (218—No) process control returns to step 214 where another combination of molecular markers is selected and, at step 216, this new combination of molecular markers is evaluated using a mathematical model applied to the molecular marker data of the new combination. In some embodiments, the candidate molecular marker list comprises less than 25, less than 24, less than 23, less than 22, less than 21, or less than 20 molecular markers at step 214. In some embodiments, step 218 requires that a classifier be computed for all possible combinations of molecular markers. In other embodiments, step 218 requires that classifiers for only a portion of the possible combinations of molecular markers be considered.

In some embodiments, some aspects of steps 214-218 are performed by molecular marker classifier evaluation module 62. In fact, in some embodiments, several different software programs, such as Microsoft (Redmond, Wash.) Excel, are used in steps 214-218.

Step 220.

Once all the desired classifiers have been computed by loop 214-218, the classifiers are evaluated to determine which of the classifiers are most effective. In one embodiment the resulting classifiers of loop 214-218 are scored. In some embodiments, scoring is done using the training population 44. In other embodiments, scoring is done using a "scoring population" wherein the scoring population includes at least some members not present in the training population. In one embodiment, the scoring population includes members of the training population in addition to one or more members not used in the training population. In some embodiments, five percent or less, ten percent or less, twenty percent or less, thirty percent or less, fifty percent or less, or ninety percent or less of the members of the training population are common to the scoring population.

In some embodiments, the Percent Correct Predictions statistic is used to score each classifier. The "Percent Correct Predictions" statistic assumes that if the estimated p is greater than or equal to 0.5, then the event is expected to occur and to not occur otherwise. By assigning these probabilities zeros and ones, a comparison can be made to the values of the samples in the training population to determine what percentage of the training population was sampled correctly.

In some embodiments, ROC analysis is performed and is used to score the classifiers. In one embodiment, the area under the ROC curve is used to judge the quality of the classifier. As would be understood by those of skill in the relevant arts, area under the curve converts the two dimensional information contained in the ROC curve into one dimensional information. In other embodiments, information from the two dimensional aspect of the ROC curve is utilized directly. For example, the ROC curve also provides information with respect to the sensitivity and specificity of the classifier. In some embodiments, classifiers are selected on the basis of either sensitivity or specificity. This can be an important scoring indicator. For example, a diagnostic classifier with high sensitivity (ie high true positive rate and low false negative rate may be important in situations where it is safer to misdiagnosis an individual as having disease rather than misdiagnosing a disease bearing person as normal. Therefore in some embodiments, a cutoff can be set for either sensitivity or specificity and the classifier ranked or scored on the basis of the remaining variable. In some embodiments, ROC curves are generated for each model computed in an instance of step 216 using data obtained in step 206 for members of either the training population or scoring population or both.

In some embodiments, the classifier resulting from the application of the mathematical itself results in a score as to the accuracy of the model. In this embodiment, the score is based on the accuracy of the model within the training population only.

In some embodiments, a classifier is a weighted logistic regression model characterized by a multicategory logit model. For example, in some embodiments, a classifier discriminates between two different trait groups. In other embodiments, a classifier discriminates between more than two different trait groups. Logit models, including multicategory logit models are described in Agresti, *An Introduction to Categorical Data Analysis*, John Wiley & Sons, Inc., 1996, New York, Chapters 7 and 8, which is hereby incorporated by reference. Table E illustrates the data that is used to form an ROC curve based on expression data applied to a mathematical model that uses the logit:

TABLE E

Values for the logit $\ln[p/(1-p)] = \alpha + \beta_1 X_1 + \beta_2 X_2 + \epsilon$
using hypothetical values for training population 44

| $\ln[p/(1-p)]$ | Presence/Absence of a Trait |
| --- | --- |
| 0.98 | Y |
| 0.97 | Y |
| 0.95 | Y |
| 0.93 | Y |
| 0.91 | N |
| 0.11 | Y |
| 0.07 | N |
| 0.03 | N |

Each row in Table E corresponds to a different specimen in the scoring population. The left column represents the results of the logit for the classifier being sampled. The specimens in Table E are ranked by the logit score listed in the left hand column. The right hand column details the presence or absence of the trait that is being considered by the regression equation. Table E can be used to compute a ROC curve using the same techniques disclosed in step 208 (in which each row in Table E is considered a threshold cutoff value in order to compute ROC curve datapoints). Then, the area under the ROC curve can be computed in order to assess the predictive quality of the classifier.

In step 220, each classifier is scored using any of the techniques disclosed here or that are known in the art. The classifiers can then be ranked based on their score. For example, they can be ranked based on the percent correct predictions, area under the ROC curve, sensitivity or specificity or some weighted or unweighted combination of the two scoring techniques. In some embodiments, step 220 is performed by molecular marker evaluation module 64.

Step 222.

Step 222 is optional. Optional step 222 provides additional filtering to eliminate some of the candidate classifiers computed in loop 214-218. In one such filter, limited to the case in which the classifiers computed in steps 214-218 are based on application of data to regression based mathematical models, classifiers that have at least one coefficient that is large are eliminated. Such classifiers have the potential to magnify small errors in the data. In some embodiments, determination as to whether or not a coefficient is large can require multiple computation steps. In instances where a coefficient uniquely represents a molecular marker, the maximum value (MAX) for the data measured for the molecular marker in a trait subgroup associated with the classifier is identified. For example, consider the case in which a given coefficient uniquely represents the expression of gene A in blood. Further suppose that low throughput data for gene A from 10 individuals of a particular trait subgroup was measured in step 206. The value MAX would be the largest expression value observed for gene A in the ten individuals from the subject trait subgroup. For example, if individual #7 in the set of ten individuals exhibited the highest expression level for gene A as determined by the methods of step 206, then the expression value measured for gene A in individual #7 will represent MAX. Next, the minimum value (MIN) for the data measured for the molecular marker in the subject trait subgroup is identified. In the example presented above, MIN is the expression level of gene A in the subject having the lowest expression level for gene A in the set of ten subjects as determined by the low throughput measurement methods of step 206. Next, the coefficient derived in the regression for the unique molecular marker (e.g., the coefficient for gene A) is multiplied by the difference between (MAX) and (MIN) in order to obtain the test value (TEST). In other words, for each coefficient/in a classifier, the following equation is computed:

$$TEST_i = coefficient_i * [MAX-MIN].$$

As an example, consider the case in which a classifier is used to determine whether or not a subject has a particular cancer. In this case, one of the trait subgroups in training population 44 will represent patients that have this cancer. To evaluate a coefficient of a classifier in this case, the low value and high value for the measured data of the molecular marker i in the trait subgroup is obtained and the difference between these two values is multiplied against the coefficient value in order to obtain the value of TEST. In some embodiments, a coefficient/is considered large and the classifier that includes the coefficient is discarded when the value is greater than 5, greater than 10, greater than 100 or greater than 1000.

In typical embodiments, a classifier will determine whether a subject falls into one of at least two different trait subgroups. In other words, the classifier will discriminate between at least two different trait subgroups. A test has been presented above for determining whether a coefficient in a regression derived classifier is too large. This test used one of the trait subgroups that the classifier discriminates. In some embodiments, the test is repeated for each of the trait subgroups that the classifier can discriminate. For example, in the case of a classifier that can discriminate between the cancerous trait subgroup and the non-cancerous trait subgroup, the test is independently run using data from each trait subgroup. That is, the test is first run using only data from the cancerous trait subgroup and then the test is run a second time using only data from the non-cancerous trait subgroup. If a coefficient is too large in any such independent test, the classifier is eliminated from further consideration. In some embodiments, the test is run against only one of the possible trait subgroups that the subject classifier can discriminate.

In another embodiment, some classifiers are eliminated on the basis of the score. For example, where the scoring system used is receiver operating characteristic (ROC) curve score determined by an area under the ROC curve, in some embodiments, those classifiers with scores of less than 0.95, 0.9, 0.85, 0.8, 0.7, 0.65, 0.6, 0.55 0.5 or 0.45 or less can be eliminated. In other embodiments, where specificity is important to the use of the classifier, a sensitivity threshold can be set and classifiers ranked on the basis of the specificity. for example with a cutoff for specificity of less than 0.95, 0.9, 0.85, 0.8, 0.7, 0.65, 0.6, 0.55 0.5 or 0.45 or less can be eliminated. Similarly, the specificity threshold can be set and classifiers ranked on the basis of sensitivity for example with a cutoff for sensitivity of less than 0.95, 0.9, 0.85, 0.8, 0.7, 0.65, 0.6, 0.55 0.5 or 0.45 or less can be eliminated. Thus in some embodiments, only the top 10 ranking classifiers, the top 20 ranking classifiers, or the top 100 ranking classifiers are selected and the remaining classifiers eliminated.

Step 224.

After classifiers have been scored and ranked and some classifiers optionally eliminated; one or more classifiers can be combined to create a classifier group. For instance, in some embodiments, the top 10 ranking classifiers, the top 20 ranking classifiers, or the top 100 ranking classifiers are selected. In some embodiments, any of the top 1 to top 500 ranking classifiers is selected. In instances where more than one classifier is selected, in one embodiment, each classifier contributes one vote to the diagnosis of the test subject such that diagnosis of the test subject is determined as a result of a combination of classifiers. In other embodiments, multiple classifiers can be used and different weighting schema applied to each classifier. For example, weighting schema can include weighting on the basis of factors such as the original score the classifier, the logs odd ratio ("logit"), the size of the coefficients for each classifier, some combination thereof and the like.

Step 226.

Step 226 is optional. Optional step 226 is useful if training population 44 is comprised of more than two trait subgroups. In cases where there are more than two trait subgroups, multiple binary classifiers (or groups of said classifiers) can be developed wherein each binary classifier (or group of said classifiers) is directed towards differentiating as between two traits. In one embodiment, each round of the funnel (e.g. steps 202, 204, 206, 214, 216, 220 and 224) produces a set of binary classifiers. In another embodiment, multiple lists of binary candidate molecular markers are developed by performing step 202, and then binary classifiers (or groups of binary classifiers) are developed by proceeding with multiple rounds of the remainder of the funnel (e.g. steps 204, 206, 214, 216, 220 and step 224). Because each classifier represents only a binary test e.g. the absence or presence of a single trait, in step 226 a determination is made as to whether all classifiers have been developed for training population 44. If not (226—No), process control returns to step 210 and work is initiated to develop a classifier for a different trait represented by training population 44. Therefore, steps 210-224 can optionally be repeated until one or more classifiers or groups of classifiers have been selected for each of the trait subgroups represented by training population 44.

In some embodiments, each classifier or group of classifiers developed in accordance with embodiments of the present invention is stored in classifier database 70. FIG. 5 illustrates an exemplary classifier database 70 in accordance with one embodiment of the present invention. Database 70 includes an entry 400 for each classifier 400. Each classifier 400 is optionally given a classifier name 402. Each classifier 400 is part of classifier. For example, a given classifier can consist of only a single classifier. In other embodiments, a given classifier can consist of one or a plurality of classifiers. Therefore, each classifier 402 includes an indicator 403 to indicate which classifier the classifier is in. Further, each classifier 400 has an optional indicator 404 to indicate the trait that the classifier can discriminate. In some embodiments, optional indicator indicates the trait subgroups that the classifier can discriminate. In some embodiments such information can be inferred from the classifier identifier field 403 since each classifier represents the absence or presence of a particular trait (e.g., absence or presence of cancer). In addition to this header information, each classifier includes the identity 406 of one or more molecular markers and the respective coefficients 408 for each of the molecular markers.

Figure 3:
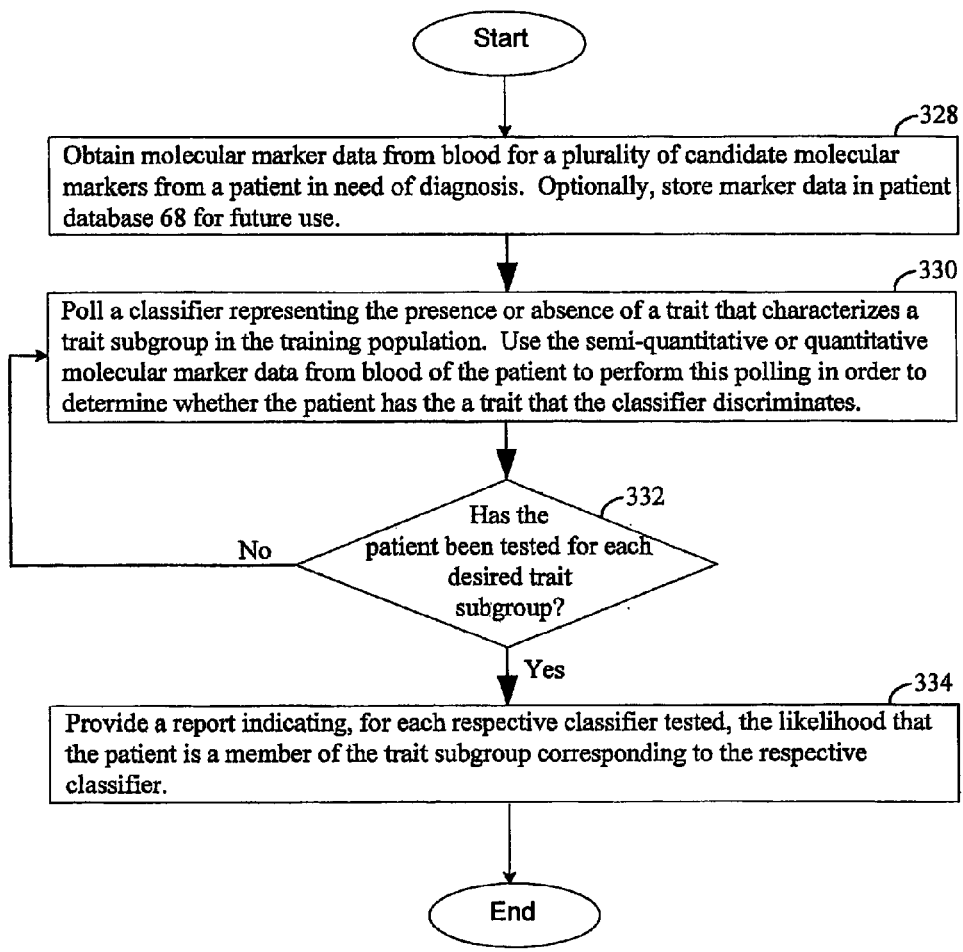
FIG. 3 is a flowchart of a method of applying the classifiers to a patient.

Once classifiers or classifier groups have been developed, the classifiers can be used to diagnose a patient that has presented as possibly having a disease that can be differentiated by the classifiers. FIG. 3 is a flowchart of a method of applying the classifiers to a patient.

Step 328.

Step 328 can be performed after the previously described steps, or can be used in conjunction with a classifier or classifier groups derived using the methods disclosed herein. As such, steps 328-334 represent a completely independent method of the present invention and can be performed at any time once suitable classifiers have been developed using, for example, steps 301 through 326. Step 328 is used in conjunction with step 330 to diagnose a trait of interest of an individual not represented in either the training population or the scoring population (a "test individual"). Each classifier or classifier group identified previously can be used to determine whether a test individual has a trait of interest. In order to perform such tests, molecular marker data for each molecular marker of the classifier or classifier group of interest is required. To obtain such data, a sample of blood from the subject is obtained using any of the techniques described in Section 5.2. The sample is used to measure molecular marker data for each molecular marker in the sample using any of the techniques described in Sections 5.3 or 5.4. Thus in step 328, once classifiers have been identified, molecular marker data for use with the classifier or classifier groups can be obtained using either high throughput or low throughput techniques.

Advantageously, the molecular marker data obtained in step 328 can be stored in patient database 68 for later use. In fact, in some embodiments, rather than obtaining molecular marker data from a patient sample in step 328, the data is obtained from a subject in patient database 68. In such embodiments, the molecular marker data was previously loaded into patient database 68.

Figure 6:
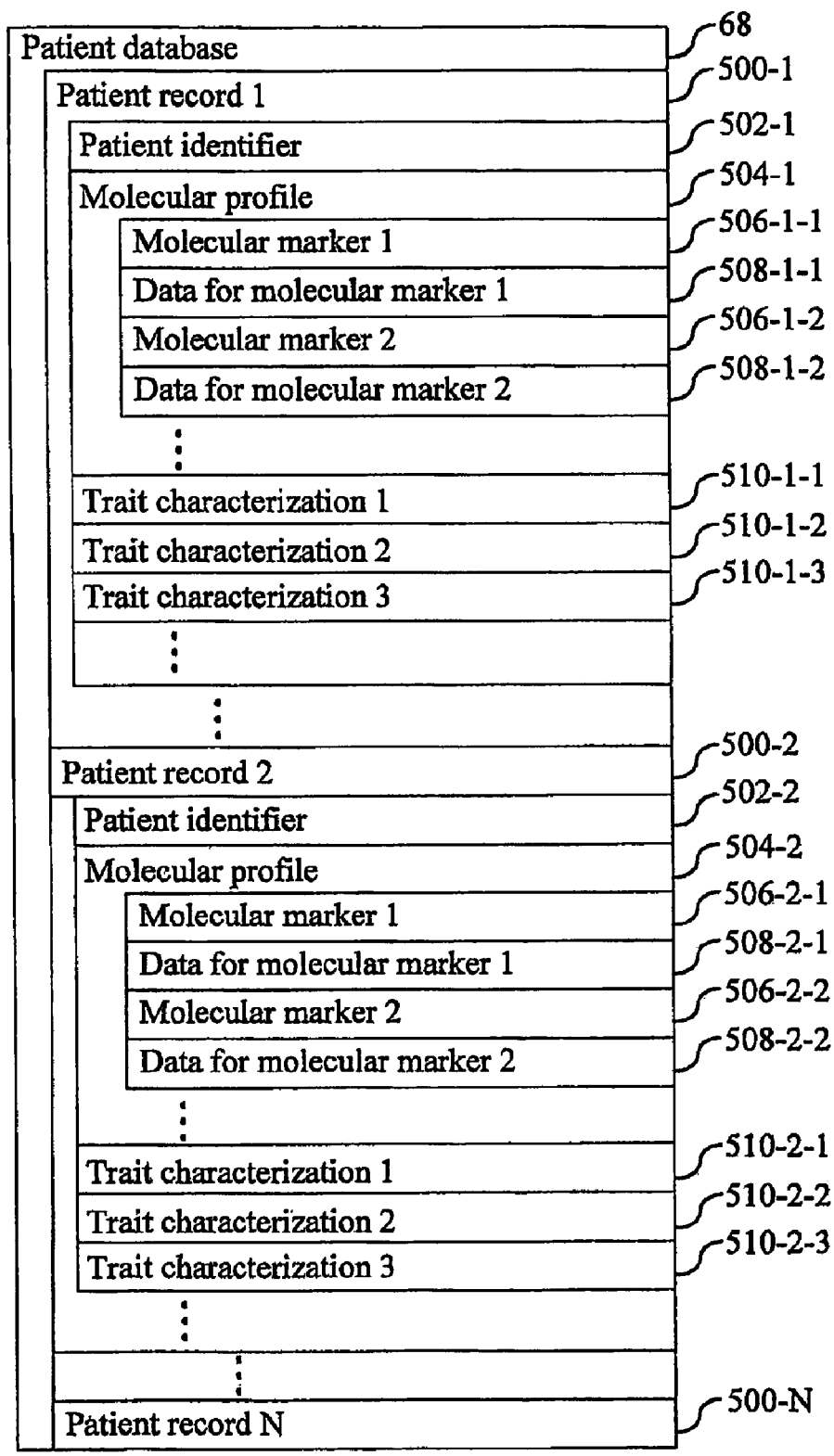
FIG. 6 illustrates a patient database for storing data for molecular markers for a plurality of patients in accordance with an embodiment of the present invention.

FIG. 6 illustrates a patient database 68 in accordance with one embodiment of the present invention. There is a record 500 for each patient (subject) tracked by patient database 68. Each patient record 500 optionally includes a patient identifier 502 to uniquely identify the patient. In some embodiments such unique identifiers can be inferred from the patient record value 500. Each patient record 500 includes a molecular profile 504 comprising molecular marker data collected for a plurality of molecular marker products from a sample defined in Section 5.2 using any one of the techniques described in Sections 5.3 and 5.4. In typical embodiments, a molecular profile 504 includes a plurality of molecular marker identities 506 and the corresponding measured molecular marker data values 508 for such molecular markers. In addition to the molecular profile, each patient record 502 can include one or more traits 510. Such trait characterizations can be assigned by observation of the subject and/or by testing the patient's molecular profile using the classifiers constructed in accordance with the methods of the present invention. Section 5.10, below, provides more details on exemplary patient databases 68.

Step 330.

In step 330 the classifier created using some or more of the previous steps is used to diagnose a test individual. In some embodiments diagnosis can be performed using a classifier group from step 224. For example, in one embodiment, where there are numerous classifiers after step 222 that provide satisfactory scores (given the purpose for use), a test subject can be diagnosed by using the results of all or some of these classifiers in the form of a classifier group as described in step 224. In one embodiment, the term diagnosis means the results of a single classifier or group of classifiers resulting from the application of the funneling method described in steps 202-224. For example, the resulting classifier or group of classifiers will enable the ability to determine whether a test individual belongs to one of two possible trait subgroups. In another embodiment, by the term diagnosis is meant the results of multiple classifiers or multiple groups of classifiers (ie classifiers resulting from the application of more than one round of the funneling method described in steps 202-224). For example, the resulting classifiers or groups of classifiers used in series can allow a diagnosis as to whether an individual belongs to one of three or more possible trait subgroups (e.g. results of first classifier distinguish as to whether person has schizophrenia or does not have schizophrenia—If not schizophrenia apply a second classifier or group of classifiers to determine whether individual has bipolar disorder or does not have bipolar disorder etc.) The use of the classifiers to diagnose depends upon the trait subgroups used to develop the classifier. For example, if the classifier was developed to differentiate as between two trait subgroups, the classifier can be used to diagnose a test subject as being either of the first trait subgroup or the second trait subgroup. To diagnose a test subject, preferably a quantitative technique such as quantitative RT-PCR is utilized to obtain molecular marker data measured in step 328 is used.

To illustrate the use of a classifier to diagnose, consider the case in which the classifier comprises the classifier group:

$$\ln [p/(1-p)] = 0.34 + 0.24 JT_1 + 0.74 X_3 + 0.03,$$

$$\ln [p/(1-p)] = 0.54 - OAST_2 + 83 X_3 + 0.01.$$

That is, the exemplary classifier group consisting of two classifiers. To poll the classifier, the data (e.g. abundance level, activity level, etc) for molecular markers $X_1$, $X_2$ and $X_3$ is measured using any of the techniques described in Section 5.3 or 5.4. Then, these data measurement values are placed into the classifier equations and the equations are processed and the output is used to predict outcome In one embodiment, classifier equation values that approach a value of one indicate that the sample has the trait associated with the classifier whereas classifier equation values that approach zero indicate that the sample does not have the trait associated with the classifier. In other embodiments, the equations are regressed so that the opposite relationship hold (e.g., equation values approach one indicate absence of an associated trait). In one embodiment, each equation is assigned a "+1" vote if the equation approaches one or a "−1" vote if the equation approaches zero. Equation votes are summed. If the net summation is positive, then the subject is deemed to have the trait associated with the classifier. If the net summation is negative, then the subject is deemed not to have the trait associated with the classifier. In some embodiments, step 330 is performed by model polling and reporting module 66.

Step 332.

One of the advantages of the present invention is that a single sample collected in accordance with Section 5.2 can be used to test the patient for one or more of a plurality of molecular markers which may be useful for one or more traits. Accordingly, in step 332, a determination is made as to whether the patient has been tested for each pair of traits for which a determination is required. If additional determinations are required (332—No), process control is returned to step 330 and the measured molecular marker data from the patient is used to help determine the likelihood as to whether a subject has other traits represented by a trait subgroup in training population 44.

Step 334.

When the patient sample has been used to determine if the subject has any of a plurality of different traits as determined by one or more classifiers or classifier groups, a report is generated. In some embodiments, this report includes the results of each classification test. In other words, the report provides an indication as to whether it is likely the tested subject has any one of a plurality of different traits. In some embodiments, step 334 is performed by classifier polling and reporting module 66. Section 5.5 provides a summary of some of the applications for classifiers constructed using the methods of the present invention.

5.2 Source of Molecular Marker Data

The present invention provides methods for identifying molecular markers by obtaining molecular marker data which represents the products of molecular markers found in a blood sample. Molecular markers are thus identified that correlate with, are associated with, or indicate a trait. The present invention also provides methods for detecting, diagnosing, monitoring, prognosing or predicting a trait or reoccurrence of a trait based upon data corresponding to the expression of molecular markers in a blood sample. As used herein, the terms "subject" and "patient" and "individual" are used interchangeably to refer to an animal (e.g., a mammal, a fish, an amphibian, a reptile, a bird, and an insect). In a specific embodiment, a subject is a mammal (e.g., a non-human mammal and a human). In another embodiment, a subject is a pet (e.g., a dog, a cat, a guinea pig, a monkey and a bird), a farm animal (e.g., a horse, a cow, a pig, a goat and a chicken) or a laboratory animal (e.g., a mouse and rat). In another embodiment, the subject is a primate (e.g., a chimpanzee and a human). In a preferred embodiment, the subject is a human.

5.2.1 Source of a Blood Sample

A blood sample obtained from any subject may be used in accordance with the methods of the invention. Examples of subjects from which a blood sample can be obtained and utilized in accordance with the methods of the invention include, but are not limited to, asymptomatic subjects, subjects manifesting or exhibiting 1, 2, 3, 4 or more traits or symptoms of a trait, subjects clinically diagnosed as having a trait, subjects predisposed to a trait (e.g., subjects with a family history of a trait, subjects with a genetic predisposition to a trait, and subjects that lead a lifestyle that predisposes them to a trait or increases the likelihood of contracting a trait), subjects suspected of having a trait, subjects undergoing therapy for a trait, subjects non-responsive to a therapy, subjects responsive to a therapy, subjects with more than one trait (e.g., subjects with 2, 3, 4, 5 or more traits), subjects not undergoing therapy for a trait, subjects determined by a medical practitioner (e.g., a physician) to be healthy or disease-free, subjects that are in remission, subjects cured of trait, and subjects that have not been diagnosed with a condition. In specific embodiment, the condition is a disease. In another specific embodiment, a condition is any state that is codified in the *International Classification of Diseases*, $9^{th}$ Revision, Department of Health and Human Services (ICD-9 codes) and/or SNOMED Clinical Terms (SNOMED CT®) which is hereby incorporated by reference, or equivalent treatise.

Non-limiting examples of disease include, but are not limited to, blood disorder, blood lipid disease, autoimmune disease, arthritis (e.g., osteoarthritis, rheumatoid arthritis, juvenile rheumatoid arthritis and the like), bone or joint disorder, lupus, an allergy, a cardiovascular disorder (e.g., heart failure, congenital heart disease, rheumatic fever, valvular heart disease, corpulmonale, cardiomyopathy, myocarditis, pericardial disease, vascular diseases such as atherosclerosis, acute myocardial infarction, ischemic heart disease and the like), obesity, respiratory disease (e.g., asthma, pneumonitis, pneumonia, pulmonary infections, lung disease, bronchiectasis, tuberculosis, cystic fibrosis, interstitial lung disease, chronic bronchitis emphysema, pulmonary hypertension, pulmonary thromboembolism, acute respiratory distress syndrome and the like), hyperlipidemias, endocrine disorder, immune disorder, infectious disease, muscle wasting and whole body wasting disorder, neurological disorder (e.g., migraines, seizures, epilepsy, cerebrovascular disease, Parkinson's, ataxic disorders, motor neuron diseases, cranial nerve disorders, spinal cord disorders, meningitis and the like), neurodegenerative disease (e.g., alzheimers, dementia and the like), neuropsychiatric disease (e.g., schizophrenia, anxiety and the like), mood disorders (e.g., bipolar disorder; manic depression and the like), skin disorder, kidney disease, scleroderma, stroke, hereditary hemorrhage telangiectasia, diabetes, disorders associated with diabetes (e.g., PVD), hypertension, Gaucher's disease, cystic fibrosis, sickle cell anemia, liver disease, stomach disease, pancreatic disease, eye disease, ear disease, nose disease, throat disease, diseases affecting the reproductive organs, gastrointestinal diseases (including diseases of the colon, diseases of the spleen, appendix, gall bladder, and others) and the like. For further discussion of human diseases, see Mendelian Inheritance in Man: A Catalog of Human Genes and Genetic Disorders by Victor A. McKusick (12th Edition, 3 volume set, June 1998, Johns Hopkins University Press, ISBN: 0801857422) and Harrison's Principles of Internal Medicine by Braunwald, Fauci, Kasper, Hauser, Longo, & Jameson (15th Edition 2001), the entirety of each of which is incorporated herein. Additional examples of disease are disclosed in Section 5.8, below.

In one embodiment of the invention, the disease is an immune disorder, such as those associated with overexpression of a gene or expression of a mutant gene (e.g., autoimmune diseases, such as diabetes mellitus, arthritis (including rheumatoid arthritis, juvenile rheumatoid arthritis, osteoarthritis, and psoriatic arthritis), multiple sclerosis, encephalomyelitis, myasthenia gravis, systemic lupus erythematosis, automimmune thyroiditis, dermatitis (including atopic dermatitis and eczematous dermatitis), psoriasis, Sjogren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing, loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy.

In another embodiment, a disease of the invention is a cellular proliferative and/or differentiative disorder that includes, but is not limited to, cancer, e.g., carcinoma, sarcoma or other metastatic disorders and the like. As used herein, the term "cancer" refers to cells having the capacity for autonomous growth, i.e., an abnormal state of condition characterized by rapidly proliferating cell growth. "Cancer" is meant to include all types of cancerous growths, pre-cancerous growths or lesions, oncogenic processes, metastatic tissues or malignantly transformed cells, tissues, or organs, irrespective of histopathologic type or stage of invasiveness. Examples of cancers include, but are not limited to, solid tumors, tissue specific tumors, benign cancer, metastatic cancers, early stage cancer, late stage cancer and leukemias, including: apudoma, choristoma, branchioma, malignant carcinoid syndrome, carcinoid heart disease, carcinoma (e.g., Walker, basal cell, basosquamous, Brown-Pearce, ductal, Ehrlich tumour, in situ, Krebs 2, Merkel cell, mucinous, non-small cell lung, oat cell, papillary, scirrhous, bronchiolar, bronchogenic, squamous cell, and transitional cell), histiocytic disorders, leukaemia (e.g., B cell, mixed cell, null cell, T cell, T-cell chronic, HTLV-II-associated, lymphocytic acute, lymphocytic chronic, mast cell, and myeloid), histiocytosis malignant, Hodgkin disease, immunoproliferative small, non-Hodgkin lymphoma, plasmacytoma, reticuloendotheliosis, melanoma, chondroblastoma, chondroma, chondrosarcoma, fibroma, fibrosarcoma, giant cell tumors, histiocytoma, lipoma, liposarcoma, mesothelioma, myxoma, myxosarcoma, osteoma, osteosarcoma, Ewing sarcoma, synovioma, adenofibroma, adenolymphoma, carcinosarcoma, chordoma, craniopharyngioma, dysgerminoma, hamartoma, mesenchymoma, mesonephroma, myosarcoma, ameloblastoma, cementoma, odontoma, teratoma, thymoma, trophoblastic tumour, adeno-carcinoma, adenoma, cholangioma, cholesteatoma, cylindroma, cystadenocarcinoma, cystadenoma, granulosa cell tumour, gynandroblastoma, hepatoma, hidradenoma, islet cell tumour, Leydig cell tumour, papilloma, Sertoli cell tumour, theca cell tumour, leiomyoma, leiomyosarcoma, myoblastoma, mymoma, myosarcoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, paraganglioma nonchromaffin, angiokeratoma, angiolymphoid hyperplasia with eosinophilia, angioma sclerosing, angiomatosis, glomangioma, hemangioendothelioma, hemangioma, hemangiopericytoma, hemangiosarcoma, lymphangioma, lymphangiomyoma, lymphangiosarcoma, pinealoma, carcinosarcoma, chondrosarcoma, cystosarcoma, phyllodes, fibrosarcoma, hemangiosarcoma, leimyosarcoma, leukosarcoma, liposarcoma, lymphangiosarcoma, myosarcoma, myxosarcoma, ovarian carcinoma, rhabdomyosarcoma, sarcoma (e.g., Ewing, experimental, Kaposi, and mast cell), neoplasms (e.g., bone, breast, digestive system, colorectal, liver, pancreatic, pituitary, testicular, orbital, head and neck, central nervous system, acoustic, pelvic respiratory tract, and urogenital), neurofibromatosis, and cervical dysplasia, and other conditions in which cells have become immortalized or transformed.

5.2.2 Methods for Collecting Blood

In one aspect, a sample of blood is obtained from a subject according to methods well known in the art. The present invention can use whole blood, but can also use blood in which the serum or plasma has been removed and the RNA or mRNA isolated from the remaining sample in accordance with methods known in the art (for example, using preferably gentle centrifugation at 300-800×g for five to ten minutes).

In some embodiments a drop of blood is collected from a simple pin prick made in the skin of a subject. In such embodiments, this drop of blood collected from a pin prick is all that is needed. A drop of blood can include volumes of anywhere from 1 OuI through to 10 OuI. Blood may be drawn from a subject from any part of the body (e.g., a finger, a hand, a wrist, an arm, a leg, a foot, an ankle, a stomach, and a neck) using techniques known to one of skill in the art, in particular methods of phlebotomy known in the art. In a specific embodiment, venous blood is obtained from a subject and utilized in accordance with the methods of the invention. In another embodiment, arterial blood is obtained and utilized in accordance with the methods of the invention. The composition of venous blood varies according to the metabolic needs of the area of the body it is servicing. In contrast, the composition of arterial blood is consistent throughout the body. For routine blood tests, venous blood is generally used.

Venous blood can be obtained from any source including the basilic vein, cephalic vein, or median vein. Arterial blood can be obtained from the radial artery, brachial artery or femoral artery. A vacuum tube, a syringe or a butterfly may be used to draw the blood. Typically, the puncture site is cleaned, a tourniquet is applied approximately 3-4 inches above the puncture site, a needle is inserted at about a 15-45 degree angle, and if using a vacuum tube, the tube is pushed into the needle holder as soon as the needle penetrates the wall of the vein. When finished collecting the blood, the needle is removed and pressure is maintained on the puncture site. Usually, heparin or another type of anticoagulant is in the tube or vial that the blood is collected in so that the blood does not clot. When collecting arterial blood, anesthetics can be administered prior to collection.

The amount of blood collected will vary depending upon the site of collection, the amount required for a method of the invention, and the comfort of the subject. However, an advantage of one embodiment of the present invention is that the amount of blood required to implement the methods of the present invention can be so small that more invasive procedures are not required to obtain the sample. For example, in some embodiments, all that is required is a drop of blood. This drop of blood can be obtained, for example, from a simple pinprick. In some embodiments, any amount of blood is collected that is sufficient to measure molecular marker data. As such, in some embodiments, the amount of blood that is collected is 1 µl or less, 0.5 µl or less, 0.1 µl or less, or 0.01 µl or less. However, the present invention is not limited to such embodiments. In some embodiments more blood is available and in some embodiments, more blood can be used to effect the methods of the present invention. As such, a broad range of blood volumes is contemplated and can be used to obtain the molecular marker data measurement data used in the present invention. In various specific embodiments, 0.001 ml, 0.005 ml, 0.01 ml, 0.05 ml, 0.1 ml, 0.15 ml, 0.2 ml, 0.25 ml, 0.5 ml, 0.75 ml, 1 ml, 1.5 ml, 2 ml, 3 ml, 4 ml, 5 ml, 10 ml, 15 ml or more of blood is collected from a subject. In other specific embodiments, 0.001 ml to 15 ml, 0.01 ml to 10 ml, 0.1 ml to 10 ml, 0.1 ml to 5 ml, 1 to 5 ml of blood is collected from a subject.

In some embodiments of the present invention, blood is stored within a K3/EDTA tube. In another embodiment, one can utilize tubes for storing blood which contain stabilizing agents such as disclosed in U.S. Pat. No. 6,617,170. In another embodiment, the PAXgene™ blood RNA system provided by PreAnalytiX, a Qiagen/BD company, can be used to collect blood. In yet another embodiment, the Tempus™ blood RNA collection tubes, offered by Applied Biosystems, can be used. Tempus™ collection tubes provide a closed evacuated plastic tube containing RNA stabilizing reagent for whole blood collection.

The collected blood is optionally but preferably stored at refrigerated temperatures, such as 4° C., prior to molecular marker data measurement. In some embodiments, a portion of the blood sample is used for molecular measurement at a first instance of time whereas one or more remaining portions of the blood sample is stored for a period of time for later use. This period of time can be an hour or more, a day or more, a week or more, a month or more, a year or more, or indefinitely. For long term storage, storage methods well known in the art, such as storage at cryo temperatures (e.g. below −60° C.) can be used. In some embodiments, in addition to storage of the blood (or instead of storage of the blood), isolated molecular markers (e.g., nucleic acid, protein, carbohydrates, lipids, metabolites, etc.) are stored for a period of time for later use. Storage of such molecular markers can be for an hour or more, a day or more, a week or more, a month or more, a year or more, or indefinitely.

5.2.3 Method of Isolating Blood Cells

In some embodiments of the present invention, whole blood is used directly to isolate and analyze the products of one or more molecular markers so as to obtain molecular marker data. In other embodiments of the invention fractionated blood can be used. By fractionated blood is meant blood in which the blood cells are separated prior to isolation of the molecular markers using techniques known in the art. For example, fractionated blood includes blood wherein the blood cells are fractionated using Ficoll-Hypaque (Pharmacia) gradient centrifugation. Such centrifugation separates erythrocytes (red blood cells) from various types of nucleated cells and from plasma. As such, in some embodiments of the present invention, a blood sample of the invention is fractionated blood. In one embodiment, peripheral blood leukocytes are utilized ("PBLs"). PBLs are separated from the remainder of the blood using a Ficoll® gradient.

By way of example but not limitation, macrophages can be obtained as follows. Mononuclear cells are isolated from peripheral blood of a subject, by syringe removal of blood followed by Ficoll-Hypaque gradient centrifugation. Tissue culture dishes are pre-coated with the subject's own serum or with AB+ human serum and incubated at 37° C. for one hour. Non-adherent cells are removed by pipetting. Cold (4° C.) 1 mM EDTA in phosphate-buffered saline is added to the adherent cells left in the dish and the dishes are left at room temperature for fifteen minutes. The cells are harvested, washed with RPMI buffer and suspended in RPMI buffer. Increased numbers of macrophages can be obtained by incubating at 37° C. with macrophage-colony stimulating factor (M-CSF). Antibodies against macrophage specific surface markers, such as Mac-1$_5$ can be labeled by conjugation of an affinity compound to such molecules to facilitate detection and separation of macrophages. Affinity compounds that can be used include but are not limited to biotin, photobiotin, fluorescein isothiocyante (FITC), or phycoerythrin (PE), or other compounds known in the art. Cells retaining labeled antibodies are then separated from cells that do not bind such antibodies by techniques known in the art such as, but not limited to, various cell sorting methods, affinity chromatography, and panning.

Blood cells can be fractionated using a fluorescence activated cell sorter (FACS). Fluorescence activated cell sorting (FACS) is a known method for separating particles, including cells, based on the fluorescent properties of the particles. See, for example, Kamarch, 1987, Methods Enzymol 151:150 165. Laser excitation of fluorescent moieties in the individual particles results in a small electrical charge allowing electromagnetic separation of positive and negative particles from a mixture. An antibody or ligand used to detect a blood cell antigenic determinant present on the cell surface of particular blood cells is labeled with a fluorochrome, such as FITC or phycoerythrin. The cells are incubated with the fluorescently labeled antibody or ligand for a time period sufficient to allow the labeled antibody or ligand to bind to cells. The cells are processed through the cell sorter, allowing separation of the cells of interest from other cells. FACS sorted particles can be directly deposited into individual wells of microtiter plates to facilitate separation.

Magnetic beads can be also used to separate blood cells in some embodiments of the present invention. For example, blood cells can be sorted using a magnetic activated cell sorting (MACS) technique, a method for separating particles based on their ability to bind magnetic beads (0.5 100 Dm diameter). A variety of useful modifications can be performed on the magnetic microspheres, including covalent addition of an antibody which specifically recognizes a cell solid phase surface molecule or hapten. A magnetic field is then applied, to physically manipulate the selected beads. In a specific embodiment, antibodies to a blood cell surface marker are coupled to magnetic beads. The beads are then mixed with the blood cell culture to allow binding. Cells are then passed through a magnetic field to separate out cells having the blood cell surface markers of interest. These cells can then be isolated.

In some embodiments, the surface of a culture dish may be coated with antibodies, and used to separate blood cells by a method called panning. Separate dishes can be coated with antibody specific to particular blood cells. Cells can be added first to a dish coated with blood cell specific antibodies of interest. After thorough rinsing, the cells left bound to the dish will be cells that express the blood cell markers of interest. Examples of cell surface antigenic determinants or markers include, but are not limited to, CD2 for T lymphocytes and natural killer cells, CD3 for T lymphocytes, CD1 Ia for leukocytes, CD28 for T lymphocytes, CD 19 for B lymphocytes, CD20 for B lymphocytes, CD21 for B lymphocytes, CD22 for B lymphocytes, CD23 for B lymphocytes, CD29 for leukocytes, CD14 for monocytes, CD41 for platelets, CD61 for platelets, CD66 for granulocytes, CD67 for granulocytes and CD68 for monocytes and macrophages.

Whole blood can also be fractioned into cells types such as leukocytes, platelets, erythrocytes, etc. Leukocytes can be further separated into granulocytes and agranulocytes using standard techniques. Granulocytes can be separated into cell types such as neutrophils, eosinophils, and basophils using standard techniques. Agranulocytes can be separated into lymphocytes (e.g., T lymphocytes and B lymphocytes) and monocytes using standard techniques. T lymphocytes can be separated from B lymphocytes and helper T cells separated from cytotoxic T cells using standard techniques. Separated blood cells (e.g., leukocytes) can be frozen by standard techniques prior to use in the present methods.

5.2.4 Blood Samples Used in Methods of the Invention

In accordance with the methods of the invention, the term "blood sample" can include any of the samples discussed in section 5.2.3. In some embodiments, this includes whole blood, fractionated blood, a sample of subsets of fractionated blood, and a sample of specific types of blood cells. In a specific embodiment, the whole blood sample can have the plasma or serum removed by centrifugation, using preferably gentle centrifugation at 300-800×g for five to ten minutes.

In another embodiment, a blood sample of the invention is a sample of peripheral blood leukocytes (PBLs). In another embodiment, a blood sample of the invention is a sample of granulocytes. In another embodiment, a blood sample of the invention is a sample of neutrophils, eosinophils, basophils or any combination thereof. In another embodiment, a blood sample of the invention is a sample of agranulocytes. In another embodiment, a blood sample of the invention is a sample of lymphocytes, monocytes or a combination thereof. In yet another embodiment, a blood sample of the invention is a sample of T lymphocytes, B lymphocytes or a combination thereof. See, e.g., Section 5.4.3 supra for methods of isolating blood cells.

A blood sample that is useful according to the invention is in an amount that is sufficient for the detection of one or more molecular markers according to the invention. In a specific embodiment, a blood sample useful according to the invention is in an amount ranging from 1 µl to 100 ml, preferably 10 µl to 50 ml, more preferably 10 µl to 25 ml and most preferably 10 µl to 1 ml.

In one embodiment whole blood, or serum free whole blood is taken and the redblood cells are lysed with lysing buffer. In a specific embodiment, the Lysis Buffer (IL) consists of 0.6 g EDTA 1.0 g $KHCO_2$, and 8.2 g $NH_4Cl$ adjusted to pH 7.4 (using NaOH). Once mixed with lysing buffer, the sample is centrifuged and the cell pellet retained and RNA or mRNA extracted in accordance with methods known in the art ("lysed whole blood") (see, for example, Sambrook, Fritsch & Maniatis, "Molecular Cloning: A Laboratory Manual (1982); "DNA Cloning: A Practical Approach," Volumes I and II (D. N. Glover ed. 1985). The use of whole blood or lysed whole blood is preferred since it avoids the costly and time-consuming need to separate out the cell types within the blood (Liew et al. U.S. Patent Application No. US 2004/0014059). In another embodiment, whole blood is stored and stabilized using PAXgene® tubes and RNA can be isolated using the PAXgene® RNA Isolation system. In yet another embodiment, RNA is isolated from whole blood which has been isolated using PAXgene® and additional globin reduction protocols followed.

5.3 Methods for Measuring Molecular Marker Data

The techniques described in this section are particularly useful for obtaining molecular marker data for step 202 wherein the data is reflective of the products of the molecular marker—e.g. measurement of the abundance of RNA or protein products in blood corresponding to all of the molecular markers of the genome or "a portion thereof. In particular, the techniques useful for step 202 are those techniques which allow the ability to comprehensively screen for candidate molecular markers quickly and effectively. These techniques preferably provide molecular marker data for a large number of molecular markers concurrently, thereby allowing greater ability to screen molecular markers corresponding to the entire genome, or a portion thereof in a short period of time. In addition to the techniques described in this Section 5.3, any technique known to one of skill in the art to measure the abundance of RNA or protein corresponding to the entire genome or "a portion thereof can be used to measure such data. In one embodiment, "a portion thereof is data corresponding to the amount of RNA or protein expressed from more than 1,000, more than 2,000, more than 5,000, more than 10,000, more than 20,000, more than 30,000 molecular markers. In another embodiment, the "a portion thereof refers to at least 50%, at least 55%, at least 60%, at least 65%, at least 70%, at least 75%, at least 80%, at least 85%, at least 90%, or at least 95% of the genome. See, e.g., Sambrook, Fritsch & Maniatis, 1982, *Molecular Cloning: A Laboratory Manual; DNA Cloning: A Practical Approach*, volumes I and II (D. N. Glover ed. 1985); Oligonucleotide Synthesis Gait ed., 1984; *Nucleic Acid Hybridization*, Hames & Higgins eds., 1985; *Transcription and Translation*, Hames & Higgins eds., 1984, *Animal Cell Culture*, Freshney ed., 1986, *Immobilized Cells And Enzymes*, IRL Press, 1986, Perbal, 1984, *A Practical Guide To Molecular Cloning*, each of which is hereby incorporated by reference in its entirety. In one embodiment more than technique can be used to measure data for each molecular marker to perform step 202.

5.3.1 RNA Measurement Techniques

Any technique known to one of skill in the art may be used to measure the level of expression of a molecular marker by measuring the amount of the product of the molecular marker. In one embodiment the RNA in blood corresponding to the molecular marker is measured. By "corresponding to a molecular marker" is meant RNA transcribed from a molecular marker (or proteins translated from RNA which is transcribed from a molecular marker when referring to protein products of a molecular marker). RNA or protein which corresponds to a molecular marker are also considered the product of the molecular marker. In a specific embodiment, the level of an RNA product is measured using a technique which permits generation of data for a large number of molecular markers. However measured, the result is either the absolute or relative amounts of abundance of nucleic acids corresponding to the molecular markers, including but not limited to values representing abundances or abundance ratios.

5.3.1.1 Microarrays

In one embodiment, nucleic acid arrays are employed for analyzing the level of RNA product of each molecular marker of the genome in a blood sample. In a specific embodiment, molecular marker data is obtained by hybridizing detectably labeled polynucleotides representing the nucleic acid sequences in mRNA transcripts present in a cell (e.g., fluorescently labeled cDNA synthesized from total cell mRNA) to a microarray. In some embodiments expressed transcripts that may or may not represent genes expressed in the blood sample are analyzed.

In some embodiments, a microarray is an array of positionally-addressable binding (e.g., hybridization) sites on a support for representing many of the nucleic acid sequences in the genome of a cell or organism. Is some embodiments, a microarray represents most or almost all of the genes in a species. In some embodiments, each microarray binding site consists of polynucleotide probes bound to a predetermined region on the support. Microarrays are described in Draghici, *Data Analysis Tools For DNA Microarrays*, 2003, Chapman & Hall, CRC Press, New York, pp. 15-16, which is hereby incorporated by reference in its entirety.

Microarrays can be made in a number of ways. See, for example, Draghici, *Data Analysis Tools For DNA Microarrays*, 2003, Chapman & Hall, CRC Press, New York, pp. 16-22, which is hereby incorporated by reference in its entirety. Preferably microarrays are reproducible, allowing multiple copies of a given array to be produced and results from the microarrays compared with each other. Preferably, the microarrays are made from materials that are stable under binding (e.g., nucleic acid hybridization) conditions. Microarrays are preferably small, e.g., between 1 $cm^2$ and 25 $cm^2$, preferably 1 to 3 $cm^2$. However, both larger and smaller arrays are also contemplated and may be preferable, e.g., for simultaneously evaluating a very large number or very small number of different probes.

In some embodiments, a given binding site or unique set of binding sites in the microarray will specifically bind (e.g., hybridize) to a nucleotide sequence in a single gene from a cell or organism (e.g., to exon of a specific mRNA or a specific cDNA derived therefrom).

Microarrays used in the present invention can include one or more test probes. In some embodiments each such test probe comprises a polynucleotide sequence that is complementary to a subsequence of RNA or DNA to be detected. Each probe typically has a different nucleic acid sequence, and the position of each probe on the solid surface of the array is usually known or can be determined. Microarrays useful in accordance with the invention can include oligonucleotide microarrays, cDNA based arrays, SNP arrays, spliced variant arrays and any other array able to provide a quantitative or semi quantitative data of the invention. Some types of microarrays are addressable arrays. More specifically, some microarrays are positionally addressable arrays. In some embodiments, each probe of the array is located at a known, predetermined position on the solid support so that the identity (e.g., the sequence) of each probe can be determined from its position on the array (e.g., on the support or surface). In some embodiments, the arrays are ordered arrays.

In some embodiments, the density of probes on a microarray or a set of microarrays is 100 different (e.g., non-identical) probes per 1 cm$^2$ or higher. More preferably, a microarray used in the methods of the invention will have at least 550 probes per 1 cm$^2$, at least 1,000 probes per 1 cm$^2$, at least 1,500 probes per 1 cm$^2$ or at least 2,000 probes per 1 cm$^2$. In a particularly preferred embodiment, the microarray is a high density array, preferably having a density of at least 2,500 different probes per 1 cm$^2$. The microarrays used in the invention therefore preferably contain at least 2,500, at least 5,000, at least 10,000, at least 15,000, at least 20,000, at least 25,000, at least 50,000 or at least 55,000 different (i.e., non-identical) probes.

In one embodiment, the microarray is an array (e.g., a matrix) in which each position represents a discrete binding site for a nucleotide sequence of a transcript encoded by a gene (e.g., for an exon of an mRNA or a cDNA derived therefrom). The collection of binding sites on a microarray contains sets of binding sites for a plurality of genes and thus can be used, in some embodiments to measure molecular marker data. For example, in various embodiments, the microarrays of the invention can comprise binding sites for products encoded by fewer than 50% of the genes in the genome of an organism. Alternatively, the microarrays of the invention can have binding sites for the products encoded by at least 50%, at least 75%, at least 85%, at least 90%, at least 95%, at least 99% or 100% of the molecular markers of an organism. In other embodiments, the microarrays of the invention can having binding sites for products encoded by fewer than 50%, by at least 50%, by at least 75%, by at least 85%, by at least 90%, by at least 95%, by at least 99% or by 100% of the genes expressed by a cell of an organism. The binding site can be a DNA or DNA analog to which a particular RNA can specifically hybridize. The DNA or DNA analog can be, e.g., a synthetic oligomer or a gene fragment, e.g. corresponding to an exon.

In some embodiments of the present invention, an expressed transcript is represented in the nucleic acid arrays. In such embodiments, a set of binding sites can include probes with different polynucleotides that are complementary to different sequence segments of the expressed transcript. Exemplary polynucleotides that fall within this class can be of length of 15 to 200 bases, 20 to 100 bases, 40-60 bases or some other range of bases. Each probe sequence can also comprise linker sequences in addition to the sequence that is complementary to its target sequence. As used herein, a linker sequence is a sequence between the sequence that is complementary to its target sequence and the surface of support. For example, in some embodiments, the nucleic acid arrays of the invention comprise one probe specific to each target gene or exon. However, if desired, the nucleic acid arrays can contain at least 2, 5, 10, 100, or 1000 or more probes specific to some expressed transcript. For example, the array may contain probes tiled across the sequence of the longest mRNA isoform of a gene at single base steps.

In specific embodiments of the invention, when an exon has alternative spliced variants, a set of polynucleotide probes of successive overlapping sequences, i.e., tiled sequences, across the genomic region containing the longest variant of an exon can be included in the exon nucleic acid arrays. The set of polynucleotide probes can comprise successive overlapping sequences at steps of a predetermined base intervals, e.g. at steps of 1, 5, or 10 base intervals, span, or are tiled across, the mRNA containing the longest variant. Such sets of probes therefore can be used to scan the genomic region containing all variants of an exon to determine the expressed variant or variants of the exon to determine the expressed variant or variants of the exon. Alternatively or additionally, a set of polynucleotide probes comprising exon specific probes and/or variant junction probes can be included in the exon profiling array. As used herein, a variant junction probe refers to a probe specific to the junction region of the particular exon variant and the neighboring exon. In some cases, the probe set contains variant junction probes specifically hybridizable to each of all different splice junction sequences of the exon. In other cases, the probe set contains exon specific probes specifically hybridizable to the common sequences in all different variants of the exon, and/or variant junction probes specifically hybridizable to the different splice junction sequences of the exon.

In some cases, an exon is represented in the exon nucleic acid arrays by a probe comprising a polynucleotide that is complementary to the full length exon. In such instances, an exon is represented by a single binding site on the profiling arrays. In some preferred cases, an exon is represented by one or more binding sites on the profiling arrays, each of the binding sites comprising a probe with a polynucleotide sequence that is complementary to an RNA fragment that is a substantial portion of the target exon. The lengths of such probes are normally between 15-600 bases, preferably between 20-200 bases, more preferably between 30-100 bases, and most preferably between 40-80 bases. The average length of an exon is 200 bases (see, e.g., Lewin, Genes V, Oxford University Press, Oxford, 1994). A probe of length of 40-80 allows more specific binding of the exon than a probe of shorter length, thereby increasing the specificity of the probe to the target exon. For certain genes, one or more targeted exons may have sequence lengths less than 40-80 bases. In such cases, if probes with sequences longer than the target exons are to be used, it may be desirable to design probes comprising sequences that include the entire target exon flanked by sequences from the adjacent constitutively splice exon or exons such that the probe sequences are complementary to the corresponding sequence segments in the mRNAs. Using flanking sequence from adjacent constitutively spliced exon or exons rather than the genomic flanking sequences, i.e., intron sequences, permits comparable hybridization stringency with other probes of the same length. Preferably the flanking sequence used are from the adjacent constitutively spliced exon or exons that are not involved in any alternative pathways. More preferably the flanking sequences used do not comprise a significant portion of the sequence of the adjacent exon or exons so that cross-hybridization can be minimized. In some embodiments, when a target exon that is shorter than the desired probe length is involved in alternative splicing, probes comprising flanking sequences in different alternatively spliced mRNAs are designed so that expression level of the exon expressed in different alternatively spliced mRNAs can be measured.

In some instances, when alternative splicing pathways and/or exon duplication in separate genes are to be distinguished, the DNA array or set of arrays can also comprise probes that are complementary to sequences spanning the junction regions of two adjacent exons. Preferably, such probes comprise sequences from the two exons which are not substantially overlapped with probes for each individual exons so that cross hybridization can be minimized. Probes that comprise sequences from more than one exons are useful in distinguishing alternative splicing pathways and/or expression of duplicated exons in separate genes if the exons occurs in one or more alternative spliced mRNAs and/or one or more separated genes that contain the duplicated exons but not in other alternatively spliced mRNAs and/or other genes that contain the duplicated exons. Alternatively, for duplicate exons in separate genes, if the exons from different genes show substantial difference in sequence homology, it is preferable to include probes that are different so that the exons from different genes can be distinguished.

It will be apparent to one skilled in the art that any of the probe schemes, supra, can be combined on the same nucleic acid array and/or on different arrays within the same set of nucleic acid arrays so that a more accurate determination of the expression profile for a plurality of molecular marker products can be accomplished. It will also be apparent to one skilled in the art that the different probe schemes can also be used for different levels of accuracies in profiling. For example, a nucleic acid array or array set comprising a small set of probes for each expressed transcript or each region thereof may be used to identify molecular markers under certain specific conditions. An array or array set comprising larger sets of probes for the exons that are of interest is then used to more accurately determine the specific molecular marker products under such specific conditions. Other DNA array strategies that allow more advantageous use of different probe schemes are also encompassed.

In some embodiments, the microarrays used in the invention can include binding sites (e.g., probes) for sets of exons for one or more genes relevant to the condition of interest. The number of genes in a genome can be estimated from the number of mRNAs expressed by the cell or organism, or by extrapolation of a well characterized portion of the genome. When the genome of the organism of interest has been sequenced, the number of ORFs can be determined and mRNA coding regions identified by analysis of the DNA sequence. For example, the human genome is now known. Genome sequences for other organisms are also completed or nearly completed. Thus, in some embodiments of the invention, an array set comprising the total probes for all known or predicted exons in the genome of an organism is provided. As a non-limiting example, the present invention provides an array set comprising one or two probes for each known or predicted exon of a molecular marker of the human genome.

It will be appreciated that when cDNA complementary to the RNA of a cell is made and hybridized to a microarray under suitable hybridization conditions, the level of hybridization to the site in the array corresponding to an exon of any particular molecular marker will reflect the prevalence in the cell of mRNA or mRNAs containing the exon transcribed from that molecular marker. For example, when detectably labeled (e.g., with a fluorophore) cDNA complementary to the total cellular mRNA is hybridized to a microarray, the site on the array corresponding to an exon of a gene (i.e., capable of specifically binding the product or products of the gene expressing) that is not transcribed or is removed during RNA splicing in the cell will have little or no signal (e.g., fluorescent signal), and an exon of a gene for which the encoded mRNA expressing the exon is prevalent will have a relatively strong signal. The relative abundance of different mRNAs produced from the same gene by alternative splicing is then determined by the signal strength pattern across the whole set of exons monitored for the gene.

The use of a two-color fluorescence labeling and detection scheme to define alterations in gene expression has been described in connection with detection of mRNAs, e.g., in Shena et al, 1995, Science 270:467-470, which is incorporated by reference in its entirety for all purposes. In some embodiments, such schemes are used to measure molecular marker data. Such schemes are equally applicable to labeling and detection of expressed transcripts. An advantage of using cDNA labeled with two different fluorophores is that a direct and internally controlled comparison of the mRNA or exon expression levels corresponding to each arrayed gene in two blood samples can be made, and variations due to minor differences in experimental conditions (e.g., hybridization conditions) will not affect subsequent analyses. However, it will be recognized that it is also possible to use cDNA from a single cell, and compare, for example, the absolute amount of a particular exon in, e.g., a drug-treated or pathway-perturbed cell and an untreated cell. Furthermore, labeling with more than two colors is also contemplated in the present invention. In some embodiments of the invention, at least 5, 10, 20, or 100 dyes of different colors can be used for labeling. Such labeling permits simultaneous hybridizing of the distinguishably labeled cDNA populations to the same array, and thus measuring, and optionally comparing the expression levels of, mRNA molecules derived from more than two samples. Dyes that can be used include, but are not limited to, fluorescein and its derivatives, rhodamine and its derivatives, texas red, 5'carboxy-fluorescein ("FMA"), 2',7'-dimethoxy-4',5'-dichloro-6-carboxy-fluorescein ("JOE"), N,N,N',N'-tetramethyl-6-carboxy-rhodamine ("TAMRA"), 6'carboxy-X-rhodamine ("ROX"), HEX, TET, IRD40, and IRD41, cyamine dyes, including but are not limited to Cy3, Cy3.5 and Cy5; BODIPY dyes including but are not limited to BODIPY-FL, BODIPY-TR, BODIPY-TMR, BODIPY-630/650, and BODIPY-650/670; and ALEXA dyes, including but are not limited to ALEXA-488, ALEXA-532, ALEXA-546, ALEXA-568, and ALEXA-594; as well as other fluorescent dyes which will be known to those who are skilled in the art.

In one embodiment, hybridization levels at different hybridization times are measured separately on different, identical microarrays. For each such measurement, at hybridization time when hybridization level is measured, the microarray is washed briefly, preferably in room temperature in an aqueous solution of high to moderate salt concentration (e.g., 0.5 to 3 M salt concentration) under conditions which retain all bound or hybridized polynucleotides while removing all unbound polynucleotides. The detectable label on the remaining, hybridized polynucleotide molecules on each probe is then measured by a method which is appropriate to the particular labeling method used. The resulted hybridization levels are then combined to form a hybridization curve.

In another embodiment, hybridization levels are measured in real time using a single microarray. In this embodiment, the microarray is allowed to hybridize to the sample without interruption and the microarray is interrogated at each hybridization time in a non-invasive manner. In still another embodiment, one can use one array, hybridize for a short time, wash and measure the hybridization level, put back to the same sample, hybridize for another period of time, wash and measure again to get the hybridization time curve.

In a specific embodiment, the Affymetrix® Human Genome U133 (HG-U133) Set, consisting of two GeneChip® arrays, is used in accordance with known methods. The Human Genome U133 (HG-U133) Set contains almost 45,000 probe sets representing more than 39,000 transcripts derived from approximately 33,000 well-substantiated human genes. This set design uses sequences selected from GenBank®, dbEST, and RefSeq. The sequence clusters were created from the UniGene database (Build 133, Apr. 20, 2001). They were then refined by analysis and comparison with a number of other publicly available databases including the Washington University EST trace repository and the University of California, Santa Cruz Golden Path human genome database (April 2001 release).

In another embodiment, the HG-U133A array is used in accordance with the methods of the invention. The HG-U133A array includes representation of the RefSeq database sequences and probe sets related to sequences previously represented on the Human Genome U95Av2 array. The HG-U133B array contains primarily probe sets representing EST clusters. In another embodiment, the U133 Plus 2.0 GeneChip® is used in the invention. The U133 Plus 2.0 GeneChip® represents over 47,000 transcripts.

In another embodiment, a cDNA based microarray is used. In one embodiment the ChondroChip™ is used in accordance with the methods of the invention. The ChondroChip™ is a cDNA based microarray. One version of the ChondroChip™ includes 14,976 distinct elements: 10,382 known genes (69%), 4,112 EST/genomic DNA matches (28%), 328 clones with no significant match (2.2%), and 154 control spots (1.0%). Most if not all of the elements on the ChondroChip™ are complementary to ESTs identified as expressed in human chondrocytes. An article that describes the creation of a version of the ChondroChip™ is Zhang et ah, 2002, Osteoarthritis and Cartilage 10, 950-960, which is hereby incorporated by reference in its entirety.

In another embodiment, the BloodChip™ is used in accordance with the methods of the invention. The BloodChip is a cDNA microarray slide with 10,368 PCR products derived from peripheral blood cell cDNA libraries. The creation of the BloodChip™ microarray is described in Ma and Liew, 2003, Journal of Molecular and Cellular Cardiology 8, 993-998, which is hereby incorporated by reference in its entirety.

5.3.1.2 Target Polynucleotide Molecules

Target polynucleotides that can be analyzed by the methods and compositions of the invention include RNA molecules such as, but by no means limited to, expressed RNA molecules which includes messenger RNA (mRNA) molecules, mRNA spliced variants as well as other regulatory RNA, cRNA molecules (e.g., RNA molecules prepared from cDNA molecules that are transcribed in vivo) and fragments thereof. Target polynucleotides which may also be analyzed by the methods and compositions of the present invention include, but are not limited to DNA molecules such as genomic DNA molecules, cDNA molecules, and fragments thereof including oligonucleotides, ESTs, STSs, etc The target polynucleotide molecules may be naturally occurring nucleic acid molecules such as genomic or extragenomic DNA molecules isolated from a blood sample, or RNA molecules, such as mRNA molecules, isolated from a blood sample. The sample of target polynucleotides can comprise, e.g., molecules of DNA, RNA, or copolymers of DNA and RNA. In specific embodiments, the target polynucleotides of the invention will correspond to particular genes or to particular gene transcripts (e.g., to particular mRNA sequences expressed in specific cell types or to particular cDNA sequences derived from such mRNA sequences). The target polynucleotides may correspond to different exons of the same gene, e.g., so that different splice variants of that gene may be detected and/or analyzed.

In specific embodiments, the target polynucleotides to be analyzed are prepared in vitro from nucleic acids extracted from a blood sample. For example, in one embodiment, RNA is extracted from a blood sample (e.g., total cellular RNA, poly(A)+ messenger RNA, fraction thereof) and messenger RNA is purified from the total extracted RNA. Methods for preparing total and poly(A)+ RNA are well known in the art, and are described generally, e.g., in Sambrook, Fritsch & Maniatis, "Molecular Cloning: A Laboratory Manual (1982); "DNA Cloning: A Practical Approach," Volumes I and II (D. N. Glover ed. 1985). In one embodiment, RNA is extracted from a blood sample using guanidinium thiocyanate lysis followed by CsCl centrifugation and an oligo dT purification (Chirgwin et al., 1979, Biochemistry 18:5294-5299). In another embodiment, RNA is extracted from a blood sample using guanidinium thiocyanate lysis followed by purification on RNeasy columns (Qiagen). cDNA is then synthesized from the purified mRNA using, e.g., oligo-dT or random primers. In specific embodiments, the target polynucleotides are cRNA prepared from purified messenger RNA extracted from a blood sample. As used herein, cRNA is defined here as RNA complementary to the source RNA. The extracted RNAs can be amplified using a process in which doubled-stranded cDNAs are synthesized from the RNAs using a primer linked to an RNA polymerase promoter in a direction capable of directing transcription of anti-sense RNA. Anti-sense RNAs or cRNAs are then transcribed from the second strand of the double-stranded cDNAs using an RNA polymerase (see, e.g., U.S. Pat. Nos. 5,891,636, 5,716,785; 5,545, 522 and 6,132,997; see also, U.S. Pat. No. 6,271,002, and U.S. Provisional Patent Application Ser. No. 60/253,641, filed on Nov. 28, 2000, by Ziman et al.). Both oligo-dT primers (U.S. Pat. Nos. 5,545,522 and 6,132,997) or random primers (U.S. Provisional Patent Application Ser. No. 60/253,641, filed on Nov. 28, 2000, by Ziman et al.) that contain an RNA polymerase promoter or complement thereof can be used. In some embodiments the target polynucleotides are short and/or fragmented polynucleotide molecules which are representative of the original nucleic acid population of the blood sample.

The target polynucleotides to be analyzed by the methods and compositions of the invention can be detectably labeled. For example, cDNA can be labeled directly, e.g., with nucleotide analogs, or indirectly, e.g., by making a second, labeled cDNA strand using the first strand as a template. Alternatively, the double-stranded cDNA can be transcribed into cRNA and labeled.

In some embodiments the detectable label is a fluorescent label, e.g., by incorporation of nucleotide analogs. Other labels suitable for use in the present invention include, but are not limited to, biotin, iminobiotin, antigens, cofactors, dinitrophenol, lipoic acid, olefinic compounds, detectable polypeptides, electron rich molecules, enzymes capable of generating a detectable signal by action upon a substrate, and radioactive isotopes. Suitable radioactive isotopes include $^{32}$P, $^{35}$S, $^{14}$C, $^{15}$N and $^{125}$I. Fluorescent molecules suitable for the present invention include, but are not limited to, fluorescein and its derivatives, rhodamine and its derivatives, texas red, 5'carboxy-fluorescein ("FMA"), 2',7'-dimethoxy-4',5'-dichloro-6-carboxy-fluorescein ("JOE"), N,N,N',N'-tetramethyl-6-carboxy-rhodamine ("TAMRA"), 6'carboxy-X-rhodamine ("ROX"), HEX, TET, IRD40, and IRD41. Fluroescent molecules that are suitable for the invention further include: cyamine dyes, including by not limited to Cy3, Cy3.5 and Cy5; BODIPY dyes including but not limited to BODIPY-FL, BODIPY-TR, BODIPY-TMR, BODIPY-630/650, and BODIPY-650/670; and ALEXA dyes, including but not limited to ALEXA-488, ALEXA-532, ALEXA-546, ALEXA-568, and ALEXA-594; as well as other fluorescent dyes which will be known to those who are skilled in the art. Electron rich indicator molecules suitable for the present invention include, but are not limited to, ferritin, hemocyanin, and colloidal gold. Alternatively, in less some embodiments the target polynucleotides may be labeled by specifically complexing a first group to the polynucleotide. A second group, covalently linked to an indicator molecules and which has an affinity for the first group, can be used to indirectly detect the target polynucleotide. In such an embodiment, compounds suitable for use as a first group include, but are not limited to, biotin and iminobiotin. Compounds suitable for use as a second group include, but are not limited to, avidin and streptavidin.

In a specific embodiment, the target polynucleotides are prepared as follows: 2 µg Oligo-dT primers are annealed to 2 µg of mRNA isolated from a blood sample of a patient in a total volume of 15 µl, by heating to 70° C. for 10 min, and cooled on ice. The mRNA is reverse transcribed by incubating the sample at 42° C. for 1.5-2 hours in a 100 µl volume containing a final concentration of 50 mM Tris-HCl (pH 8.3), 75 mM KCl, 3 mM MgCl$_2$, 25 mM DTT, 25 mM unlabeled dNTPs, 400 units of Superscript II (200 U/µL, Gibco BRL), and 15 mM of Cy3 or Cy5 (Amersham). RNA is then degraded by addition of 15 µl of 0.1N NaOH, and incubation at 70 DC for 10 min. The reaction mixture is neutralized by addition of 15 µl of 0.1N HCl, and the volume is brought to 500 µl with TE (1 OmM Tris, 1 mM EDTA), and 20 Dg of Cotl human DNA (Gibco-BRL) is added.

The labeled target polynucleotide molecules are purified by centrifugation in a Centricon-30 micro-concentrator (Amicon). If two different target polynucleotide samples (e.g., two samples derived from a healthy patient vs. patient with a disease) are being analyzed and compared by hybridization to the same array, each target nucleic acid sample is labeled with a different fluorescent label (e.g., Cy3 and Cy5) and separately concentrated. The separately concentrated target nucleic acid samples (Cy3 and Cy5 labeled) are combined into a fresh centricon, washed with 500 µl TE, and concentrated again to a volume of less than 7 µl. 1 µL of 1 Oµg/µl polyA RNA (Sigma, #P9403) and 1 µl of 1 Oµg/µl tRNA (Gibco-BRL, #15401-011) is added and the volume is adjusted to 9.5 µl with distilled water. For final target polynucleotide preparation 2.1 µl 20×SSC (1.5M NaCl, 150 mM NaCitrate (pH8.0)) and 0.35 µl 10% SDS is added.

5.3.1.3 Hybridization to Microarrays

In some embodiments, nucleic acid hybridization and wash conditions are chosen so that the polynucleotide molecules to be analyzed by the invention (e.g., "target polynucleotide molecules) specifically bind or specifically hybridize to the complementary polynucleotide sequences of the array, typically to a specific array site, where its complementary DNA is located.

Arrays containing double-stranded probe DNA situated thereon can be subjected to denaturing conditions to render the DNA single-stranded prior to contacting with the target polynucleotide molecules. Arrays containing single-stranded probe DNA (e.g., synthetic oligodeoxyribonucleic acids) may need to be denatured prior to contacting with the target polynucleotide molecules, e.g., to remove hairpins or dimers which form due to self complementary sequences.

Optimal hybridization conditions will depend on the length (e.g., oligomer versus polynucleotide greater than 200 bases) and type (e.g., RNA, or DNA) of probe and target nucleic acids. General parameters for specific (i.e., stringent) hybridization conditions for nucleic acids are described in Sambfook et ah, (supra), and in Ausubel et ah, 1987, *Current Protocols in Molecular Biology*, Greene Publishing and Wiley-Interscience, New York. When the cDNA microarrays of Schena et al. are used, typical hybridization conditions are hybridization in 5×SSC plus 0.2% SDS at 65° C. for four hours, followed by washes at 25° C. in low stringency wash buffer (1×SSC plus 0.2% SDS), followed by 10 minutes at 25° C. in higher stringency wash buffer (0.1×SSC plus 0.2% SDS) (Shena et al, 1996, *Proc. Natl. Acad. Sci. U.S.A.* P3: 10614). Useful hybridization conditions are also provided in, e.g., Tijessen, 1993, *Hybridization With Nucleic Acid Probes*, Elsevier Science Publishers B.V. and Kricka, 1992, Nonisotopic DNA Probe Techniques, Academic Press, San Diego, Calif.

Representative hybridization conditions for use with the screening and/or signaling chips in accordance with some embodiments of the present invention include hybridization at a temperature at or near the mean melting temperature of the probes (e.g., within 5° C., more typically within 2° C.) in 1 M NaCl, 50 mM MES buffer (pH 6.5), 0.5% sodium Sarcosine and 30% formamide.

In a specific embodiment, a labeled target polynucleotide molecules are denatured by heating for two minutes at 100° C., and incubated at 37° C. for 20-30 min before being placed on a nucleic acid array under a 22 mm×22 mm glass cover slip. Hybridization is carried out at 65° C. for fourteen to eighteen hours in a custom slide chamber with humidity maintained by a small reservoir of 3×SSC. The array is washed by submersion and agitation for between two and five minutes in 2×SSC with 0.1% SDS, followed by 1×SSC, and 0.1×SSC. Finally, the array is dried by centrifugation for 2 min in a slide rack in a Beckman GS-6 tabletop centrifuge in Microplus carriers at 650 RPM for two minutes.

5.3.1.4 Signal Detection and Data Analysis

It will be appreciated that when target sequences, e.g., cDNA or cRNA, complementary to the RNA of a blood sample is made and hybridized to a microarray under suitable hybridization conditions, the level of hybridization to the site in the array corresponding to an exon of any particular gene will reflect the prevalence in the cell of mRNA or mRNAs containing the exon transcribed from that gene. For example, when detectably labeled (e.g., with a fluorophore) cDNA complementary to the total cellular mRNA is hybridized to a microarray, the site on the array corresponding to an exon of a gene (i.e., capable of specifically binding the product or products of the gene expressing) that is not transcribed or is removed during RNA splicing in the cell will have little or no signal (e.g., fluorescent signal), and an exon of a gene for which the encoded mRNA expressing the exon is prevalent will have a relatively strong signal. The relative abundance of different mRNAs produced from the same gene by alternative splicing is then determined by the signal strength pattern across the whole set of exons monitored for the gene.

Generally, any form of image processing may be used to digitize the microarrays and thereby obtain high throughput data for molecular markers in the present invention. For example, any of the image processing techniques described or referenced in Draghici, *Data Analysis Tools For DNA Microarrays,* 2003, Chapman & Hall, CRC Press, New York, pp. 33-58, which is hereby incorporated by reference in its entirety, can be used. In some embodiments, two-color fluorescence is used. The use of a two-color fluorescence labeling and detection scheme to define alterations in gene expression has been described in connection with detection of mRNAs, e.g., in Shena et al, 1995, Science 270:467-470, which is hereby incorporated by reference in its entirety for all purposes. The scheme is equally applicable to labeling and detection of exons. An advantage of using target sequences, e.g., cDNAs or cRNAs, labeled with two different fluorophores is that a direct and internally controlled comparison of the mRNA or exon expression levels corresponding to each arrayed gene in two states can be made, and variations due to minor differences in experimental conditions {e.g., hybridization conditions) will not affect subsequent analyses.

In a specific embodiment, the labeled probes are scanned using a GMS Scanner 418 and Scananlzyer software (Michael Eisen, Stamford University), followed by Gene-Spring software (Silicon Genetics, CA) analysis. In another embodiment, a GMS Scanner 428 and Jaguar software are used followed by GeneSpring software analysis. In some embodiments a normalization routine, such as any of the normalization routines described in Section 5.7, is used.

5.3.2 RT-PCR and Quantitative RT-PCR

In one aspect of the invention, the abundance or level of expression of an RNA product of a molecular marker can be measured performing reverse transcription on the RNA from blood and subsequently amplifying the resulting product ("RT-PCR"). In another embodiment, the abundance or level of expression of RNA can be measured from a blood sample by using quantitative RT-PCR or real time PCR ("QRT-PCR") on cDNA copy of RNA. Total RNA, or mRNA from a blood sample can be used as a template and a primer specific to the transcribed portion of a gene of the invention is used to initiate reverse transcription. Methods of reverse transcribing RNA into cDNA are well known and described in, for example, Sambrook et al., 1989, supra. Primer design can be accomplished utilizing commercially available software (e.g., Primer Designer 1.0, academic software, etc.). The product of the reverse transcription is subsequently used as a template for PCR. In one embodiment, a one step process can be used for either the RT-PCR and/or the QRT-PCR (combining the reverse transcription and PCR in a single reaction). In another embodiment, a two step process can be used for either the RT-PCR and/or the QRT-PCR (first doing the reverse transcription step and subsequently performing the PCR). In some embodiments, oligo(dT)-primed first strand cDNA synthesis is performed so as to specifically target the mRNA population (e.g. using the Applied Biosystems High Capacity cDNA Archive Kit (cat #4322171), on a Perkin-Elmer DNA Thermal Cycler.

For quantitative RT-PCR, in some embodiments the reportable value is the Ct-value, which is the threshold cycle at which PCR is in the logarithmic phase. For each gene of interest in each RNA sample, a $\Delta$Ct value can be calculated by the formula: $\Delta Ct=(Ct, \text{target gene})-(Ct,\beta\text{-actin})$. The $\Delta$Ct values from different groups of RNA samples can then be compared by the Mann-Whitney Rank Sum test.

In some embodiments, Quantitative RT-PCR can be done using probes including Taqman® probes (Perkin Elmer, Foster City, Calif.), The probe is specific for the PCR product and has both a quencher and fluorescent reporter attached to the probe. Different fluorescent markers can be utilized. In some embodiments, multiple probes can be used in the quantitative RT-PCR process to allow for multiplexing reactions (e.g. allow for measurement of two molecular markers in one reaction well or container). When using TaqMan® probes, Taq DNA polymerase is used which has 5'-to-3' exonuclease activity and thus will cleave of the fluorescent reporter of the probe, freeing the fluorescent molecular from the quencher molecule. Thus the emission of fluorescence is used to measure the amount of PCR product being made. Other probes are also useful for quantitative RT-PCR including Molecular Beacons®.

Other known techniques for quantitative Rt-PCR is to use an intercalating dye such as the commercially available QuantiTect™ SYBR® Green PCR (Qiagen, Valencia Calif.).

Additionally, other systems to quantitatively measure mRNA expression products are known including Scorpions® (Zeneca Limited) or Fluorescent Polarization Probes (see e.g. *Zeneca Limited,* 6,007,984) etc.

5.3.3 Nuclease Protection Assays

Nuclease protection assays (including both ribonuclease protection assays and S1 nuclease assays) can be used to detect and quantify specific products of molecular markers. In nuclease protection assays, an antisense probe (labeled with, e.g., radiolabeled or nonisotopic) hybridizes in solution to an RNA sample. Following hybridization, single-stranded, unhybridized probe and RNA are degraded by nucleases. An acrylamide gel is used to separate the remaining protected fragments. Typically, solution hybridization is more efficient than membrane-based hybridization, and it can accommodate up to 100 µg of sample RNA, compared with the 20-30 µg maximum of blot hybridizations.

The ribonuclease protection assay, which is the most common type of nuclease protection assay, requires the use of RNA probes. Oligonucleotides and other single-stranded DNA probes can only be used in assays containing S1 nuclease. The single-stranded, antisense probe must typically be completely homologous to target RNA to prevent cleavage of the probeitarget hybrid by nuclease.

5.3.4 Mass Spectrometry

Mass spectrometry (e.g., electrospray ionization "ESI", matrix-assisted laser desorption-ionization "MALDI", and Fourier-transform ion cyclotron resonance "FT-ICR") can be used to measure data (e.g., mass, charge) of molecular markers in blood samples. Such molecular markers that can be characterized by mass spectrometry include but are not limited to, proteins, nucleic acids, carbohydrates, and other biological macromolecules. This section provides brief and non-limiting examples of mass spectrometry techniques that can be used to quantitatively characterize molecular markers.

MALDI uses a pulsed laser for desorption of the ions and a time-of-flight analyzer and has been used for the detection of noncovalent tRNA:amino-acyl-tRNA synthetase complexes. See, for example, Gruic-Sovulj et al., 1997, J. Biol. Chem. 272:32084. ESI mass spectrometry ("ESI-MS") has been used for studying non-covalent molecular interactions. ESI-MS generates molecular ions with little to no fragmentation. See, for example, Xavier et al., 2000, Trends Biotechnol. 18:349. Fourier-transform ion cyclotron resonance ("FT-ICR") mass spectrometry provides high-resolution spectra, isotope-resolved precursor ion selection, and accurate mass assignments. See, for example, Xavier et al., 2000, Trends Biotechnol. 18:349.

Tandem mass spectrometry is described in Link et al., 1999, Nat. Biotechnol. 17, 676-682; Washburn et al. 2001, Nat. Biotechnol. 19, 242; Gaven et al., 2002, Nature 415, 141;

and Ho et al., 2002, Nature 418, 180). In the case of proteins from a blood sample, the proteins can first be digested into peptides using an enzyme such as trypsin and then subjected to liquid chromatography tandem mass spectrometry (MS/MS). Liquid chromatography provides an initial separation of the peptides, which are then ionized directly into a mass spectrometer. Following an initial scan in which the mass/charge ratio of all intact (parent) ions from the peptides are measured, the mass spectrometer selects a parent ion, fragments it and obtains the mass spectrum of the generated fragments. These fragmentation patterns are called tandem mass spectra or MS/MS spectra. This process of ion selection and fragmentation is repeated throughout the liquid chromatography separation, thus generating a set of time resolved MS/MS spectra, with each spectrum representing a species eluting at a particular time from the LC separation. The resolving power of the liquid chromatography step, combined with the high mass resolution of modern mass spectrometers typically assures that each MS/MS spectrum represents the fragmentation pattern of a unique peptide in the digest.

5.3.5 Comparative Gene Expression Profiling

In some embodiments of the present invention quantitative measurement of molecular marker data is performed using comparative gene-expression profiling. An example of such technology is the multiplex microsphere bead assay used by Fuja et al., 2004, Journal of Biotechnology 108, 193.

5.3.6 Transcription Based Amplification Systems

In another aspect of the invention, the level of expression of a molecular marker in blood can be measured by amplifying RNA from a blood sample using transcription based amplification systems (TAS), including nucleic acid sequence amplification (NASBA) and 3SR. See, e.g., Kwoh et al., 1989, PNAS USA 86:1173; International Publication No. WO 88/10315; and U.S. Pat. No. 6,329,179. In NASBA, the nucleic acids can be prepared for amplification using conventional phenol/chloroform extraction, heat denaturation, treatment with lysis buffer and minispin columns for isolation of DNA and RNA or guanidinium chloride extraction of RNA. These amplification techniques involve annealing a primer that has target specific sequences. Following polymerization, DNA/RNA hybrids are digested with RNase H while double stranded DNA molecules are heat denatured again. In either case, the single stranded DNA is made fully double stranded by addition of second target specific primer, followed by polymerization. The double-stranded DNA molecules are then multiply transcribed by a polymerase such as T7 or SP6. In an isothermal cyclic reaction, the RNA's are reverse transcribed into double stranded DNA, and transcribed once with a polymerase such as T7 or SP6. The resulting products, whether truncated or complete, indicate target specific sequences.

5.3.7 Additional Techniques for Detecting and Quantifying RNA

Many other techniques are known to one of skill for detecting and measuring RNA and can be used in accordance with the methods of the invention. Non-limiting examples of such techniques include Northern blotting, nuclease protection assays, RNA fingerprinting, polymerase chain reaction, ligase chain reaction, Qbeta replicase, isothermal amplification method, strand displacement amplification, transcription based amplification systems, nuclease protection (SI nuclease or RNAse protection assays) as well as methods disclosed in International Publication Nos. WO 88/10315 and WO 89/06700, and International Applications Nos. PCT/US87/00880 and PCT/US 89/01025.

A standard Northern blot assay can be used to ascertain an RNA transcript size, identify alternatively spliced RNA transcripts, and the relative amounts of mRNA in a blood sample, in accordance with conventional Northern hybridization techniques known to those persons of ordinary skill in the art. In Northern blots, RNA samples are first separated by size via electrophoresis in an agarose gel under denaturing conditions. The RNA is then transferred to a membrane, crosslinked and hybridized with a labeled probe. Nonisotopic or high specific activity radiolabeled probes can be used including random-primed, nick-translated, or PCR-generated DNA probes, in vitro transcribed RNA probes, and oligonucleotides. Additionally, sequences with only partial homology (e.g., cDNA from a different species or genomic DNA fragments that might contain an exon) may be used as probes. The labeled probe, e.g., a radiolabeled cDNA, either containing the full-length, single stranded DNA or a fragment of that DNA sequence may be at least 20, at least 30, at least 50, or at least 100 consecutive nucleotides in length. The probe can be labeled by any of the many different methods known to those skilled in this art. The labels most commonly employed for these studies are radioactive elements, enzymes, chemicals that fluoresce when exposed to ultraviolet light, and others. A number of fluorescent materials are known and can be utilized as labels. These include, but are not limited to, fluorescein, rhodamine, auramine, Texas Red, AMCA blue and Lucifer Yellow. A articular detecting material is anti-rabbit antibody prepared in goats and conjugated with fluorescein through an isothiocyanate. Proteins can also be labeled with a radioactive element or with an enzyme. The radioactive label can be detected by any of the currently available counting procedures. Non-limiting examples of isotopes include 3H, 14C, 32P, 35S, 36Cl, 51Cr, 57Co, 58Co, 59Fe, 9OY, 1251, 1311, and 186Re. Enzyme labels are likewise useful, and can be detected by any of the presently utilized calorimetric, pectrophotometric, fluorospectrophotometric, amperometric or gasometric techniques. The enzyme is conjugated to the selected particle by reaction with bridging molecules such as carbodiimides, diisocyanates, glutaraldehyde and the like. Any enzymes known to one of skill in the art can be utilized. Examples of such enzymes include, but are not limited to, peroxidase, beta-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

Nuclease protection assays (including both ribonuclease protection assays and S1 nuclease assays) can be used to detect and quantitate specific mRNAs. In nuclease protection assays, an antisense probe (labeled with, e.g., radiolabeled or nonisotopic) hybridizes in solution to an RNA sample. Following hybridization, single-stranded, unhybridized probe and RNA are degraded by nucleases. An acrylamide gel is used to separate the remaining protected fragments. Typically, solution hybridization is more efficient than membrane-based hybridization, and it can accommodate up to 100 µg of sample RNA, compared with the 20-30 µg maximum of blot hybridizations.

The ribonuclease protection assay, which is the most common type of nuclease protection assay, requires the use of RNA probes. Oligonucleotides and other single-stranded DNA probes can only be used in assays containing S1 nuclease. The single-stranded, antisense probe must typically be completely homologous to target RNA to prevent cleavage of the probe:target hybrid by nuclease.

Additional techniques to quantitatively measure RNA expression include, but are not limited to, ligase chain reaction, Qbeta replicase (see, e.g., International Application No. PCT/US87/00880), isothermal amplification method (see, e.g., Walker et al., 1992, PNAS 89:382-396), strand displacement amplification (SDA), repair chain reaction, Asymmetric Quantitative PCR (see, e.g., U.S. Publication No. US200330134307A1) and the multiplex microsphere bead assay described in Fuja et al., 2004, Journal of Biotechnology 108:193-205.

5.3.7.1 Separation of Amplification Products

Some of the quantitative measurement techniques described above may require separation of amplification products. Several techniques can be used to separate such amplification products. For example, amplification products can be separated by agarose, agarose-acrylamide or polyacrylamide gel electrophoresis using conventional methods. Several techniques for detecting PCR products quantitatively without electrophoresis can also be used according to the invention. See, for example, *CR Protocols, A Guide to Methods and Applications*, Innis et aL, Academic Press, Inc. N.Y., 1990). For example, chromatographic techniques can be employed to effect separation. There are many kinds of chromatography that can be used in the present invention: adsorption, partition, ion-exchange and molecular sieve, HPLC, and many specialized techniques for using them including column, paper, thin-layer and gas chromatography (Freifelder, Physical Biochemistry Applications to Biochemistry and Molecular Biology, 2nd ed., Wm. Freeman and Co., New York, N.Y., 1982).

Another example of a separation methodology is done by covalently labeling the oligonucleotide primers used in a PCR reaction with various types of small molecule ligands. In one such separation, a different ligand is present on each oligonucleotide. A molecule, perhaps an antibody or avidin if the ligand is biotin, that specifically binds to one of the ligands is used to coat the surface of a plate such as a 96 well ELISA plate. Upon application of the PCR reactions to the surface of such a prepared plate, the PCR products are bound with specificity to the surface. After washing the plate to remove unbound reagents, a solution containing a second molecule that binds to the first ligand is added. This second molecule is linked to some kind of reporter system. The second molecule only binds to the plate if a PCR product has been produced whereby both oligonucleotide primers are incorporated into the final PCR products. The amount of the PCR product is then detected and quantified in a commercial plate reader much as ELISA reactions are detected and quantified. An ELISA-like system such as the one described here has been developed by the Raggio Italgene company under the C-Track trade name.

5.3.7.2 Visualization of Amplification Products

Some of the quantitative measurement techniques described above may require visualization of amplification products. Amplification products are visualized, for example, in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products may then be exposed to x-ray film or visualized under the appropriate stimulating spectra, following separation.

In one embodiment, visualization is achieved indirectly. Following separation of amplification products, a labeled, nucleic acid probe is brought into contact with the amplified marker sequence. The probe preferably is conjugated to a chromophore but may be radiolabeled. In another embodiment, the probe is conjugated to a binding partner, such as an antibody or biotin, where the other member of the binding pair carries a detectable moiety.

In another embodiment, detection is by Southern blotting and hybridization with a labeled probe. The techniques involved in Southern blotting are well known to those of skill in the art and may be found in many standard books on molecular protocols. See Sambrook et al., 1989. Briefly, amplification products are separated by gel electrophoresis. The gel is then contacted with a membrane, such as nitrocellulose, permitting transfer of the nucleic acid and non-covalent binding. Subsequently, the membrane is incubated with a chromophore-conjugated probe that is capable of hybridizing with a target amplification product. Detection is by exposure of the membrane to x-ray film or ion-emitting detection devices.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

5.4 Methods for Measuring Molecular Marker Data Reflective of Abundance of Protein Products of Molecular Markers Measurement of the abundance of protein products of molecular markers in blood may be performed using a number of separation techniques combined with a monitoring system. For example, whole genome monitoring of protein (e.g., the "proteome,") can be carried out using commercial systems such as a SELDI® Chip by Ciphergen. In addition, protein microarrays comprised of immobilized, preferably monoclonal, antibodies specific to a plurality of protein species encoded by the cell genome can be used, (e.g., The ProteinChip® Biomarker System, Ciphergen, Fremont, Calif.). See also, for example, Lin, 2004, Modern Pathology, 1-9; Li, 2004, Journal of Urology 171, 1782-1787; Wadsworth, 2004, Clinical Cancer Research, 10, 1625-1632; Prieto, 2003, Journal of Liquid Chromatography & Related Technologies 26, 2315-2328; Coombes, 2003, Clinical Chemistry 49, 1615-1623; Mian, 2003, Proteomics 3, 1725-1737; Lehre et al, 2003, BJU International 92, 223-225; and Diamond, 2003, Journal of the American Society for Mass Spectrometry 14, 760-765, which are hereby incorporated by reference in their entireties.

In one embodiment, antibodies can be used to measure protein products of the candidate molecular markers. Methods for making monoclonal antibodies are well known (see, e.g., Harlow and Lane, 1988, *Antibodies: A Laboratory Manual*, Cold Spring Harbor, N.Y., which is incorporated in its entirety for all purposes). In one embodiment, monoclonal antibodies are raised against synthetic peptide fragments designed based on genomic sequence of the cell. With such an antibody array, proteins from the cell are contacted to the array and their binding is assayed with assays known in the art.

Immunoassays known to one of skill in the art can be used to detect and quantify protein levels. For example, ELISAs can be used to detect and quantify protein levels. ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. In a preferred embodiment, an ELISA may be performed by coating a high binding 96-well microtiter plate (Costar) with 2 µg/ml of rhu-IL-9 in PBS overnight. Following three washes with PBS, the plate is incubated with three-fold serial dilutions of Fab at 25° C. for 1 hour. Following another three washes of PBS, 1 µg/ml anti-human kappa-alkaline phosphatase-conjugate is added and the plate is incubated for 1 hour at 25° C. Following three washes with PBST, the alkaline phosphatase activity is determined in 50 µl/AMP/PPMP substrate. The reactions are stopped and the absorbance at 560 nm is determined with a VMAX microplate reader. For further discussion regarding ELISAs see, e.g., Ausubel et al, eds, 1994, Current Protocols in Molecular Biology, Vol. 1, John Wiley & Sons, Inc., New York at 11.2.1.

Protein levels may be determined by Western blot analysis. Further, protein levels as well as the phosphorylation of proteins can be determined by immunoprecitation followed by Western blot analysis. Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1 to 4 hours) at 40° C., adding protein A and/or protein G sepharose beads to the cell lysate, incubating for about an hour or more at 40° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, incubating the membrane in blocking solution (e.g., PBS with 3% BSA or non-fat milk), washing the membrane in washing buffer (e.g., PBS-Tween 20), incubating the membrane with primary antibody (the antibody of interest) diluted in blocking buffer, washing the membrane in washing buffer, incubating the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}P$ or $^{125}I$) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

Protein expression levels can also be separated by two-dimensional gel electrophoresis systems. Two-dimensional gel electrophoresis is well-known in the art and typically involves isoelectric focusing along a first dimension followed by SDS-PAGE electrophoresis along a second dimension. See, e.g., Hames et al, 1990, *Gel Electrophoresis of Proteins: A Practical Approach*, IRL Press, New York; Shevchenko et al., 1996, *Proc. Natl. Acad. ScL USA* 93:1440-1445; Sagliocco et al., 1996, *Yeast* 12:1519-1533; Lander, 1996, *Science* 274:536-539. The resulting electropherograms can be analyzed by numerous techniques, including mass spectrometric techniques, Western blotting and immunoblot analysis using polyclonal and monoclonal antibodies, and internal and N-terminal micro-sequencing.

5.5 Uses of Classifiers Identified

In exemplary embodiments, the classifiers constructed in accordance with the present invention can be used to detect, diagnose, prognose and/or monitor a trait in a test individual. In a specific embodiment, a classifier or classifier group constructed in accordance with Section 5.1 is used to detect, diagnose, prognose and/or monitor a disease in said test individual. In another embodiment, a classifier or classifier group constructed in accordance with Section 5.1 is used to detect, diagnose, prognose and/or monitor a reoccurrence of disease in said test individual. In another embodiment, a classifier or classifier group constructed in accordance with the invention is used to evaluate or predict the efficacy of treatment in a subject. In another embodiment, a classifier or classifier group constructed in accordance with the invention is used to predict whether a subject will be responsive to treatment and/or treatment outcomes. In another embodiment, a classifier or classifier group constructed in accordance with the invention is used to monitor and/or predict treatment compliance or non-compliance. In another embodiment, a classifier or classifier group constructed in accordance with the methods of the invention is indicative of the responsiveness of a subject to a stimulus (whether external or internal, e.g., smoke, pollution, sunlight, heat, and mutations) and is used to evaluate or predict the response of a subject to such stimulus.

In yet another embodiment, the molecular markers identified by the classifiers of the invention can be used independently of the classifier to detect, diagnose, prognose, predict and/or monitor a trait. In such embodiments, said detection, diagnosis, prognosis, prediction and/or monitoring of a test individual can be accomplished by monitoring the gene expression pattern or profile of the molecular markers identified by the classifier or classifier group of the invention of a test individual and comparing said pattern or profile to a gene expression pattern or profile of a control individual or group of individuals who have said trait. In another embodiment, the gene expression pattern or profile of the test individual can be compared with a control individual or group of individuals who do not have said trait. In another embodiment, the gene expression pattern or profile of the test individual is compared as between individuals or group of individuals who have said trait and who do not have said trait. In yet another embodiment, the gene expression pattern or profile of the test individual is compared with the individuals used for the training population. In yet another embodiment, the gene expression pattern or profile of the test individual is compared with the individuals of the scoring population. As used herein, a "gene expression pattern" or "gene expression profile" indicates the combined pattern of the results of the analysis of the level of expression of two or more biomarkers of the invention including 3, 4, 5, 6, 7, 8, 9, 10, 11, 12 or all of the biomarkers of the classifier or classifier groups. A gene expression pattern or gene expression profile can result from the measurement of expression of the products of the biomarkers of the invention and can be done by measuring either the RNA or the proteins corresponding to said molecular marker using any of the techniques described herein. For example techniques to measure expression of the RNA products of the biomarkers of the invention includes, PCR based methods (including RT-PCR and quantitative RT-PCR) and non PCR based method as well as microarray analysis. To measure protein products of the biomarkers of the invention, techniques include western blotting and ELISA analysis.

5.6 Kits

One embodiment of the present invention comprises kits for measuring molecular marker data by providing the materials necessary to measure the abundance of one or more of the products of one or more molecular markers of the classifier or classifier groups identified. Such kits may comprise materials and reagents required for measuring molecular marker data where the product of the molecular marker is RNA or protein. In some embodiments, such kits include microarrays wherein the microarray is comprised of oligonucleotides and/or DNA and/or RNA fragments which hybridize to one or more of the products of one or more of the molecular markers of a classifier or classifier group. In some embodiments, such kits may include primers for PCR of either the RNA product or the cDNA copy of the RNA product of the molecular marker or both. In some embodiments, such kits may include primers for PCR as well as probes for Quantitative PCR. In some embodiments, such kits may include multiple primers and multiple probes wherein some of said probes have different flourophores so as to permit multiplexing of multiple products of a single molecular marker or multiple products wherein each product results from a single molecular marker. In some embodiments, such kits may further include materials and reagents for creating cDNA from RNA. In some embodiments, such kits may include antibodies specific for the protein products of a molecular marker. Such kits may additionally comprise materials and reagents for isolating RNA and/or proteins from a blood sample. Such kits may additionally comprise materials and reagents for isolating RNA and/or proteins from a non-blood tissue sample. In addition such kits may include materials and reagents for synthesizing cDNA from RNA isolated from a blood sample. In some embodiments of the present invention such kits may include, a computer program product embedded on computer readable media for determining whether a subject has a trait of interest. In some embodiments of the present invention, the kits of the invention may include a computer program product embedded on a computer readable media along with instructions.

In some embodiments, the invention provides kits for measuring the expression of one or more nucleic acid sequences of one or more molecular markers. In a specific embodiment, such kits measure the expression of one or more nucleic acid sequences associated with a molecular marker which has been determined according to the method of the invention as being indicative of a trait of interest. In accordance with this embodiment, the kits may comprise materials and reagents that are necessary for measuring the expression of particular nucleic acid sequence products of molecular markers identified by a classifier or classifier group of the invention. For example, a microarray or RT-PCR kit may be produced for a specific condition and contain only those reagents and materials necessary for measuring the levels of specific RNA transcript products of the molecular markers associated with the classifier or classifier groups selected in accordance with one embodiment of the invention. Alternatively, in some embodiments, the kits can comprise materials and reagents that are not limited to those required to measure the expression of particular nucleic acid sequences of any particular molecular marker. For example, in certain embodiments, the kits comprise materials and reagents necessary for measuring the levels of expression of 1, 2, 3, 4, 5, 6, 7, 8, 9, 10, 15, 20, 25, 30, 35, 40, 45, 50 or more of the molecular markers of the invention, in addition to reagents and materials necessary for measuring the levels of the expression of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50 or more genes other than the molecular markers of the invention. In other embodiments, the kits contain reagents and materials necessary for measuring the levels of expression of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50 or more of the molecular markers of the invention, and 1, 2, 3, 4, 5, 10, 15, 20, 25, 30, 35, 40, 45, 50, 55, 60, 65, 70, 75, 80, 85, 90, 95, 100, 125, 150, 175, 200, 225, 250, 300, 350, 400, 450, or more genes that are not molecular markers of the invention, or 1-10, 1-100, 1-150, 1-200, 1-300, 1-400, 1-500, 1-1000, 25-100, 25-200, 25-300, 25-400, 25-500, 25-1000, 100-150, 100-200, 100-300, 100-400, 100-500, 100-1000 or 500-1000 genes that are not molecular markers of the invention.

For nucleic acid microarray kits, the kits generally comprise probes attached to a solid support surface. In one such embodiment, probes can be either oligonucleotides or longer length probes including probes ranging from 150 nucleotides in length to 800 nucleotides in length. The probes may be labeled with a detectable label. In a specific embodiment, the probes are specific for one or more of the products of a specific molecular marker identified following the methods of section 5.1. The microarray kits may comprise instructions for performing the assay and methods for interpreting and analyzing the data resulting from the performance of the assay. In a specific embodiment, the kits comprise instructions for diagnosing a trait of interest. The kits may also comprise hybridization reagents and/or reagents necessary for detecting a signal produced when a probe hybridizes to a target nucleic acid sequence. Generally, the materials and reagents for the microarray kits are in one or more containers. Each component of the kit is generally in its own a suitable container.

In certain embodiments, a nucleic acid microarray kit comprises materials and reagents necessary for measuring the levels of expression of 1, 2, 3, 4, 5, 6, 7, 8, 9, 10, 15, 20, 25, 30, 35, 40, 45, 50 or more of the molecular markers of the invention, in addition to reagents and materials necessary for measuring the levels of the expression of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50 or more genes other than the molecular markers of the invention. In other embodiments, a nucleic acid microarray kit contains reagents and materials necessary for measuring the levels of expression of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50 or more of the molecular markers of the invention, and 1, 2, 3, 4, 5, 10, 15, 20, 25, 30, 35, 40, 45, 50, 55, 60, 65, 70, 75, 80, 85, 90, 95, 100, 125, 150, 175, 200, 225, 250, 300, 350, 400, 450, or more genes that are not molecular markers of the invention, or 1-10, 1-100, 1-150, 1-200, 1-300, 1-400, 1-500, 1-1000, 25-100, 25-200, 25-300, 25-400, 25-500, 25-1000, 100-150, 100-200, 100-300, 100-400, 100-500, 100-1000 or 500-1000 genes that are not molecular markers of the invention.

For Quantitative PCR, the kits generally comprise preselected primers specific for particular nucleic acid sequences. The Quantitative PCR kits may also comprise enzymes suitable for amplifying nucleic acids (e.g., polymerases such as Taq), and deoxynucleotides and buffers needed for the reaction mixture for amplification. The Quantitative PCR kits may also comprise probes specific for the nucleic acid sequences associated with or indicative of a condition. The probes may or may not be labeled with a flourophore. The probes may or may not be labeled with a quencher molecule. In some embodiments the Quantitative PCR kits also comprise components suitable for reverse-transcribing RNA including enzymes (e.g. reverse transcriptases such as AMV, MMLV and the like) and primers for reverse transcription along with deoxynucleotides and buffers needed for the reverse transcription reaction. Each component of the quantitative PCR kit is generally in its own suitable container. Thus, these kits generally comprise distinct containers suitable for each individual reagent, enzyme, primer and probe. Further, the quantitative PCR kits may comprise instructions for performing the assay and methods for interpreting and analyzing the data resulting from the performance of the assay. In a specific embodiment, the kits contain instructions for diagnosing a trait of interest.

For antibody based kits, the kit can comprise, for example: (1) a first antibody (which may or may not be attached to a solid support) which binds to a peptide, polypeptide or protein of interest; and, optionally, (2) a second, different antibody which binds to either the peptide, polypeptide or protein, or the first antibody and is conjugated to a detectable label (e.g., a fluorescent label, radioactive isotope or enzyme). In a specific embodiment, the peptide, polypeptide or protein of interest is associated with or indicative of a condition (e.g., a disease). The antibody-based kits may also comprise beads for conducting an immunoprecipitation. Each component of the antibody-based kits is generally in its own suitable container. Thus, these kits generally comprise distinct containers suitable for each antibody. Further, the antibody-based kits may comprise instructions for performing the assay and methods for interpreting and analyzing the data resulting from the performance of the assay. In a specific embodiment, the kits contain instructions for diagnosing a trait of interest.

5.7 Exemplary Normalization Routines

A number of different normalization protocols can be used to normalize molecular marker data obtained using microarrays. Some such normalization protocols are described in this section. Typically, the normalization comprises normalizing the expression level measurement of each gene in a plurality of genes that is expressed by a subject. Many of the normalization protocols described in this section are used to normalize microarray data. It will be appreciated that there are many other suitable normalization protocols that may be used in accordance with the present invention. All such protocols are within the scope of the present invention. Many of the normalization protocols found in this section are found in publicly available software, such as Microarray Explorer (Image Processing Section, Laboratory of Experimental and Computational Biology, National Cancer Institute, Frederick, Md. 21702, USA).

One normalization protocol is Z-score of intensity. In this protocol, raw expression intensities are normalized by the (mean intensity)/(standard deviation) of raw intensities for all spots in a sample. For microarray data, the Z-score of intensity method normalizes each hybridized sample by the mean and standard deviation of the raw intensities for all of the spots in that sample. The mean intensity mnIj and the standard deviation sdIj are computed for the raw intensity of control genes. It is useful for standardizing the mean (to 0.0) and the range of data between hybridized samples to about −3.0 to +3.0. When using the Z-score, the Z differences ($Z_{d}i_j$) are computed rather than ratios. The Z-score intensity (Z-score$_j$) for intensity Iy for probe i (hybridization probe, protein, or other binding entity) and spot j is computed as:

$$Z\text{-score}_j = (Iy - rrmli)/sdIj,$$

and $$Zdiff_j(x,y) = Z\text{-score}_{xj} - Z\text{-score}_{yj}.$$

where x represents the x channel and y represents the y channel.

Another normalization protocol is the median intensity normalization protocol in which the raw intensities for all spots in each sample are normalized by the median of the raw intensities. For microarray data, the median intensity normalization method normalizes each hybridized sample by the median of the raw intensities of control genes (median $\pi$) for all of the spots in that sample. Thus, upon normalization by the median intensity normalization method, the raw intensity $I_{ij}$ for probe i and spot j, has the value Iiny where, $$Imy = (Iy/medianIi).$$

Another normalization protocol is the log median intensity protocol. In this protocol, raw expression intensities are normalized by the log of the median scaled raw intensities of representative spots for all spots in the sample. For microarray data, the log median intensity method normalizes each hybridized sample by the log of median scaled raw intensities of control genes (medianIj) for all of the spots in that sample. As used herein, control genes are a set of genes that have reproducible accurately measured expression values. The value 1.0 is added to the intensity value to avoid taking the log(O.O) when intensity has zero value. Upon normalization by the median intensity normalization method, the raw intensity $I_{ij}$ for probe i and spot j, has the value Imy where, $$Imjj = \log(1.0 + (Ijj/medianIi)).$$

Yet another normalization protocol is the Z-score standard deviation log of intensity protocol. In this protocol, raw expression intensities are normalized by the mean log intensity (mnLIj) and standard deviation log intensity (sdLIj). For microarray data, the mean log intensity and the standard deviation log intensity is computed for the log of raw intensity of control genes. Then, the Z-score intensity ZlogSy for probe i and spot j is:

$$Z \log Sj_j = (\log(Ii_j) - mnLIi)/sdLIi.$$

Still another normalization protocol is the Z-score mean absolute deviation of log intensity protocol. In this protocol, raw expression intensities are normalized by the Z-score of the log intensity using the equation (log(intensity)−mean logarithm)/standard deviation logarithm. For microarray data, the Z-score mean absolute deviation of log intensity protocol normalizes each bound sample by the mean and mean absolute deviation of the logs of the raw intensities for all of the spots in the sample. The mean log intensity mnLIj and the mean absolute deviation log intensity madLI, are computed for the log of raw intensity of control genes. Then, the Z-score intensity ZlogAy for probe i and spot j is:

$Z \log A_{jj} = (\log(I_{ij}) - mnLIj)/madLIi.$

Another normalization protocol is the user normalization gene set protocol. In this protocol, raw expression intensities are normalized by the sum of the genes in a user defined gene set in each sample. This method is useful if a subset of genes has been determined to have relatively constant expression across a set of samples. Yet another normalization protocol is the calibration DNA gene set protocol in which each sample is normalized by the sum of calibration DNA genes. As used herein, calibration DNA genes are genes that produce reproducible expression values that are accurately measured. Such genes tend to have the same expression values on each of several different microarray s. The algorithm is the same as user normalization gene set protocol described above, but the set is predefined as the genes flagged as calibration DNA.

Yet another normalization protocol is the ratio median intensity correction protocol. This protocol is useful in embodiments in which a two-color fluorescence labeling and detection scheme is used. In the case where the two fluors in a two-color fluorescence labeling and detection scheme are Cy3 and Cy5, measurements are normalized by multiplying the ratio (Cy3/Cy5) by medianCy5/medianCy3 intensities. If background correction is enabled, measurements are normalized by multiplying the ratio (Cy3/Cy5) by (medianCy5-medianBkgdCy5)/(medianCy3-medianBkgdCy3) where medianBkgd means median background levels.

In some embodiments, intensity background correction is used to normalize measurements. The background intensity data from a spot quantification programs may be used to correct spot intensity. Background may be specified as either a global value or on a per-spot basis. If the array images have low background, then intensity background correction may not be necessary.

5.8 Exemplary Diseases

As discussed supra, the present invention provides methods for developing classifiers that can be used to determine whether a patient has a certain trait including a disease. Exemplary diseases that can be identified include asthma, cancers, common late-onset Alzheimer's disease, diabetes, heart disease, hereditary early-onset Alzheimer's disease (George-Hyslop et al, 1990, Nature 347: 194), hereditary nonpolyposis colon cancer, hypertension, infection, maturity-onset diabetes of the young (Barbosa et al., 1976, Diabete Metab. 2: 160), mellitus, nonalcoholic fatty liver (NAFL) (Younossi, et al, 2002, Hepatology 35, 746-752), nonalcoholic steatohepatitis (NASH) (James & Day, 1998, J. Hepatol. 29: 495-501), non-insulin-dependent diabetes mellitus, and polycystic kidney disease (Reeders et al, 1987, Human Genetics 76: 348).

Disease also includes, blood disorder, blood lipid disease, autoimmune disease, arthritis (including osteoarthritis, rheumatoid arthritis, lupus, allergies, juvenile rheumatoid arthritis and the like), bone or joint disorder, a cardiovascular disorder (including heart failure, congenital heart disease; rheumatic fever, valvular heart disease; cor pulmonale, cardiomyopathy, myocarditis, pericardial disease; vascular diseases such as atherosclerosis, acute myocardial infarction, ischemic heart disease and the like), obesity, respiratory disease (including asthma, pneumonitis, pneumonia, pulmonary infections, lung disease, bronchiectasis, tuburculosis, cystic fibrosis, interstitial lung disease, chronic bronchitis emphysema, pulmonary hypertension, pulmonary thromboembolism, acute respiratory distress syndrome and the like), hyperlipidemias, endocrine disorder, immune disorder, infectious disease, muscle wasting and whole body wasting disorder, neurological disorders (including migraines, seizures, epilepsy, cerebrovascular diseases, alzheimers, dementia, parkinsons, ataxic disorders, motor neuron diseases, cranial nerve disorders, spinal cord disorders, meningitis and the like) including neurodegenerative and/or neuropsychiatric diseases and mood disorders (including schizophrenia, anxiety, bipolar disorder; manic depression and the like, skin disorder, kidney disease, scleroderma, stroke, hereditary hemorrhage telangiectasia, diabetes, disorders associated with diabetes (e.g., PVD), hypertension, Gaucher's disease, cystic fibrosis, sickle cell anemia, liver disease, pancreatic disease, eye, ear, nose and/or throat disease, diseases affecting the reproductive organs, gastrointestinal diseases (including diseases of the colon, diseases of the spleen, appendix, gall bladder, and others) and the like. For further discussion of human diseases, see Mendelian Inheritance in Man: A Catalog of Human Genes and Genetic Disorders by Victor A. McKusick (12th Edition (3 volume set) June 1998, Johns Hopkins University Press, ISBN: 0801857422) and Harrison's Principles of Internal Medicine by Braunwald, Fauci, Kasper, Hauser, Longo, & Jameson (15th Edition 2001), the entirety of which is incorporated herein.

Cancers that can be identified using the inventive techniques of the present invention include, but are not limited to, human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocyte, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease.

5.9 Exemplary Database Architectures

In some embodiments, training population 44, candidate molecular marker data structure 58, patient database 68, and/or classifier database 70 comprise or are stored in one or more data warehouses. Data warehouses are typically structured as either relational databases or multidimensional data cubes. This section describes relational databases and multidimensional data cube architectures that can be used to store training data, candidate molecular marker lists, patient molecular marker data and/or classifiers of the present invention. More information on relational databases and multidimensional data cubes is found in Berson and Smith, 1997, *Data Warehousing, Data Mining and OLAP*, McGraw-Hill, New York; Freeze, 2000, *Unlocking OLAP with Microsoft SQL Server and Excel* 2000, IDG Books Worldwide, Inc., Foster City, Calif.; and Thomson, 1997, *OLAP Solutions: Building Multidimensional Information Systems*, Wiley Computer Publishing, New York.

5.9.1 Data Organization

Databases have typically been used for operational purposes, such as order entry, accounting and inventory control. More recently, corporations and scientific projects have been building databases, called data warehouses or large on-line analytical processing (OLAP) databases, explicitly for the purposes of exploration and analysis. The "data warehouse" can be described as a subject-oriented, integrated, time-variant, nonvolatile collection of data in support of management decisions. Data warehouses are built using both relational databases and specialized multidimensional structures called data cubes. In some embodiments a database stored in computer 10 or stored in a computer addressable by computer 10 across wide area network 34 is a relational database or a datacube.

5.9.2 Relational Databases

Relational databases organize data into tables where each row corresponds to a basic entity or fact and each column represents a property of that entity. For example, a table can represent transactions in a bank, where each row corresponds to a single transaction, and each transaction has multiple attributes, such as the transaction amount, the account balance, the bank branch, and the customer. The relational table is referred to as a relation, a row as a tuple, and a column as an attribute or field. The attributes within a relation can be partitioned into two types: dimensions and measures. Dimensions and measures are similar to independent and dependent variables in traditional analysis. For example, the bank branch and the customer would be dimensions, while the account balance would be a measure. A single relational database will often describe many heterogeneous but interrelated entities. For example, a database designed for a restaurant chain might maintain information about employees, products, and sales. The database schema defines the relations in a database, the relationships between those relations, and how the relations classify the entities of interest.

5.9.3 Data Cubes

A data warehouse can be constructed as a relational database using either a star or snowflake schema and will provide a conceptual classifier of a multidimensional data set. Each axis in the corresponding data cube represents a dimension in a relational schema and consists of every possible value for that dimension. For example, an axis corresponding to states would have fifty values, one for each state. Each cell in the data cube corresponds to a unique combination of values for the dimensions. For instance, if there are two dimensions, "state" and "product", then there would be a cell for every unique combination of the two, e.g., one cell each for (California, Tea), (California, Coffee), (Florida, Tea), (Florida, Coffee), etc. Each cell contains one value per measure of the data cube. So if product production and consumption information is needed, then each cell would contain two values, one for the number of products of each type consumed in that state, and one for the number of products of each type produced in that state. Dimensions within a data warehouse are often augmented with a hierarchical structure. If each dimension has a hierarchical structure, then the data warehouse is not a single data cube but rather a lattice of data cubes.

5.10 Exemplary Patient Database

This section provides a more detailed description of a patient database 68 in accordance with one aspect of the invention. As described in Section 5.1, an exemplary patient database 68 includes a plurality of patient records 500 (FIG. 6). There is no limit on the number of patient records 500 that can be held in patient database 68. Database 68 can hold as few as one patient record 500. More typically, database 68 holds between 1 and 100 patient records, more than 100 patient records, more than a thousand patient records, more than ten thousand patient records, more than 100 thousand patient records, between 1 patient record and one million patient records, or more. Each patient record 500 preferably includes a patient identifier 502. As those skilled in database arts will appreciate, a patient identifier 502 need not be explicitly enumerated in certain database systems. For instance, in some systems, a patient identifier 502 can simply be a patient record 500 identifier. However, in some embodiments, a patient identifier 502 can be a number that uniquely identifies a patient within a health care program or clinical trial.

An advantage of database 68 is that it has the capability of tracking molecular marker data profile 504 and trait characterization information 510 for each patient registered in database 68. In some embodiments, a molecular profile 504 is the abundance levels of a plurality of molecular marker products in blood specimens obtained from a patient in accordance with Section 5.2. In some embodiments, such abundance levels are normalized using any of the techniques disclosed in Section 5.7.

In some embodiments, a molecular profile 504 comprises the processed microarray image data from the biological specimen obtained from the patient. In one example, molecular profile data 504 comprises molecular marker abundance information for all or a portion of the cellular constituents represented in a microarray, optional background signal information, and optional associated annotation information describing the probes used for the respective molecular marker. Molecular markers include, but are not limited to RNA (e.g., mRNA) and protein.

In some embodiments, a molecular profile 504 represents the transcriptional state of cellular constituents in a biological specimen. However, in other embodiments, a molecular profile 504 can track aspects of the biological state other than or in addition to transcriptional state. Such other aspects of the biological state include, but are not limited to, the translational state, the activity state of cellular constituents in a biological sample. In some embodiments, for example, molecular profile 504 data is, in fact, protein levels for various proteins in the blood taken from the patient. Thus, in some embodiments, molecular profiles 504 comprise amounts or concentrations of the molecular markers in biological specimens obtained in accordance with Section 5.2.

In one embodiment, the amount of at least one molecular marker that is tracked in a molecular profile 504 comprises abundances of at least one RNA species present in one or more cells in the blood obtained from the patient. Such abundances can be measured by a method comprising contacting a gene transcript array with RNA derived from one or more cells of the biological specimen, or with cDNA derived therefrom. A gene transcript array comprises a surface with attached nucleic acids or nucleic acid mimics. The nucleic acids or nucleic acid mimics are capable of hybridizing with the RNA species or with cDNA derived from the RNA species. In one particular embodiment, the abundance of the RNA is measured by contacting a gene transcript array with the RNA from one or more cells of the biological specimen, or with nucleic acid derived from the RNA, such that the gene transcript array comprises a positionally addressable surface with attached nucleic acids or nucleic acid mimics, where the nucleic acids or nucleic acid mimics are capable of hybridizing with the RNA species, or with nucleic acid derived from the RNA species.

In some embodiments, a molecular profile 504 can include abundance information or activity information about ten or more molecular markers (e.g., genes or proteins), between ten and one thousand molecular markers, between one thousand and twenty thousand molecular markers, or more than twenty thousand molecular markers.

In some embodiments, in addition to or rather than providing abundance information or activity information for molecular markers, a molecular profile 504 tracks polymorphism information. Such polymorphism information includes, but is not limited to, single nucleotide polymorphisms (SNPs), SNP haplotypes, microsatellite markers, restriction fragment length polymorphisms (RFLPs), short tandem repeats, sequence length polymorphisms, DNA methylation, random amplified polymorphic DNA (RAPD), amplified fragment length polymorphisms (AFLP), and "simple sequence repeats." For more information on such polymorphisms, see generally, *The DNA Revolution* by Andrew H. Paterson 1996 (Chapter 2) in: *Genome Mapping in Plants* (ed. Andrew H. Paterson) by Academic Press/R. G. Landis Company, Austin, Tex., 7-21, which is hereby incorporated herein by reference in its entirety SNPs occur approximately once every 600 base pairs in the genome. See, for example, Kruglyak and Nickerson, 2001, Nature Genetics 27, 235. Alleles making up blocks of such SNPs in close physical proximity are often correlated, resulting in reduced genetic variability and defining a limited number of "SNP haplotypes" each of which reflects descent from a single ancient ancestral chromosome. See Fullerton et ah, 2000, Am. J. Hum. Genet. 67, 881. Such haplotype structure is used in some embodiments of the present invention. Patil et al found that a very dense set of SNPs is required to capture all the common haplotype information. See Patil et al, 2001, Science 294, 1719-1723. DNA methylation is described in Grunau et al., 2003, Nucleic Acids Res. 31, pp. 75-77.

RFLPs are the product of allelic differences between DNA restriction fragments caused by nucleotide sequence variability. As is well known to those of skill in the art, RFLPs are typically detected by extraction of genomic DNA and digestion with a restriction endonuclease. Generally, the resulting fragments are separated according to size and hybridized with a probe; single copy probes are preferred. As a result, restriction fragments from homologous chromosomes are revealed. Differences in fragment size among alleles represent an RFLP (see, for example, Helentjaris et ah, 1985, Plant MoL Bio. 5:109-118, and U.S. Pat. No. 5,324,631).

The phrase "random amplified polymorphic DNA" or "RAPD" refers to the amplification product of the distance between DNA sequences homologous to a single oligonucleotide primer appearing on different sites on opposite strands of DNA. Mutations or rearrangements at or between binding sites will result in polymorphisms as detected by the presence or absence of amplification product (see, for example, Welsh and McClelland, 1990, Nucleic Acids Res. 18:7213-7218; Hu and Quiros, 1991, Plant Cell Rep. 10:505-511). AFLP technology refers to a process that is designed to generate large numbers of randomly distributed molecular markers (see, for example, European Patent Application No. 0534858 A1).

"Simple sequence repeats" or "SSRs" are di-, tri- or tetra-nucleotide tandem repeats within a genome. The repeat region can vary in length between genotypes while the DNA flanking the repeat is conserved such that the same primers will work in a plurality of genotypes. A polymorphism between two genotypes represents repeats of different lengths between the two flanking conserved DNA sequences (see, for example, Akagi et al, 1996, Theor. Appl. Genet. 93, 1071-1077; Bligh et al, 1995, Euphytica 86:83-85; Struss et al, 1998, Theor. Appl. Genet. 97, 308-315; Wu et al, 1993, MoL Gen. Genet. 241, 225-235; and U.S. Pat. No. 5,075,217). SSR are also known as satellites or microsatellites.

In addition to molecular profiles 50, patient records 500 include trait characterizations 510. In some embodiments, a trait characterization 510 comprises observations made by a patient's physician. In some instances, the observations made by a physician include a code from the International Classification of Diseases, $9^{th}$ Revision, prepared by the Department of Health and Human Services (ICD-9 codes), or an equivalent, and dates such observations were made.

5.11 Exemplary Genes as Candidate Molecular Markers

Non-limiting examples of genes useful as molecular markers for use in the invention can include, but are not limited to, genes specific for or involved in a particular biological process, such as apoptosis, differentiation, stress response, aging, proliferation, etc.; cellular mechanism genes, e.g., cell-cycle, signal transduction, metabolism of toxic compounds, and the like; disease associated genes, e.g., genes involved in cancer, schizophrenia, diabetes, high blood pressure, atherosclerosis, viral-host interaction and infection and the like. Exemplary genes can also include immune responsive genes. Further examples of genes can include, but are not limited to, oncogenes whose expression within a cell induces that cell to become converted from a normal cell into a tumor cell. See for example Hanahan & Weinberg, 2000, Cell 100: 57; Yokota., 2000, Carcinogenesis 21:497. Further examples of genes can include, but are not limited to cytokine genes. See, for example, Rubinstein et al, 1998, Cytokine Growth Factor Rev. 9:175-81. Other examples of genes can include idiotype protein genes (e.g., Benezra., et al, 2001 Oncogene 20:8334-41; Norton, 2000, J. Cell Sci. 113:3897), prion genes (e.g., Prusiner et al, 1998, Cell 93:337-48; Safar & Prusiner, 1998, Prog. Brain Res. 117:421); genes that express molecules that induce angiogenesis (e.g., Gould & Wagner, 2002, Hum. Pathol. 33:1061); genes encoding adhesion molecules (e.g., Chothia, & Jones, 1997, Annu. Rev. Biochem. 66:823; Parise et al, 2000, Semin. Cancer Biol. 10:407-14); genes encoding cell surface receptors (e.g., Deller and Jones, 2000, Curr. Opin. Struct. Biol. 10:213); genes of proteins that are involved in metastasizing and/or invasive processes (e.g., Boyd, 1996, Cancer Metastasis Rev. 15:77; Yokota, 2000, Carcinogenesis 21:497); genes of proteases as well as of molecules that regulate apoptosis and the cell cycle (e.g., Matrisian, 1999, Curr. Biol. 9:R776; Krepela, 2001, Neoplasma 48:332; Basbaum and Werb, 1996, Curr. Opin. Cell Biol. 8:731; Birkedal-Hansen et al, 1993, Crit. Rev. Oral Biol. Med. 4:197-250; Mignatti and Rifkin, 1993, Physiol. Rev. 73:161; Stetler-Stevenson et al., 1993, Annu. Rev. Cell Biol. 9:541; Brinkerhoff and Matrisan, 2002, Nature Reviews 3:207; Strasser. et al, 2000, Annu. Rev. Biochem. 69:217; Chao and Korsmeyer, 1998, Annu. Rev. Immunol. 16:395; Mullauer et al, 2001, Mutat. Res. 488:211; Fotedar et al, 1996, Prog. Cell Cycle Res. 2:147; Reed., 2000, Am. J. Pathol. 157:1415; D'Ari, 2001, Bioassays 23:563); or multidrug resistance genes, such as the MDRI gene. In one embodiment, a gene is an immune response gene or a non-immune response gene such as cytokines (e.g., interleukins and interferons such as TNF-alpha, IL-10, IL-12, IL-2, IL-4, IL-10, IL-12, IL-13, TGF-Beta, IFN-gamma; immunoglobulins, complement and the like). See, for example, Bellardelli, 1995, *Role of interferons and other cytokines in the regulation of the immune response APMIS* 103: 161.

5.12 Clustering Techniques

In some embodiments, clustering is used. For instance, clustering can be used in step 204 to visualize the relationship between the data measured for a plurality of molecular markers in step 202. In some embodiments, any of the clustering techniques described in Draghici, *Data Analysis Tools For DNA Microarrays,* 2003, Chapman & Hall, CRC Press, New York, pp. 263-297, which is hereby incorporated by reference in its entirety, are used in the present invention. Clustering is also described on pages 211-256 of Duda and Hart, *Pattern Classification and Scene Analysis,* 1973, John Wiley & Sons, Inc., New York, which is hereby incorporated by reference. As described in Section 6.7 of Duda, the clustering problem is described as one of finding natural groupings in a dataset. To identify natural groupings, two issues are addressed. First, a way to measure similarity (or dissimilarity) between two samples is determined. This metric (similarity measure) is used to ensure that the samples in one cluster are more like one another than they are to samples in other clusters. Second, a mechanism for partitioning the data into clusters using the similarity measure is determined.

Similarity measures are discussed in Section 6.7 of Duda, where it is stated that one way to begin a clustering investigation is to define a distance function and to compute the matrix of distances between all pairs of samples in a dataset. If distance is a good measure of similarity, then the distance between samples in the same cluster will be significantly less than the distance between samples in different clusters. However, as stated on page 215 of Duda, clustering does not require the use of a distance metric. For example, a nonmetric similarity function s(x, x') can be used to compare two vectors x and x'. Conventionally, s(x, x') is a symmetric function whose value is large when x and x' are somehow "similar". An example of a nonmetric similarity function s(x, x') is provided on page 216 of Duda.

Once a method for measuring "similarity" or "disimilarity" between points in a dataset has been selected, clustering requires a criterion function that measures the clustering quality of any partition of the data. Partitions of the data set that extremize the criterion function are used to cluster the data. See page 217 of Duda. Criterion functions are discussed in Section 6.8 of Duda.

More recently, Duda et al., Pattern Classification, $2^{nd}$ edition, John Wiley & Sons, Inc. New York, has been published. Pages 537-563 describe clustering in detail. More information on clustering techniques can be found in Kaufman and Rousseeuw, 1990, *Finding Groups in Data: An Introduction to Cluster Analysis,* Wiley, New York, N.Y.; Everitt, 1993, *Cluster analysis* (3d ed.), Wiley, New York, N.Y.; and Backer, 1995, *Computer-Assisted Reasoning in Cluster Analysis,* Prentice Hall, Upper Saddle River, N.J. Now that an overview of clustering techniques has been given, more specific examples of clustering that can be performed in the methods described in Section 5.1 is presented.

5.12.1 Hierarchical Clustering Techniques

Hierarchical cluster analysis is a statistical method for finding relatively homogenous clusters of elements based on measured data. Consider a sequence of partitions of n samples into c clusters. The first of these is a partition into n clusters, each cluster containing exactly one sample. The next is a partition into n 1 clusters, the next is partition into n−2, and so on until the $n^{th}$, in which all the samples form one cluster. Level k in the sequence of partitions occurs when c=n−k+1. Thus, level one corresponds to n clusters and level n corresponds to one cluster. Given any two samples x and x*, at some level they will be grouped together in the same cluster. If the sequence has the property that whenever two samples are in the same cluster at level k they remain together at all higher levels, then the sequence is said to be a hierarchical clustering. Duda et al., 2001, Pattern Classification, $2^{nd}$ edition, John Wiley & Sons, New York, 2001: 551. Examples of hierarchical clustering includes agglomerative clustering using nearest-neighbor algorithm, farthest-neighbor algorithm, the average linkage algorithm, the centroid algorithm, or the sum-of-squares algorithm. See, for example WO03 100557.

5.12.1.1 Clustering with Pearson Correlation Coefficients

In some embodiments of the present invention, molecular marker data is clustered using agglomerative hierarchical clustering with Pearson correlation coefficients. In this form of clustering, similarity is determined using Pearson correlation coefficients between sets of molecular marker data measurements. Other metrics that can be used, in addition to the Pearson correlation coefficient, include but are not limited to, a Euclidean distance, a squared Euclidean distance, a Euclidean sum of squares, a Manhattan metric, and a squared Pearson correlation coefficient. Such metrics can be computed using SAS (Statistics Analysis Systems Institute, Gary, N.C.) or S-Plus (Statistical Sciences, Inc., Seattle, Wash.).

5.12.1.2 Divisive Clustering

In some embodiments, the hierarchical clustering technique used to cluster molecular marker data measurements is a divisive clustering procedure. Divisive (top-down clustering) procedures start with all of the samples in one cluster and form the sequence by successfully splitting clusters. Divisive clustering techniques are classified as either a polymeric or a monothetic method. A polythetic approach divides clusters into arbitrary subsets.

5.12.2 K-Means Clustering

In k-means clustering, sets of molecular marker data measurements are randomly assigned to K user specified clusters. The centroid of each cluster is computed by averaging the value of the vectors in each cluster. Then, for each i=1, . . . , N, the distance between vector $x_i$ and each of the cluster centroids is computed. Each vector x; is then reassigned to the cluster with the closest centroid. Next, the centroid of each affected cluster is recalculated. The process iterates until no more reassignments are made. See, for example, Duda et ah, 2001, *Pattern Classification,* John Wiley & Sons, New York, N.Y., pp. 526-528. A related approach is the fuzzy k-means clustering algorithm, which is also known as the fuzzy c-means algorithm. In the fuzzy k-means clustering algorithm, the assumption that every set of molecular marker data measurements is in exactly one cluster at any given time is relaxed so that every set has some graded or "fuzzy" membership in a cluster. See Duda et ah, 2001, *Pattern Classification,* John Wiley & Sons, New York, N.Y., pp. 528-530.

5.12.3 Jarvis-Patrick Clustering

Jarvis-Patrick clustering is a nearest-neighbor non-hierarchical clustering method in which a set of objects is partitioned into clusters on the basis of the number of shared nearest-neighbors. In the standard implementation advocated by Jarvis and Patrick, 1973, *IEEE Trans. Comput*, C-22: 1025-1034, a preprocessing stage identifies the K nearest-neighbors of each object in the dataset. In the subsequent clustering stage, two objects i and j join the same cluster if (i) i is one of the K nearest-neighbors of j, (ii) j is one of the K nearest-neighbors of i, and (iii) i and j have at least $k_m j_n$ of their K nearest-neighbors in common, where K and $k_m i_n$ are user-defined parameters. The method has been widely applied to clustering chemical structures on the basis of fragment descriptors and has the advantage of being much less computationally demanding than hierarchical methods, and thus more suitable for large databases. Jarvis-Patrick clustering can be performed using the Jarvis-Patrick Clustering Package 3.0 (Barnard Chemical Information, Ltd., Sheffield, United Kingdom).

5.13 Molecular Markers

Molecular marker is used herein to mean a gene or genetic element. All genes and genetic elements are considered molecular markers, but the invention teaches how to identify molecular markers useful for diagnosing a trait of interest.

5.14 Representative Mathematical Models that can be Used to Build Classifiers This section describes various mathematical models that can be used to build classifier in accordance with the methods of the present invention.

5.14.1 Regression Classifiers

In some embodiments, the classifier constructed in step 216 is a regression classifier, preferably a logistic regression classifier. Such a regression classifier includes a coefficient for each of the molecular markers selected in the last instance of step 214. In such embodiments, the coefficients for the regression classifier are computed using, for example, a maximum likelihood approach. In such a computation, the data measured for the molecular markers in step 206 (e.g., RT-PCR data) is used. In particular embodiments, molecular marker data from only two trait subgroups is used and the dependent variable is absence or presence of a particular trait in the subjects for which molecular marker data is available. As in the case of step 210, the two different trait subgroups can, for example, respectively represent a diseased and non-diseased state, a first diseased state (e.g. liver cancer) and a second phenotypically similar (e.g. hepatitis B) or unrelated diseased state (e.g., Alzheimer's disease), those subjects that are responsive to drug therapy and those subjects that are not responsive to drug therapy, or subjects that have been subjected to a perturbation (e.g., drug treatment) versus those subjects that have not been subjected to a perturbation.

In another specific embodiment, training population 44 consists of a plurality of trait subgroups (e.g., three or more trait subgroups, four or more specific trait subgroups, etc.). In this specific embodiment, a generalization of the logistic regression model that handles multicategory responses can be used in step 216 to develop a classifier that discriminates between the various trait subgroups found in the training population. For example, measured data for selected molecular markers can be applied to any of the multicategory logit models described in Agresti, *An Introduction to Categorical Data Analysis*, 1996, John Wiley & Sons, Inc., New York, Chapter 8, which is hereby incorporated herein by reference in its entirety, in order to develop a classifier capable of discriminating between any of a plurality of trait subgroups represented in a training population.

5.14.2 Neural Networks

The present invention is not limited to the use of logistic regression. In some embodiments, the data measured for the molecular markers in step 206 (e.g., RT-PCR data) can be used to train a neural network.

In some embodiments, a neural network is derived in each successive instance of step 216 of FIG. 2A using the combination of molecular markers selected in the corresponding instance of step 214 of FIG. 2A. A neural network is a two-stage regression or classification classifier. A neural network has a layered structure that includes a layer of input units (and the bias) connected by a layer of weights to a layer of output units. For regression, the layer of output units typically includes just one output unit. However, neural networks can handle multiple quantitative responses in a seamless fashion.

In multilayer neural networks, there are input units (input layer), hidden units (hidden layer), and output units (output layer). There is, furthermore, a single bias unit that is connected to each unit other than the input units. Neural networks are described in Duda et ah, 2001, *Pattern Classification*, Second Edition, John Wiley & Sons, Inc., New York; and Hastie et ah, 2001, *The Elements of Statistical Learning*, Springer-Verlag, New York.

The basic approach to the use of neural networks is to start with an untrained network, present a training pattern to the input layer, and to pass signals through the net and determine the output at the output layer. These outputs are then compared to the target values; any difference corresponds to an error. This error or criterion function is some scalar function of the weights and is minimized when the network outputs match the desired outputs. Thus, the weights are adjusted to reduce this measure of error. For regression, this error can be sum-of-squared errors. For classification, this error can be either squared error or cross-entropy (deviation). See, e.g., Hastie et al, 2001, *The Elements of Statistical Learning*, Springer-Verlag, New York.

Three commonly used training protocols are stochastic, batch, and on-line. In stochastic training, patterns are chosen randomly from the training set and the network weights are updated for each pattern presentation. Multilayer nonlinear networks trained by gradient descent methods such as stochastic back-propagation perform a maximum-likelihood estimation of the weight values in the classifier defined by the network topology. In batch training, all patterns are presented to the network before learning takes place. Typically, in batch training, several passes are made through the training data. In online training, each pattern is presented once and only once to the net.

In some embodiments, consideration is given to starting values for weights. If the weights are near zero, then the operative part of the sigmoid commonly used in the hidden layer of a neural network (see, e.g., Hastie et ah, 2001, *The Elements of Statistical Learning*, Springer-Verlag, New York) is roughly linear, and hence the neural network collapses into an approximately linear classifier. In some embodiments, starting values for weights are chosen to be random values near zero. Hence the classifier starts out nearly linear, and becomes nonlinear as the weights increase. Individual units localize to directions and introduce nonlinearities where needed. Use of exact zero weights leads to zero derivatives and perfect symmetry, and the algorithm never moves. Alternatively, starting with large weights often leads to poor solutions.

Since the scaling of inputs determines the effective scaling of weights in the bottom layer, it can have a large effect on the quality of the final solution. Thus, in some embodiments, at the outset all expression values are standardized to have mean zero and a standard deviation of one. This ensures all inputs are treated equally in the regularization process, and allows one to choose a meaningful range for the random starting weights. With standardization inputs, it is typical to take random uniform weights over the range [−0.7, +0.7].

A recurrent problem in the use of three-layer networks is the optimal number of hidden units to use in the network. The number of inputs and outputs of a three-layer network are determined by the problem to be solved. In embodiments of the present invention, the number of inputs for a given neural network can, in some embodiments, equal the number of molecular markers selected in the corresponding instance of step 214. In other embodiments, for each input, two or more molecular markers will be selected (for example wherein ratios of genes (A/B) are utilized. The number of outputs for the neural network will typically be just one (ie wherein the output neuron is one dimensional e.g. health vs. disease). If there are additional input dimensions, new additional output neurons may be created. In some embodiments more than one output is used so that more than just two states can be defined by the network. If too many hidden units are used in a neural network, the network will have too many degrees of freedom and is trained too long, there is a danger that the network will overfit the data. If there are too few hidden units, the training set cannot be learned. Generally speaking, however, it is better to have too many hidden units than too few. With too few hidden units, the classifier might not have enough flexibility to capture the nonlinearities in the data; with too many hidden units, the extra weight can be shrunk towards zero if appropriate regularization or pruning, as described below, is used. In typical embodiments, the number of hidden units in somewhere in the range of 5 to 100, with the number increasing with the number of inputs and number of training cases.

One general approach to determining the number of hidden units to use is to apply a regularization approach. La the regularization approach, a new criterion function is constructed that depends not only on the classical training error, but also on classifier complexity. Specifically, the new criterion function penalizes highly complex classifiers; searching for the minimum in this criterion is to balance error on the training set with error on the training set plus a regularization term, which expresses constraints or desirable properties of solutions:

$$\tilde{J} = \tilde{J}_{pat} + \lambda J_{reg}.$$

The parameter λ is adjusted to impose the regularization more or less strongly. In other words, larger values for λ will tend to shrink weights towards zero: typically cross-validation with a validation set is used to estimate λ. This validation set can be obtained by setting aside a random subset of the population measured in step 202 of FIG. 2A. Other forms of penalty have been proposed, for example the weight elimination penalty (see, e.g., Hastie et al, 2001, *The Elements of Statistical Learning*, Springer-Verlag, New York).

Another approach to determine the number of hidden units to use is to eliminate—prune—weights that are least needed. In one approach, the weights with the smallest magnitude are eliminated (set to zero). Such magnitude-based pruning can work, but is nonoptimal; sometimes weights with small magnitudes are important for learning and training data. In some embodiments, rather than using a magnitude-based pruning approach, Wald statistics are computed. The fundamental idea in Wald Statistics is that they can be used to estimate the importance of a hidden unit (weight) in a classifier. Then, hidden units having the least importance are eliminated (by setting their input and output weights to zero). Two algorithms in this regard are the Optimal Brain Damage (OBD) and the Optimal Brain Surgeon (OBS) algorithms that use second-order approximation to predict how the training error depends upon a weight, and eliminate the weight that leads to the smallest increase in training error.

Optimal Brain Damage and Optimal Brain Surgeon share the same basic approach of training a network to local minimum error at weight w, and then pruning a weight that leads to the smallest increase in the training error. The predicted functional increase in the error for a change in full weight vector δw is:

$$\delta J = \left(\frac{\partial J}{\partial w}\right)^t \cdot \delta w + \frac{1}{2} \delta w^t \cdot \frac{\partial^2 J}{\partial w^2} \cdot \delta w + O(\|\delta w\|^3)$$

where $$\frac{\partial^2 J}{dw^2}$$

is the Hessian matrix. The first term vanishes because we are at a local minimum in error; third and higher order terms are ignored. The general solution for minimizing this function given the constraint of deleting one weight is:

$$\delta w = -\frac{w_q}{[H^{-1}]_{qq}} H^{-1} \cdot u_q \text{ and } L_q = \frac{1}{2} - \frac{w_q^2}{[H^{-1}]_{qq}}$$

Here, $u_q$ is the unit vector along the qth direction in weight space and $L_q$ is approximation to the saliency of the weight q—the increase in training error if weight q is pruned and the other weights updated δw. These equations require the inverse of H. One method to calculate this inverse matrix is to start with a small value, $H_0^{-1} = \alpha^{-1} I$, where α is a small parameter—effectively a weight constant. Next the matrix is updated with each pattern according to $$H_{m+1}^{-1} = H_m^{-1} - \frac{H_m^{-1} X_{m+1} X_{m+1}^T H_m^{-1}}{\frac{n}{a_m} + X_{m+1}^T H_m^{-1} X_{m+1}} \qquad \text{Eqn. 1}$$

where the subscripts correspond to the pattern being presented and $a_m$ decreases with m. After the full training set has been presented, the inverse Hessian matrix is given by $H^{n_1} = H_n^{-1}$. In algorithmic form, the Optimal Brain Surgeon method is:

ᴸ begin initialize $\Pi_H$, W, θ
train a reasonably large network to minimum error
do compute $H^{-1}$ by Eqn. 1

$$q \blacklozenge \leftarrow \arg\min_q w_q^2/(2[H^{-1}]_{qq}) \text{ (saliency } L_q)$$
$$w \leftarrow \sim w - \frac{w_{q^*}}{[H^{-1}]_{q^*q^*}} H^{-1} e_{q^*} \text{ (saliency } L_q)$$

until J(w)>θ
return w
end

The Optimal Brain Damage method is computationally simpler because the calculation of the inverse Hessian matrix in line 3 is particularly simple for a diagonal matrix. The above algorithm terminates when the error is greater than a criterion initialized to be θ. Another approach is to change line 6 to terminate when the change in J(w) due to elimination of a weight is greater than some criterion value.

In some embodiments, the back-propagation neural network (see, for example Abdi, 1994, "A neural network primer", J. Biol System. 2, 247-283) containing a single bidden layer often neurons (ten hidden units) found in EasyNN-Plus version 4.0g software package (Neural Planner Software Inc.) is used. In one specific example, parameter values within the EasyNN-Plus program were set as follows: learning parameter=0.6, and momentum parameter=0.8. In some embodiments in which the EasyNN-Plus version 4.0g software package is used, "outlier" samples are identified by performing twenty independently-seeded trials involving 20,000 learning cycles each.

5.14.3 Clustering

In some embodiments, the expression values for select genes are used to cluster a training set. For example, consider the case in which ten genes are used. Each member m of the training population will have expression values for each of the ten genes. Such values from a member m in the training population define the vector:

| $X_{1m}$ | $X_{2m}$ | $X_{3m}$ | $X_{4m}$ | $X_{5m}$ | $X_{6m}$ | $X_{7m}$ | $X_{8m}$ | $X_{9m}$ | $X_{10m}$ |
|---|---|---|---|---|---|---|---|---|---| where $Xj_m$ is the expression level of the $i^{th}$ gene in organism m. If there are m organisms in the training set, selection of i genes will define m vectors. Note that the methods of the present invention do not require that each expression value of every single gene used in the vectors be represented in every single vector m. In other words, data from a subject in which one of the $i^{th}$ genes is not found can still be used for clustering. In such instances, the missing expression value is assigned either a "zero" or some other normalized value. In some embodiments, prior to clustering, the gene expression values are normalized to have a mean value of zero and unit variance.

Those members of the training population that exhibit similar expression patterns across the training group will tend to cluster together. A particular combination of genes of the present invention is considered to be a good classifier in this aspect of the invention when the vectors cluster into the trait groups found in the training population. For instance, if the training population includes patients with no osteoarthritis, mild osteoarthritis, moderate osteoarthritis, marked osteoarthritis, and severe osteoarthritis an ideal clustering classifier will cluster the population into five groups, with each group uniquely representing either absence or one of the four stages of osteoarthritis. In some embodiments, the clustering classifier simply clusters the population into a first subgroup (a first cluster) that does not have osteoarthritis and a second subgroup (a second cluster) that has osteoarthritis. In some embodiments, the classifier clusters the data into a first subgroup that has a particular stage of osteoarthritis (e.g., mild) and two or more subgroups that do not include subjects having the particular stage of osteoarthritis represented in the first subgroup.

Clustering is described on pages 211-256 of Duda and Hart, *Pattern Classification and Scene Analysis*, 1973, John Wiley & Sons, Inc., New York. As described in Section 6.7 of Duda, the clustering problem is described as one of finding natural groupings in a dataset. To identify natural groupings, two issues are addressed. First, a way to measure similarity (or dissimilarity) between two samples is determined. This metric (similarity measure) is used to ensure that the samples in one cluster are more like one another than they are to samples in other clusters. Second, a mechanism for partitioning the data into clusters using the similarity measure is determined.

Similarity measures are discussed in Section 6.7 of Duda, where it is stated that one way to begin a clustering investigation is to define a distance function and to compute the matrix of distances between all pairs of samples in a dataset. If distance is a good measure of similarity, then the distance between samples in the same cluster will be significantly less than the distance between samples in different clusters. However, as stated on page 215 of Duda, clustering does not require the use of a distance metric. For example, a nonmetric similarity function s(x, x') can be used to compare two vectors x and x'. Conventionally, s(x, x') is a symmetric function whose value is large when x and x' are somehow "similar". An example of a nonmetric similarity function s(x, x') is provided on page 216 of Duda.

Once a method for measuring "similarity" or "dissimilarity" between points in a dataset has been selected, clustering requires a criterion function that measures the clustering quality of any partition of the data. Partitions of the data set that extremize the criterion function are used to cluster the data. See page 217 of Duda. Criterion functions are discussed in Section 6.8 of Duda.

More recently, Duda et ah, Pattern Classification, $2^{nd}$ edition, John Wiley & Sons, Inc. New York, has been published. Pages 537-563 describe clustering in detail. More information on clustering techniques can be found in Kaufman and Rousseeuw, 1990, *Finding Groups in Data: An Introduction to Cluster Analysis*, Wiley, New York, N.Y.; Everitt, 1993, Cluster analysis (3d ed.), Wiley, New York, N.Y.; and Backer, 1995, *Computer-Assisted Reasoning in Cluster Analysis*, Prentice Hall, Upper Saddle River, N.J. Particular exemplary clustering techniques that can be used in the present invention include, but are not limited to, hierarchical clustering (agglomerative clustering using nearest-neighbor algorithm, farthest-neighbor algorithm, the average linkage algorithm, the centroid algorithm, or the sum-of-squares algorithm), k-means clustering, fuzzy k-means clustering algorithm, and Jarvis-Patrick clustering.

5.14.4 Principal Component Analysis

Principal component analysis (PCA) has been proposed to analyze gene expression data. Principal component analysis is a classical technique to reduce the dimensionality of a data set by transforming the data to a new set of variable (principal components) that summarize the features of the data. See, for example, Jolliffe, 1986, *Principal Component Analysis*, Springer, N.Y. Principal components (PCs) are uncorrelate and are ordered such that the $k^{th}$ PC has the Mi largest variance among PCs. The $k^{th}$ PC can be interpreted as the direction that maximizes the variation of the projections of the data points such that it is orthogonal to the first k−1 PCs. The first few PCs capture most of the variation in the data set. In contrast, the last few PCs are often assumed to capture only the residual 'noise' in the data.

PCA can also be used to create a classifier in accordance with the present invention. In such an approach, vectors for the select genes described in the present invention can be constructed in the same manner described for clustering above. In fact, the set of vectors, where each vector represents the expression values for the select genes from a particular member of the training population, can be considered a matrix. In some embodiments, this matrix is represented in a Free-Wilson method of qualitative binary description of monomers (Kubinyi, 1990, 3*D QSAR in drug design theory methods and applications*, Pergamon Press, Oxford, pp 589-638), and distributed in a maximally compressed space using PCA so that the first principal component (PC) captures the largest amount of variance information possible, the second principal component (PC) captures the second largest amount of all variance information, and so forth until all variance information in the matrix has been accounted for.

Then, each of the vectors (where each vector represents a member of the training population) is plotted. Many different types of plots are possible. In some embodiments, a one-dimensional plot is made. In this one-dimensional plot, the value for the first principal component from each of the members of the training population is plotted. In this form of plot, the expectation is that members of a first subgroup (e.g. those subjects that do not have osteoarthritis) will cluster in one range of first principal component values and members of a second subgroup (e.g., those subjects that have osteoarthritis) will cluster in a second range of first principal component values.

In one ideal example, the training population comprises two subgroups: "control" and "patients with osteoarthritis." The first principal component is computed using the molecular marker expression values for the select genes of the present invention across the entire training population data set. Then, each member of the training set is plotted as a function of the value for the first principal component. In this ideal example, those members of the training population in which the first principal component is positive are the "responders" and those members of the training population in which the first principal component is negative are "patients with osteoarthritis."

In some embodiments, the members of the training population are plotted against more than one principal component. For example, in some embodiments, the members of the training population are plotted on a two-dimensional plot in which the first dimension is the first principal component and the second dimension is the second principal component. In such a two-dimensional plot, the expectation is that members of each subgroup represented in the training population will cluster into discrete groups. For example, a first cluster of members in the two-dimensional plot will represent subjects with mild osteoarthritis, a second cluster of members in the two-dimensional plot will represent subjects with moderate osteoarthritis, and so forth.

In some embodiments, the members of the training population are plotted against more than two principal components and a determination is made as to whether the members of the training population are clustering into groups that each uniquely represents a subgroup found in the training population. In some embodiments, principal component analysis is performed by using the R mva package (Anderson, 1973, *Cluster Analysis for applications*, Academic Press, New York 1973; Gordon, Classification, Second Edition, Chapman and Hall, CRC, 1999). Principal component analysis is further described in Duda, *Pattern Classification*, Second Edition, 2001, John Wiley & Sons, Inc.

5.14.5 Nearest Neighbor Classifier Analysis

Nearest neighbor classifiers are memory-based and require no classifier to be fit. Given a query point $x_Q$, the k training points $x_{(r)}$, r, ..., k closest in distance to $x_0$ are identified and then the point $X_0$ is classified using the k nearest neighbors. Ties can be broken at random. In some embodiments, Euclidean distance in feature space is used to determine distance as:

$$d_o = \|\ddot{A}_{(0} - \ddot{A}_o\|$$

Typically, when the nearest neighbor algorithm is used, the expression data used to compute the linear discriminant is standardized to have mean zero and variance 1. In the present invention, the members of the training population are randomly divided into a training set and a test set. For example, in one embodiment, two thirds of the members of the training population are placed in the training set and one third of the members of the training population are placed in the test set. A select combination of genes described in the present invention represents the feature space into which members of the test set are plotted. Next, the ability of the training set to correctly characterize the members of the test set is computed. In some embodiments, nearest neighbor computation is performed several times for a given combination of genes of the present invention. In each iteration of the computation, the members of the training population are randomly assigned to the training set and the test set. Then, the quality of the combination of genes is taken as the average of each such iteration of the nearest neighbor computation.

The nearest neighbor rule can be refined to deal with issues of unequal class priors, differential misclassification costs, and feature selection. Many of these refinements involve some form of weighted voting for the neighbors. For more information on nearest neighbor analysis, see Duda, *Pattern Classification*, Second Edition, 2001, John Wiley & Sons, Inc; and Hastie, 2001, *The Elements of Statistical Learning*, Springer, N.Y.

5.14.6 Linear Discriminant Analysis

Linear discriminant analysis (LDA) attempts to classify a subject into one of two categories based on certain object properties. In other words, LDA tests whether object attributes measured in an experiment predict categorization of the objects. LDA typically requires continuous independent variables and a dichotomous categorical dependent variable. In the present invention, the expression values for the select combinations of genes described in the present invention across a subset of the training population serve as the requisite continuous independent variables. The trait subgroup classification of each of the members of the training population serves as the dichotomous categorical dependent variable.

LDA seeks the linear combination of variables that maximizes the ratio of between-group variance and within-group variance by using the grouping information. Implicitly, the linear weights used by LDA depend on how the expression of a molecular marker across the training set separates in the two groups (e.g., a group that has osteoarthritis and a group that does not have osteoarthritis) and how this gene expression correlates with the expression of other genes. In some embodiments, LDA is applied to the data matrix of the N members in the training sample by K genes in a combination of genes described in the present invention. Then, the linear discriminant of each member of the training population is plotted. Ideally, those members of the training population representing a first subgroup (e.g. those subjects that do not have osteoarthritis) will cluster into one range of linear discriminant values (e.g., negative) and those member of the training population representing a second subgroup (e.g. those subjects that have osteoarthritis) will cluster into a second range of linear discriminant values (e.g., positive). The LDA is considered more successful when the separation between the clusters of discriminant values is larger. For more information on linear discriminant analysis, see Duda, *Pattern Classification*, Second Edition, 2001, John Wiley & Sons, Inc; and Hastie, 2001, *The Elements of Statistical Learning*, Springer, N.Y.; Venables & Ripley, 1997, *Modern Applied Statistics with s-plus*, Springer, N.Y.

5.14.7 Quadratic Discriminant Analysis

Quadratic discriminant analysis (QDA) takes the same input parameters and returns the same results as LDA. QDA uses quadratic equations, rather than linear equations, to produce results. LDA and QDA are interchangeable, and which to use is a matter of preference and/or availability of software to support the analysis. Logistic regression takes the same input parameters and returns the same results as LDA and QDA.

5.14.8 Support Vector Machines

In some embodiments of the present invention, support vector machines (SVMs) are used to classify subjects using genesor genetic information. SVMs are a relatively new type of learning algorithm. See, for example, Cristianini and Shawe-Taylor, 2000, *An Introduction to Support Vector Machines*, Cambridge University Press, Cambridge, Boser et al, 1992, "A training algorithm for optimal margin classifiers, in *Proceedings of the 5th Annual ACM Workshop on Computational Learning Theory*, ACM Press, Pittsburgh, Pa., pp. 142-152; Vapnik, 1998, *Statistical Learning Theory*, Wiley, New York. When used for classification, SVMs separate a given set of binary labeled training data with a hyper-plane that is [a maximal distance from each point using a fitting algorithm. For cases in which no linear separation is possible, SVMs can work in combination with the technique of 'kernels', which automatically realizes a non-linear mapping to a feature space. The hyper-plane found by the SVM in feature space corresponds to a non-linear decision boundary in the input space.

In one approach, when a SVM is used, the gene expression data is standardized to have mean zero and unit variance and the members of a training population are randomly divided into a training set and a test set. For example, in one embodiment, two thirds of the members of the training population are placed in the training set and one third of the members of the training population are placed in the test set. The expression values for a combination of genes is used to train the SVM. Then the ability for the trained SVM to correctly classify members in the test set is determined. In some embodiments, this computation is performed several times for a given combination of molecular markers. In each iteration of the computation, the members of the training population are randomly assigned to the training set and the test set. Then, the quality of the combination of molecular markers is taken as the average of each such iteration of the SVM computation. For more information on SVMs, see Duda, *Pattern Classification*, Second Edition, 2001, John Wiley & Sons, Inc.; Hastie, 2001, *The Elements of Statistical Learning*, Springer, N.Y.; and Furey et al, 2000, Bioinformatics 16, 906-914.

5.14.9 Decision Trees

In some embodiments of the present invention, decision trees are used to classify subjects using expression data for combinations of genes. Decision tree algorithms belong to the class of supervised learning algorithms. The aim of a decision tree is to induce a classifier (a tree) from real-world example data. This tree can be used to classify unseen examples which have not been used to derive the decision tree.

A decision tree is derived from training data. An example contains values for the different attributes and what class the example belongs. In the present invention, the training data is expression data for a combination of genes across the training population.

The following algorithm describes a decision tree derivation:

Tree (Examples, Class, Attributes)
  Create a root node
  If all Examples have the same Class value, give the root this label
  Else if Attributes is empty label the root according to the most common value
  Else begin
    Calculate the information gain for each attribute
    Select the attribute A with highest information gain and make this the root attribute
    For each possible value, v, of this attribute
      Add a new branch below the root, corresponding to A=v
      Let Examples(v) be those examples with A=V
      If Examples(v) is empty, make the new branch a leaf node labeled with the most common value among Examples
      Else let the new branch be the tree created by
      Tree (Examples(v),Class,Attributes—{A})
  end A more detailed description of the calculation of information gain is shown in the following. If the possible classes $v_i$ of the examples have probabilities P(vj) then the information content I of the actual answer is given by:

$$I(P(v_1), \ldots , P(v_n)) = \sum_{i=1}^{n} -P(v_i)\log_2 P(v_i)$$

The I-value shows how much information we need in order to be able to describe the outcome of a classification for the specific dataset used. Supposing that the dataset contains p positive (e.g. has osteoarthritis) and n negative (e.g. healthy) examples (e.g. individuals), the information contained in a correct answer is:

$$rt\left(\frac{p}{p+n}, \frac{n}{p+n}\right) = -\frac{p}{p+n}\log_2\frac{p}{p+n} - \frac{UL}{p+n} \cdot \log_2\frac{-L}{p+n}$$

where $\log_2$ is the logarithm using base two. By testing single attributes the amount of information needed to make a correct classification can be reduced. The remainder for a specific attribute A (e.g. a gene) shows how much the information that is needed can be reduced.

$$\text{Remainder}(A) = \sum_{i=1}^{v} \frac{p_i+n_i}{p+n} I\left(\frac{p_i}{p_i+n}, \frac{n_i}{p_i+n_i}\right)$$

"v" is the number of unique attribute values for attribute A in a certain dataset, "i" is a certain attribute value, "pi" is the number of examples for attribute A where the classification is positive (e.g. cancer), "$n_i$" is the number of examples for attribute A where the classification is negative (e.g. healthy).

The information gain of a specific attribute A is calculated as the difference between the information content for the classes and the remainder of attribute A:

$$Gain(A) = I\left(\frac{p}{p+n}, \frac{n}{p+n}\right) - Remaind\beta r(A)$$

The information gain is used to evaluate how important the different attributes are for the classification (how well they split up the examples), and the attribute with the highest information.

In general there are a number of different decision tree algorithms, many of which are described in Duda, *Pattern Classification*, Second Edition, 2001, John Wiley & Sons, Inc. Decision tree algorithms often require consideration of feature processing, impurity measure, stopping criterion, and pruning. Specific decision tree algorithms include, cut are not limited to classification and regression trees (CART), multivariate decision trees, ID3, and C4.5.

In one approach, when a decision tree is used, the gene expression data for a select combination of genes described in the present invention across a training population is standardized to have mean zero and unit variance. The members of the training population are randomly divided into a training set and a test set. For example, in one embodiment, two thirds of the members of the training population are placed in the training set and one third of the members of the training population are placed in the test set. The expression values for a select combination of genes described in the present invention is used to construct the decision tree. Then, the ability for the decision tree to correctly classify members in the test set is determined. In some embodiments, this computation is performed several times for a given combination of molecular markers. In each iteration of the computation, the members of the training population are randomly assigned to the training set and the test set. Then, the quality of the combination of molecular markers is taken as the average of each such iteration of the decision tree computation.

5.14.10 Evolutionary Methods

Inspired by the process of biological evolution, evolutionary methods of classifier design employ a stochastic search for an optimal classifier. In broad overview, such methods create several classifiers—a population—from a combination of genes described in the present invention. Each classifier varies somewhat from the other. Next, the classifiers are scored on expression data across the training population. In keeping with the analogy with biological evolution, the resulting (scalar) score is sometimes called the fitness. The classifiers are ranked according to their score and the best classifiers are retained (some portion of the total population of classifiers). Again, in keeping with biological terminology, this is called survival of the fittest. The classifiers are stochastically altered in the next generation—the children or offspring. Some offspring classifiers will have higher scores than their parent in the previous generation, some will have lower scores. The overall process is then repeated for the subsequent generation: The classifiers are scored and the best ones are retained, randomly altered to give yet another generation, and so on. In part, because of the ranking, each generation has, on average, a slightly higher score than the previous one. The process is halted when the single best classifier in a generation has a score that exceeds a desired criterion value. More information on evolutionary methods is found in, for example, Duda, Pattern Classification, Second Edition, 2001, John Wiley & Sons, Inc.

5.14.11 Bagging, Boosting and the Random Subspace Method

Bagging, boosting and the random subspace method are combining techniques that can be used to improve weak classifiers. These techniques are designed for, and usually applied to, decision trees. In addition, Skurichina and Duin provide evidence to suggest that such techniques can also be useful in linear discriminant analysis.

In bagging, one samples the training set, generating random independent bootstrap replicates, constructs the classifier on each of these, and aggregates them by a simple majority vote in the final decision rule. See, for example, Breiman, 1996, Machine Learning 24, 123-140; and Efron & Tibshirani, An Introduction to Boostrap, Chapman & Hall, New York, 1993.

In boosting, classifiers are constructed on weighted versions of the training set, which are dependent on previous classification results. Initially, all objects have equal weights, and the first classifier is constructed on this data set. Then, weights are changed according to the performance of the classifier. Erroneously classified objects (molecular markers in the data set) get larger weights, and the next classifier is boosted on the reweighted training set. In this way, a sequence of training sets and classifiers is obtained, which is then combined by simple majority voting or by weighted majority voting in the final decision. See, for example, Freund & Schapire, "Experiments with a new boosting algorithm," Proceedings 13$^{th}$ International Conference on Machine Learning, 1996, 148-156.

To illustrate boosting, consider the case where there are two trait extremes exhibited by the population under study, extreme phenotype 1 (e.g., severe osteoarthritis), and extreme phenotype 2 (e.g., no osteoarthritis). Given a vector of predictor molecular marker X selected in step 214, a classifier G(X) produces a prediction taking one of the type values in the two value set: {extreme phenotype 1, extreme phenotype 2}. The error rate on the training sample is $$\overline{err} = \frac{1}{N}\sum_{i=1}^{N} I(y_i \neq G(x_i))$$

where N is the number of subjects in the training set (the sum total of the subjects that have either extreme phenotype 1 or extreme phenotype 2). For example, if there are 49 organisms that have severe osteoarthritis and 72 organisms that have no osteoarthritis under study, N is 121.

A weak classifier is one whose error rate is only slightly better than random guessing. In the boosting algorithm, the weak classification algorithm is repeatedly applied to modified versions of the data, thereby producing a sequence of weak classifiers $G_m(x)$, m,=1, 2, . . . , M. The predictions from all of the classifiers in this sequence are then combined through a weighted majority vote to produce the final prediction:

$$G(x) = \text{sign}\left(\sum_{m=1}^{M} \alpha_m G_m(x)\right)$$

Here $\alpha_1, \alpha_2, \ldots, a_M$ are computed by the boosting algorithm and their purpose is to weigh the contribution of each respective $G_m(x)$. Their effect is to give higher influence to the more accurate classifiers in the sequence.

The data modifications at each boosting step consist of applying weights $W_1, W_2, \ldots, w_n$ to each of the training observations (xJ, yj), i=1, 2, . . . , N. Initially all the weights are set to $w_j=1/N$, so that the first step simply trains the classifier on the data in the usual manner. For each successive iteration m=2, 3, . . . , M the observation weights are individually modified and the classification algorithm is reapplied to the weighted observations. At stem m, those observations that were misclassified by the classifier $G_m\_i(x)$ induced at the previous step have their weights increased, whereas the weights are decreased for those that were classified correctly. Thus as iterations proceed, observations that are difficult to correctly classify receive ever-increasing influence. Each successive classifier is thereby forced to concentrate on those training observations that are missed by previous ones in the sequence.

The exemplary boosting algorithm is summarized as follows:
1. Initialize the observation weights $w_j=1/N$, i=1, 2, . . . , N.
2. For m=1 to M:
   (a) Fit a classifier $G_m(x)$ to the training set using weights w.
   (b) Compute $$err_m = \frac{\sum_{i=1}^{N} w_i I(y_i \neq G_m(x_i))}{\sum_{i=1}^{N} w_i}$$

(c) Compute $\alpha_m = \log((1-err_m)/err_m)$.
   (d) Set $w \leftarrow (w, -\exp K - I(y_1 \neq G_w(x,))], *=1, 2, \ldots, N$.
3. Output $$G(x) = \text{sign}\left[\sum_{m=1}^{M} \alpha_m G_m(x)\right]$$

In the algorithm, the current classifier $G_m(x)$ is induced on the weighted observations at line 2a. The resulting weighted error rate is computed at line 2b. Line 2c calculates the weight $\alpha_m$ given to $G_m(x)$ in producing the final classifier $G(x)$ (line 3). The individual weights of each of the observations are updated for the next iteration at line 2d. Observations misclassified by $G_m(x)$ have their weights scaled by a factor $\exp(\alpha_m)$, increasing their relative influence for inducing the next classifier $G_{m+1}(x)$ in the sequence. In some embodiments, modifications of the Freund and Schapire, 1997, Journal of Computer and System Sciences 55, pp. 119-139, boosting method are used. See, for example, Hasti et al., The Elements of Statistical Learning, 2001, Springer, N.Y., Chapter 10. In some embodiments, boosting or adaptive boosting methods are used.

In some embodiments, modifications of Freund and Schapire, 1997, Journal of Computer and System Sciences 55, pp. 119-139, are used. For example, in some embodiments, feature preselection is performed using a technique such as the nonparametric scoring methods of Park et al., 2002, Pac. Symp. Biocomput. 6, 52-63. Feature preselection is a form of dimensionality reduction in which the genes that discriminate between classifications the best are selected for use in the classifier. Then, the LogitBoost procedure introduced by Friedman et al., 2000, Ann Stat 28, 337-407 is used rather than the boosting procedure of Freund and Schapire. In some embodiments, the boosting and other classification methods of Ben-Dor et al., 2000, Journal of Computational Biology 7, 559-583 are used in the present invention. In some embodiments, the boosting and other classification methods of Freund and Schapire, 1997, Journal of Computer and System Sciences 55, 119-139, are used.

In the random subspace method, classifiers are constructed in random subspaces of the data feature space. These classifiers are usually combined by simple majority voting in the final decision rule. See, for example, Ho, "The Random subspace method for constructing decision forests," IEEE Trans Pattern Analysis and Machine Intelligence, 1998; 20(8): 832-844.

5.14.12 Other Mathematical Models

The pattern classification and statistical techniques described above are merely examples of the types of classifiers that can be used to construct a classifier. Moreover, combinations of the techniques described above can be used. Some combinations, such as the use of the combination of decision trees and boosting, have been described. However, many other combinations are possible. In addition, other techniques in the art such as Projection Pursuit and Weighted Voting can be used to construct classifiers in instances of step 216.

5.15 Implementing the Invention

The present invention provides methods and systems for screening molecular markers to identify classifiers and/or for identifying classifiers for a trait and allows for the configuration of classifiers based on combinations of a large number of molecular markers. The invention provides a selection process for reducing the potential large number of candidate molecular markers and/or combinations thereof down to a manageable number which can be evaluated in one or more mathematical models to derive one or more classifiers.

Some embodiments of the invention are preferably implemented on a computer system having a processor and a memory unit. The embodiments may be implemented as one or more software programs operating on a general purpose computer, such as a personal computer or workstation, or as dedicated special purpose hardware components. The invention allows for an identification of classifiers while reducing the system requirements. It provides techniques for consideration of a large number of potential molecular markers in the classifier identification process with limited memory and computational requirements.

Some embodiments of the invention provide a data-driven selection of a subset of the candidate molecular markers based on their discrimination ability. Thus, it becomes possible to start out with a large group of potentially interesting molecular markers and to automatically prune the set of candidate molecular markers so that the computer system can handle the classifier identification process more efficiently, i.e. within less processing time and less memory space. This becomes more important as combinations of the molecular markers are generated in the classifier identification process and mathematical models are applied to each combination to derive classifiers, which may be a computationally expensive process, in particular when iterative techniques are applied, such as clustering, decision trees, neural networks, or evolutionary methods. Since the possible number of combinations grows almost exponentially with the number of candidate molecular markers, the processing time for the classifier evaluation become a serious problem. The pruning of candidate molecular markers allows for the consideration of two, three, four and more combinations of candidate molecular markers as basis for the classifiers. It enables the evaluation of a large number of classifiers based on molecular markers showing a promising discrimination ability and supersedes a computer resource consuming evaluation of classifiers based on molecular markers which are likely not contributing to the final trait discrimination. Thus, the invention can be implemented on a computer having less computational power and memory while the quality of the derived classifiers is maintained. On the other hand, the invention allows for the consideration of more molecular markers, which are potentially interesting for a given application (trait), with the same available system resources resulting in a possible higher classification accuracy for the derived classifiers.

The invention further provides a data-driven selection of the derived classifiers to remove classifiers and/or molecular markers which do not significantly contribute to the trait discrimination in the later application phase. This automatic pruning step evaluates the discrimination power of the individual classifiers to reduce the necessary system requirements of a diagnostic system applying the selected classifiers for the wide variety of possible medical applications. Thus, a diagnostic system configured with the identified classifiers needs less computational power and memory and may be implemented on a smaller, less expensive device. This becomes more important when the applied mathematical models are more complex and powerful. Examples of complex classifiers are described in section 5.14 of this description and include, e.g. neural networks, nearest neighbor classifiers, decision tress, etc. The invention enables the operation of optimized combinations of complex classifiers on diagnostic devises with limited resources.

5.16 Embodiments of the Invention

6. EXAMPLES

Computer systems, computer program products, methods, and kits for providing health care have been disclosed. What follows are select examples that illustrate the utility and value of the present invention.

6.1 Evaluating Osteoarthritis Classifiers Using ROC Curves

This example demonstrates the use of an embodiment of the invention to identify individuals with mild osteoarthritis. Osteoarthritis is a form of degenerative joint disease that involves the deterioration of and changes to the cartilage and bone. In response to inflammation in and about the joint, the body responds with bony recalcification around the joint structure. This process can be slow and gradual with minimal outward symptoms, or more rapidly progressive with significant pain and discomfort. Arthritic changes can occur in response to infection and injury of the joint as well.

Step 202—Generation of a Training Population.

Blood samples were taken from 44 test individuals not having any symptoms of osteoarthritis and 50 individuals having mild osteoarthritis using the methods described in Section 5.2. A molecular marker profile resulting in data for molecular marker products of the entire human genome was measured from each of these samples. This gene expression profile data together with knowledge of which subjects have osteoarthritis and which do not constitutes the training population 44. The 44 test individuals that do not have any symptoms of osteoarthritis constitute one trait subgroup within the training population and the 50 individuals having mild osteoarthritis constitute another trait subgroup within the training population.

Steps 204-218.

The training population collected in step 202 was used in order to identify combinations of genes that can serve as a classifier to differentiate mild osteoarthritis from non-osteoarthritis. Thus, the classifiers developed in this example are designed to yield a positive score when they predict that a subject has mild osteoarthritis and a negative score when they predict that the subject is in the control population. Using the approach described in Section 5.1, two specific classifiers were developed: 100000252 and 100000511. Classifier 100000252 comprises six genes and has the format: SCORE=−1.839+0.8*HSP90AA1 1.5525*IKBKAP+ 1.1O184*IL13RA1+O.78923*LAMC1−1.3974−*MAFB+ 1.0602*PF4.

Classifier 10000051 1 comprises nine genes and has the format: SCORE=−4.3754+0.10276*EGR1−1.1697*G2AN+ 0.88767*HSP90AA1 0.55785*IKBKAP+0.940− 15*IL13RA1+O.67515*LAMC1−1.5068*MAFB+ 1.0798*PF4+0.4007*TNFAIP6.

Here, EGR1, G2AN, HSP90AA1, IKBKAP, IL13RA1, LAMC1, MAFB, and TNFAIP6 are genes that were identified in step 204 and validated in step 208 (Section 5.1) for their ability to discriminate between subjects that have mild osteoarthritis and subjects that do not have osteoarthritis.

Step 220.

Figure 8:
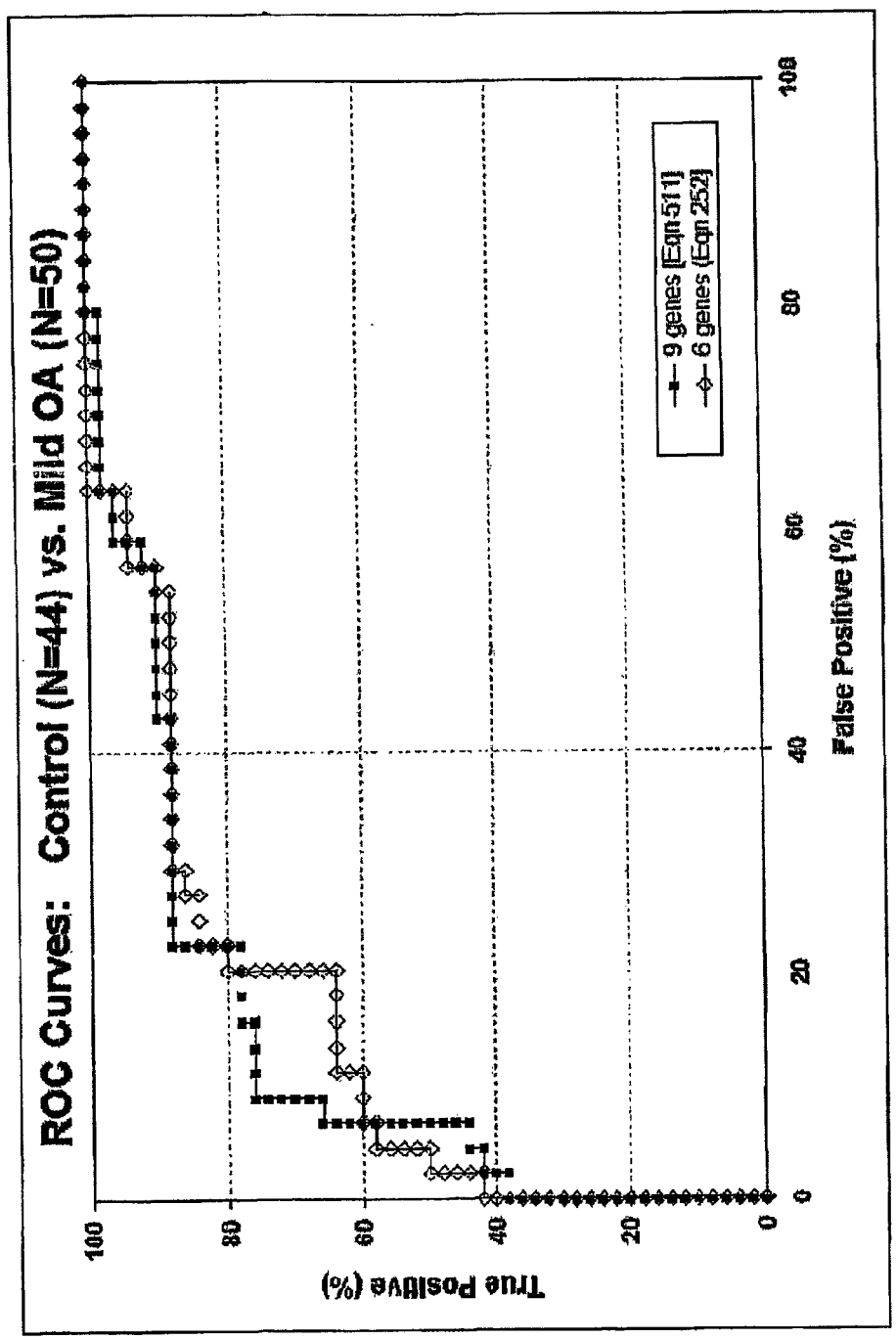
FIG. 8 illustrates ROC curves corresponding to two candidate classifiers for osteoarthritis computed in accordance with one embodiment of the present invention.

To judge which classifier is more suitable as a classifier for mild osteoarthritis, a ROC curve was computed for both classifiers using the gene expression data from the 44 test individuals not having any symptoms of osteoarthritis and the 50 individuals having mild osteoarthritis. The results of the ROC computation are illustrated in FIG. 8. The area under each ROC was computed. From this computation, it was determined that the area under the ROC curve corresponding to classifier 100000252 was 0.863 whereas the area under the ROC curve corresponding to classifier 1000005 11 was 0.81 69.

Step 224.

In some embodiments, a classifier can be constructed that includes both classifiers 100000252 and 10000051 1 using the voting methods described in Section 5.1. In alternative embodiments, classifier 100000252 is selected to serve as a classifier for mild osteoarthritis because it generated a larger area under the ROC curve corresponding to the classifier when tested against the training population.

6.2 Identified Molecular Markers and Molecular Marker Data Measurement Techniques Molecular markers useful for input into one or more steps of the invention and techniques for measuring data values of such molecular markers, can be found in U.S. patent application Ser. No. 10/601,518, filed Jun. 20, 2003, U.S. patent application Ser. No. 10/802,875, filed Mar. 12, 2004, U.S. patent application Ser. No. 10/809,675, filed Mar. 25, 2004, U.S. patent application Ser. No. 10/268,730, filed Oct. 9, 2002, U.S. patent application Ser. No. 09/477,148, filed Jan. 4, 2000, U.S. patent application Ser. No. 60/115,125, filed Jan. 6, 1999; and U.S. patent application Ser. No. 60/581,977, filed Jun. 21, 2004 each of which is hereby incorporated herein by reference in its entirety.

6.3 Construction of Classifiers for Manic Depression Syndrome

This example demonstrates the use of the claimed invention to identify biomarkers to differentiate manic depression syndrome from non manic depression syndrome and use of same. As used herein, "manic depression syndrome" (MDS) refers to a mood disorder characterized by alternating mania and depression.

Step 202.

Blood samples were taken from patients who were diagnosed with manic depression as defined herein. In each case, the diagnosis of manic depression was corroborated by a skilled Board certified physician. Molecular marker data was measured for each of the molecular markers of the entire human genome using blood samples from individuals who were identified as having manic depression as described herein and individuals not having manic depression. Molecular marker data for both trait subgroups were compared and gene expression profiles for each trait subpopulation compared using commercially available GeneSpring™ softwares. Hybridizations to create the gene expression profiles were done using Affymetrix® GeneChip® platforms (U133A and U133 Plus 2.0) as described herein (data not shown). Samples from patients were clustered into two trait subgroups. The first trait subgroup included patients who have manic depression and the second trait subgroup included patients who do not have manic depression (i.e., control individuals).

Step 204.

The Wilcox Mann Whitney rank sum test was used to identify molecular marker data that could discriminate between the control and diseased trait subgroups with a p value of <0.05.

Step 206.

Molecular markers were selected from those identified with p value of <0.05 and the ability to discriminate between the control and diseased trait subgroups were confirmed using quantitative RT-PCR.

Steps 214-218.

Eight candidate molecular markers were chosen and an exhaustive analysis of all possible combinations of said molecular markers were considered. Molecular marker data for each of the eight candidate molecular markers was obtained for each member of the training population and logistic regression applied to the molecular marker data so as to develop multiple classifiers. Each classifier was ranked on the basis of area under the curve and those classifiers with an ROC of greater than 0.9 chosen.

6.4 Construction of Classifiers for Predicting Response to Treatment

This example demonstrates the use of an embodiment of the invention to identify a classifier for predicting the response of a subject to treatment.

Step 202.

Blood samples are taken from patients (for example patients with a disease) who are going to enter into treatment (for the disease), or who are already undergoing treatment, but at a timepoint before being able to determine how the patients will respond to treatment. In one embodiment, blood samples are taken from patients who are about to enter into a clinical trial for a new treatment, or who are in the early stages of a clinical trial. Preferably blood samples are processed so as to preserve the RNA and/or the protein products of the molecular markers. More preferably the blood samples are processed immediately, within 1 hour, 2 hours, 3 hours, 4 hours, 5 hours, 6 hours, 10 hours, 12, hours, 18 hours or 24 hours from having taken the blood samples from the patients.

Subsequent to when the blood samples are taken, patients continue to be monitored for response to treatment using traditional diagnostic methods and grouped into trait subgroups on the basis of the response to treatment. For example, trait subgroups can include patients with a positive response and no negative side effects, patients with a positive response and mild side effects, patients with a negative response, patients with a toxic response, and the like. In some embodiments, the evaluation of response to treatment can take days, weeks, months or years. In some embodiments, data as described in step 202 of Section 5.1 and Section 5.3 is obtained upon processing of the blood sample. In other embodiments, data of step 202 is obtained only after a determination of response to treatment has been made. In all cases, molecular marker data is obtained from a blood sample taken at a timepoint prior to being able to determine response to treatment. Once trait subgroups are identified on the basis of response to treatment, gene expression profiles of blood samples of each trait subgroup are compared using GeneSpring™ software analysis. Hybridizations to create the gene expression profiles are done using Affymetrix® GeneChip® platforms (U133A and U133 Plus 2.0) platforms (U133A and U133 Plus 2.0) as described herein. Samples from patients are clustered into two trait subgroups on the basis of the response to treatment. For example, one trait subgroup demonstrates a positive response to treatment whereas the second trait subgroup demonstrates a toxic response to treatment.

Step 204.

The Wilcox Mann Whitney rank sum test is used to identify candidate molecular markers by identifying molecular marker data that discriminates between the response and non-response trait subgroups with a p value of <0.05 to obtain candidate molecular markers.

Step 206.

Additional molecular marker data for the candidate molecular markers are obtained using quantitative RT-PCR. Some candidate molecular markers are removed at this point should the quantitative RT-PCR data not confirm the ability of each candidate molecular marker to discriminate as between the response trait subgroups.

Steps 214-218.

Candidate molecular marker combinations are chosen and an exhaustive analysis of all possible combinations of molecular markers are tested. To test all possible combinations of molecular markers, logistic regression is applied to the molecular marker data so as to develop multiple classifiers. Each classifier is ranked on the basis of area under the curve using the training population. Those classifiers ranking with an ROC area under curve of greater than 0.9 are further evaluated using a scoring population which is not the training population. Note that the blood samples used for the scoring population are obtained at the same time point as the blood samples used for the training population (e.g., at a time prior to being able to determine response to treatment).

6.5 Construction of Classifiers for Determining a Trait of Interest 6.5.1

This example demonstrates the selection of the composition of the training population and the trait subgroups of the training population so as to result in classifiers which are useful to predict disease.

Step 202.

In order to predict disease, blood samples are taken from patients at a time when said patients are disease free. Preferably blood samples are processed so as to preserve the RNA and/or the protein products of all molecular markers of the entire genome of said individual. More preferably the blood samples are processed immediately, within 1 hour, 2 hours, 3 hours, 4 hours, 5 hours, 6 hours, 10 hours, 12, hours, 18 hours or 24 hours from having taken the blood samples from the patients.

Subsequent to when the blood samples are taken, patients continue to be monitored for development of said disease using traditional diagnostic methods. At a given time point, two trait subgroups are identified, namely individuals who develop said disease of interest and individuals who do not develop said disease of interest. In some embodiments, the timepoint at which trait subgroups are identified can take days, weeks, months or years. In some embodiments, data as described in step 202 of Section 5.1 and Section 5.3 is obtained upon processing of the blood sample. In other embodiments, data of step 202 is obtained only after a determination of trait subgroups has been made. In all cases, data is obtained from a blood sample taken at a timepoint prior to being able to determine disease. Once trait subgroups are identified gene expression profiles of the molecular marker data of the molecular marker products from the blood samples of each trait subgroup are compared using GeneSpring™ software analysis. Hybridizations to create the gene expression profiles are done using Affymetrix® GeneChip® platforms (U133A and U133 Plus 2.0) platforms (U133A and U133 Plus 2.0) as described herein and candidate molecular markers are identified where the molecular marker data is able to differentiate as between said two trait subgroups with a p value of <0.05. Said candidate molecular markers are subsequently processed as described in steps 206 to 226 to identify classifiers and molecular markers capable of predicting disease.

6.5.2

This example demonstrates the selection of the composition of the training population and the trait subgroups of the training population so as to result in classifiers which are useful to determine treatment compliance.

Step 202.

In order to determine treatment compliance, blood samples are taken from patients who are complying with said treatment of interest and patients who are not complying with said treatment. Preferably blood samples are processed so as to preserve the RNA and/or the protein corresponding to molecular markers of the entire genome of said individual. More preferably the blood samples are processed immediately, within 1 hour, 2 hours, 3 hours, 4 hours, 5 hours, 6 hours, 10 hours, 12, hours, 18 hours or 24 hours from having taken the blood samples from the patients.

Molecular marker data is obtained as described in step 202 of Section 5.1 and Section 5.3 upon processing of the blood sample. Hybridizations to create the gene expression profiles are done using Affymetrix® GeneChip® platforms (U133A and U133 Plus 2.0) platforms (U133A and U133 Plus 2.0) as described herein and candidate molecular markers are identified which differentiate as between patients who comply with said treatment of interest as compared with patients who do not comply with said treatment of interest with a p value of 0.05. Said candidate molecular markers are subsequently processed as described in steps 206 to 226 to identify classifiers and molecular markers capable of determining treatment compliance.

6.5.3

This example demonstrates the selection of the composition of the training population and the trait subgroups of the training population so as to result in classifiers which are useful to predict reoccurrence of disease.

Step 202.

In order to predict reoccurrence of disease, blood samples are taken from patients, all of whom have had a disease of interest, at a time when all of said patients are disease free. Preferably blood samples are processed so as to preserve the RNA and/or the protein corresponding to molecular markers of the entire genome of said individual. More preferably the blood samples are processed immediately, within 1 hour, 2 hours, 3 hours, 4 hours, 5 hours, 6 hours, 10 hours, 12, hours, 18 hours or 24 hours from having taken the blood samples from the patients.

Subsequent to when the blood samples are taken, patients continue to be monitored for reoccurence of said disease using traditional diagnostic methods. At a given time point, two trait subgroups are identified, namely individuals who develop reoccurrence of said disease of interest and individuals who do not develop said disease of interest. In some embodiments, the timepoint at which trait subgroups are identified can take days, weeks, months or years. In some embodiments, data as described in step 202 of Section 5.1 and Section 5.3 is obtained upon processing of the blood sample. In other embodiments, data of step 202 is obtained only after a determination of trait subgroups has been made. In all cases, data is obtained from a blood sample taken at a timepoint prior to being able to determine reoccurrence of disease. Once trait subgroups are identified molecular marker data of the molecular marker products from the blood samples of each trait subgroup are compared using GeneSpring™ software analysis. Hybridizations to create the gene expression profiles are done using Affymetrix® GeneChip® platforms (U133A ana U133 FMs' '2'.ü) platforms (U133A and U133 Plus 2.0) as described herein and candidate molecular markers are identified whose molecular marker data differentiates as between said two trait subgroups with a p value of <0.05. Said candidate molecular markers are subsequently processed as described in steps 206 to 226 to identify classifiers and molecular markers capable of predicting reoccurrence of disease.

6.5.4

This example demonstrates the use of classifiers used in series so as to diagnose a patient with a stage of disease, for example a specific stage of osteoarthritis.

We have identified previously four different stages of osteoarthritis; namely mild osteoarthritis, moderate osteoarthritis, marked osteoarthritis and severe osteoarthritis (see for example PCT patent application WO02070737 Entitled "Compositions and Methods relating to osteoarthritis"

In some instances it is useful to determine which stage of osteoarthritis an individual has, and more importantly to confirm that said patient does not have any other stage of osteoarthritis. For example if an individual has changed their lifestyle and lost weight to determine whether the osteoarthritis has regressed.

Classifiers of the invention are able to differentiate as between two subgroups. As such—multiple classifiers are required to specifically stage an individual.

A first classifier is developed which differentiates as between osteoarthritis and non-osteoarthritis. As described, a training population is selected comprised of two trait subgroups where said first trait subgroup is comprised of individuals having osteoarthritis and the second trait subgroup comprised of individuals not having osteoarthritis. Identification of candidate molecular markers which differentiate as between these two trait subgroups are identified as per step 202 and subsequently processed as described in steps 206 to 226 to identify classifiers and molecular markers capable of differentiating between osteoarthritis and non-osteoarthritis.

Similarly classifiers are identified which are capable of differentiating between (a) mild osteoarthritis and moderate osteoarthritis (b) moderate osteoarthritis and marked osteoarthritis (c) marked osteoarthritis and severe osteoarthritis.

In order to diagnose an individual as having marked osteoarthritis and not having mild osteoarthritis or severe osteoarthritis, a series of tests are applied. First a classifier which determines whether said patient has osteoarthritis or not is applied. Assuming said patient has osteoarthritis, a classifier is applied which determines whether said patient has either mild osteoarthritis or marked osteoarthritis. Assuming said patient has marked osteoarthritis,"! classiKeFis applied to determine whether said patient has marked osteoarthritis or severe osteoarthritis. The result of these series of classifiers can determine that said patient has marked osteoarthritis and does not have any other stage of osteoarthritis.

6.6 Construction of Classifiers for Determining a Trait of Interest (or Differentiating Between Two Traits of Interest) Using the Molecular Markers Identified in One of the Disclosed Tables While the examples described below suggest selection of molecular markers prior to generating all combinations of classifiers from the disclosed Tables can be based on a specific measure of statistical significance (p value) as disclosed for each molecular marker (see Table G and Table H) it must be appreciated that the selection of molecular markers may also be based on any other method disclosed in this application, such as differential fold change or even a combination of selection of p value and differential fold change. A skilled person in the art will recognize these other methods can also be used so as to permit the selection of subsets of the molecular markers to derive lists for which a reasonable number of combinations can be tested within the limits of the computer processing capacity. The skilled person will be able to transfer the details given in this section for examples based on a p value evaluation to carry out the selection based on other disclosed selection methods or selection methods known to him.

TABLE F

| | | Recommended Training Population | |
|---|---|---|---|
| Selected Table | Trait of Interest | Key Trait of Members of Trait Subgroup A | Key Trait of Members of Trait Subgroup B |
| Table 1A | Osteoarthritis and Hypertension | Members have both Osteoarthritis and Hypertension | Members have neither Osteoarthritis nor Hypertension |
| Table 1B | Osteoarthritis and Obesity | Members have both Osteoarthritis and Obesity | Members have neither Osteoarthritis nor Obesity |
| Table 1C | Osteoarthritis and Allergies | Members have both Osteoarthritis and Allergies | Members have neither Osteoarthritis nor Allergies |
| Table 1D | Osteoarthritis and Systemic Steroids | Members have both Osteoarthritis and are taking Systemic Steroids | Members have neither Osteoarthritis nor are taking Steroids |
| Table 1E | Hypertension | Members have Hypertension | Members do not have Hypertension |
| Table 1F | Obesity | Members are Obese | Members are not Obese |
| Table 1G | Hypertension | Members have Hypertension. Members have Hypertension and Osteoarthritis. | Members do not have Hypertension Members do not have Osteoarthritis |
| Table 1H | Hypertension and Osteoarthritis | Members have Hypertension and Osteoarthritis | Members do not have either Hypertension or Osteoarthritis |
| Table 1I | Obesity | Members are Obese | Members are not Obese |
| | | Members have Obesity and Osteoarthritis | Members do not have Osteoarthritis. |
| Table 1J | Obesity and Osteoarthritis | Members have Osteoarthritis and are also Obese | Members do not have either Osteoarthritis and are not Obese |
| Table 1K | Allergies | Members have Allergies | Members do not have Allergies |
| | | Members have Allergies and Osteoarthritis | Members do not have Osteoarthritis |
| Table 1L | Allergies and Osteoarthritis | Members have Allergies and Osteoarthritis | Members do not have either Allergies or Osteoarthritis |
| Table 1M | Systemic Steroids | Members have been taking Systemic Steroids | Members have not been taking Systemic Steroids |
| | | Members have been taking Systemic Steroids and have Osteoarthritis | Members do not have Osteoarthritis. |

TABLE F-continued

|  | | Recommended Training Population | |
|---|---|---|---|
| Selected Table | Trait of Interest | Key Trait of Members of Trait Subgroup A | Key Trait of Members of Trait Subgroup B |
| Table 1N | Systemic Steroids and Osteoarthritis | Members have Osteoarthritis and have been taking Systemic Steroids | Members do not have Osteoarthritis and have not been taking systemic Steroids |
| Table 1O | Taking Birth Control | Members taking Birth Control | Members not taking Birth Control |
|  | Taking Prednisone | Members taking Prednisone | Members not taking Prednisone |
|  | Taking Hormone Replacement Therapy | Members taking Hormone Replacement Therapy | Members not taking Hormone Replacement Therapy |
| Table 1P | Type II Diabetes | Members have Type II Diabetes | Members do not have Type II Diabetes |
| Table 1Q | Hyperlipidemis | Members have Hyperlipidemia | Members do not have Hyperlipidemia |
| Table 1R | Lung Disease | Members have Lung Disease | Members do not have Lung Disease |
| Table 1S | Bladder Cancer | Members have Bladder Cancer | Members do not have Bladder Cancer |
| Table 1T | Early Stage Bladder Cancer | Members have Early Stage Bladder Cancer | Members do not have Bladder Cancer |
|  |  | Members have Early Stage Bladder Cancer | Members do not have Early Stage Bladder Cancer |
|  | Late Stage Bladder Cancer | Members have Late Stage Bladder Cancer | Members do not have Bladder Cancer |
|  |  | Members have Late Stage Bladder Cancer | Members do not have Late Stage Bladder Cancer |
| Table 1U | Coronary Artery Disease (CAD) | Members have CAD | Members do not have CAD |
| Table 1V | Rheumatoid Arthritis (RA) | Members have RA | Members do not have RA |
| Table 1W | Rheumatoid Arthritis (RA) | Members have RA | Members do not have RA |
| Table 1X | Depression | Members have Depression | Members do not have Depression |
| Table 1Y | Stage of Osteoarthritis - Mild | Members have Mild OA | Members do not have OA |
|  | Stage of Osteoarthritis - Moderate | Members have Moderate OA | Members do not have OA |
|  | Stage of Osteoarthritis - Marked | Members have Marked OA | Members do not have OA |
|  | Stage of Osteoarthritis - Severe | Members have Severe OA | Members do not have OA |
| Table 1Z | Liver Cancer | Members have Liver Cancer | Members do not have Liver Cancer |
| Table 1Z(b) | Liver Cancer | Members have Liver Cancer | Members do not have Liver Cancer |
| Table 1AA | Schizophrenia | Members have Schizophrenia | Members do not have Schizophrenia |
| Table 1AB | Chagas Disease | Members have Chagas Disease | Members do not have Chagas Disease |
| Table 1AC | Asthma | Members have Asthma and OA | Members have OA |
| Table 1AD | Asthma | Members have Asthma | Members do not have Asthma |
| Table 1AE | Lung Cancer | Members have Lung Cancer | Members do not have Lung Cancer |
| Table 1AG | Hypertension | Members have Hypertension | Members do not have Hypertension |
| Table 1AH | Obesity | Members have Obesity | Members do not have Obesity |
| Table 1AI | Ankylosing Spondylitis | Members have Ankylosing Spondylitis | Members do not have Ankylosing Spondylitis |

TABLE F-continued

| | | Recommended Training Population | |
|---|---|---|---|
| Selected Table | Trait of Interest | Key Trait of Members of Trait Subgroup A | Key Trait of Members of Trait Subgroup B |
| Table 2 | Osteoarthritis | Members have Osteoarthritis | Members do not have Osteoarthritis |
| Table 3A | Schizophrenia or Manic Depression Syndrome (MDS) | Members have Schizophrenia | Members have MDS |
| Table 3B | Hepatitis or Liver Cancer | Members have Hepatitis | Members have Liver Cancer |
| Table 3C | Bladder Cancer or Liver Cancer | Members have Bladder Cancer | Members have Liver Cancer |
| Table 3D | Bladder Cancer or Testicular Cancer | Members have Bladder Cancer | Members have Testicular Cancer |
| Table 3E | Testicular Cancer or Kidney Cancer | Members have Testicular Cancer | Members have Kidney Cancer |
| Table 3F | Liver Cancer or Stomach Cancer | Members have Liver Cancer | Members have Stomach Cancer |
| Table 3G | Liver Cancer or Colon Cancer | Members have Liver Cancer | Members have Colon Cancer |
| Table 3H | Stomach Cancer or Colon Cancer | Members have Stomach Cancer | Members have Colon Cancer |
| Table 3I | Rheumatoid Arthritis or Osteoarthritis | Members have Rheumatoid Arthritis | Members have Osteoarthritis |
| Table 3K | Chagas Disease or Heart Failure | Members have Chagas Disease | Members have Heart Failure |
| Table 3L | Chagas Disease or Coronary Artery Disease | Members have Chagas Disease | Members have CAD |
| Table 3N | Coronary Artery Disease or Heart Failure | Members have CAD | Members have Heart Failure |
| Table 3P | Asymptomatic Chagas or Symptomatic Chagas | Members have Asymptomatic Chagas | Members have Symptomatic Chagas |
| Table 3Q | Alzheimer's or Schizophrenia | Members have Alzheimer's | Members have Schizophrenia |
| Table 3R | Alzheimer's or Manic Depression Syndrome | Members have Alzheimer's | Members have Manic Depression |
| Table 4A | Osteoarthritis | Members have Osteoarthritis | Members do not have Osteoarthritis |
| Table 4B | Osteoarthritis | Members have Osteoarthritis | Members do not have Osteoarthritis |
| Table 4C | Mild Osteoarthritis | Members have Mild Osteoarthritis | Members do not have Osteoarthritis |
| Table 4D | Mild Osteoarthritis | Members have Mild Osteoarthritis | Members do not have Osteoarthritis |
| Table 4E | Moderate Osteoarthritis | Members have Moderate Osteoarthritis | Members do not have Osteoarthritis |
| Table 4F | Moderate Osteoarthritis | Members have Moderate Osteoarthritis | Members do not have Osteoarthritis |
| Table 4G | Marked Osteoarthritis | Members have Marked Osteoarthritis | Members do not have Osteoarthritis |
| Table 4H | Marked Osteoarthritis | Members have Marked Osteoarthritis | Members do not have Osteoarthritis |
| Table 4I | Severe Osteoarthritis | Members have Severe Osteoarthritis | Members do not have Osteoarthritis |
| Table 4J | Severe Osteoarthritis | Members have Severe Osteoarthritis | Members do not have Osteoarthritis |
| Table 4K | Mild Osteoarthritis or Moderate Osteoarthritis | Members have Mild Osteoarthritis | Members have Moderate Osteoarthritis |
| Table 4L | Mild Osteoarthritis or Moderate Osteoarthritis | Members have Mild Osteoarthritis | Members have Moderate Osteoarthritis |
| Table 4M | Mild Osteoarthritis or Marked Osteoarthritis | Members have Mild Osteoarthritis | Members have Marked Osteoarthritis |

TABLE F-continued

|  |  | Recommended Training Population | |
|---|---|---|---|
| Selected Table | Trait of Interest | Key Trait of Members of Trait Subgroup A | Key Trait of Members of Trait Subgroup B |
| Table 4N | Mild Osteoarthritis or Marked Osteoarthritis | Members have Mild Osteoarthritis | Members have Marked Osteoarthritis |
| Table 4O | Mild Osteoarthritis or Severe Osteoarthritis | Members have Mild Osteoarthritis | Members have Severe Osteoarthritis |
| Table 4P | Mild Osteoarthritis or Severe Osteoarthritis | Members have Mild Osteoarthritis | Members have Severe Osteoarthritis |
| Table 4Q | Moderate Osteoarthritis or Marked Osteoarthritis | Members have Moderate Osteoarthritis | Members have Marked Osteoarthritis |
| Table 4R | Moderate Osteoarthritis or Marked Osteoarthritis | Members have Moderate Osteoarthritis | Members have Marked Osteoarthritis |
| Table 4S | Moderate Osteoarthritis or Severe Osteoarthritis | Members have Moderate Osteoarthritis | Members have Severe Osteoarthritis |
| Table 4T | Moderate Osteoarthritis or Severe Osteoarthritis | Members have Moderate Osteoarthritis | Members have Severe Osteoarthritis |
| Table 4U | Marked Osteoarthritis or Severe Osteoarthritis | Members have Marked Osteoarthritis | Members have Severe Osteoarthritis |
| Table 4V | Marked Osteoarthritis or Severe Osteoarthritis | Members have Marked Osteoarthritis | Members have Severe Osteoarthritis |
| Table 5A | Psoriasis | Members have Psoriasis | Members do not have Psoriasis |
| Table 5B | Thyroid Disorder | Members have Thyroid Disorder | Members do not have Thyroid Disorder |
| Table 5C | Irritable Bowel Syndrome | Members have Irritable Bowel Syndrome | Members do not have Irritable Bowel Syndrome |
| Table 5D | Osteoporosis | Members have Osteoporosis | Members do not have Osteoporosis |
| Table 5E | Migraine Headaches | Members have Migraine Headaches | Members do not have Migraine Headaches |
| Table 5F | Eczema | Members have Eczema | Members do not have Eczema |
| Table 5G | NASH | Members have NASH | Members do not have NASH |
| Table 5H | Alzheimer's | Members have Alzheimers' | Members do not have Alzheimers' |
| Table 5I | Manic Depression Syndrome | Members have Manic Depression Syndrome | Members do not have Manic Depression Syndrome |
| Table 5J | Crohn's Colitis | Members have Crohn's Colitis | Members do not have Crohn's Colitis |
| Table 5K | Chronic Cholecystis | Members have Chronic Cholecystis | Members do not have Chronic Cholecystis |
| Table 5L | Heart Failure | Members have Heart Failure | Members do not have Heart Failure |
| Table 5M | Cervical Cancer | Members have Cervical Cancer | Members do not have Cervical Cancer |
| Table 5N | Stomach Cancer | Members have Stomach Cancer | Members do not have Stomach Cancer |
| Table 5O | Kidney Cancer | Members have Kidney Cancer | Members do not have Kidney Cancer |
| Table 5P | Testicular Cancer | Members have Testicular Cancer | Members do not have Testicular Cancer |
| Table 5Q | Colon Cancer | Members have Colon Cancer | Members do not have Colon Cancer |
| Table 5R | Hepatitis B | Members have Hepatitis B | Members do not have Hepatitis B |

TABLE F-continued

| | | Recommended Training Population | |
|---|---|---|---|
| Selected Table | Trait of Interest | Key Trait of Members of Trait Subgroup A | Key Trait of Members of Trait Subgroup B |
| Table 5S | Pancreatic Cancer | Members have Pancreatic Cancer | Members do not have Pancreatic Cancer |
| Table 5T | Asymptomatic Chagas | Members have Asymptomatic Chagas | Members do not have Asymptomatic Chagas |
| Table 5U | Symptomatic Chagas | Members have Symptomatic Chagas | Members do not have Symptomatic Chagas |
| Table 5V | Bladder Cancer | Members have Bladder Cancer | Members do not have Bladder Cancer |
| Table 6A | Cancer | Members have Cancer | Members do not have Cancer |
| Table 6B | Cardiovascular Disease | Members have Cardiovascular Disease | Members do not have Cardiovascular Disease |
| Table 6C | Neurological Disorders | Members have a Neurological Disorder | Members do not have a Neurological Disorder |
| Table 7A | Celebrex ® or Other Cox Inhibitor | Members taking Celebrex ® | Members taking non Celebrex ® Cox Inhibitor |
| Table 7B | Celebrex ® | Members taking Celebrex ® | Members not taking Celebrex ® |
| Table 7C | Vioxx ® | Members taking Vioxx ® | Members not taking Vioxx ® |
| Table 7D | Vioxx ® or Other Cox Inhibitor | Members taking Vioxx ® | Members taking non Vioxx ® Cox Inhibitor |
| Table 7E | NSAIDS | Members taking NSAIDS | Members not taking NSAIDS |
| Table 7F | Cortisone | Members taking Cortisone | Members not taking Cortisone |
| Table 7G | Visco Supplement | Members taking Visco Supplement | Members not taking Visco Supplement |
| Table 7H | Lipitor ® | Members taking Lipitor ® | Members not taking Lipitor ® |
| Table 7I | Smokers | Members are Smokers | Members are not Smokers |

Construction of Classifiers for Determining a Trait of Interest
Steps 202-204

In order to identify useful classifiers for a trait of interest, for example mild osteoarthritis, one or more of the tables listed in Table F above which have the same recommended training population can be used. Thus for example, for mild osteoarthritis, one can select one or more of Tables IY; 4C; 4D. These molecular markers listed resulted from application of Steps 202-204 as outlined in FIG. 2A as more fully described for each Table herein. Once one or more Tables have been selected, it is helpful to select a subset of the molecular markers in the Table or Tables before proceeding to step 206. For example, combining Tables IY, 4C and 4D and selecting molecular markers where the molecular marker data demonstrates an ability to differentiate as between the two trait subgroups with a p value of less than 0.0001 results in 212 molecular markers. Note that p values resulting from the molecular marker data for each molecular marker identified in any of Tables IA to 7I can be found in Tables 8A or Tables 8B below.

Table 8A identifies molecular markers via the Clone ID of the probe used to hybridize to the molecular marker products. The Clone ID corresponds to the Clone ID found in tables IA; 1AC; IB; 1C; ID; IE; IF; IG; IH; II; U; IK; IL; IM; IN; 10; IP; IQ; IR; IV; IX; IY; IZ; 2; 4A; 4C; 4E; 4G; 4I; 4K; 4M; 4O; 4Q; 4S; 4V; 7A; 7B; 7C; 7D; 7E; 7H; and 7I (ie those Tables generated using the ChondroChip™ as outlined herein). Table 8A then identifies the corresponding Table in which the molecular market—is identified via said Clone ID. Finally the p value of the molecular marker data obtained using the ChondroChip™ is listed. Note that Table 8A is sorted first by Table number and then by p value.

Table 8B identifies molecular markers via the Affymetrix® Spot ID of the probe pair used to hybridize to the molecular marker products. The Affy Spot ID corresponds to the Affy Spot ID found in tables Tables IAA; LAB; IAD; IAE; IAG; IAH; IAT; IS; IT; IU; IW; 1Z(b); 3A; 3B; 3C; 3D; 3E; 3F; 3G; 3H; 31; 3K; 3L; 3P; 3Q; 3R; 4B; 4D; 4F; 4H; 4J; 4L; 4N; 4P; 4R; 4T; 4V; 5A; 5B; 5C; 5D; 5EE; 5F; 5G; 5H; 51; 5J; 5K; 5L; 5M; 5N; 50; 5P 5Q; 5R; 5S; 5T; 5U; 5V; 6A; 6B; 6C; 7F; and 7G (ie those Tables generated using the Affymetrix™ Gene Chip as outlined herein). Table 8B then identifies the corresponding Table in which the molecular marker is identified via said Affymetrix® Spot ID. Finally the p value of the molecular marker data obtained using the ChondroChip™ is listed. Note that Table 8B is sorted first by Table number and then by p value.

Step 206

For the 212 selected molecular markers—a training population is chosen having two trait subgroups where the two trait subgroups are outlined in Table F above as corresponding to the Tables used to select the molecular markers, thus in this example, the first trait subgroup is members having mild osteoarthritis and the second trait subgroup is members not having osteoarthritis. A blood sample from each member of the training population is obtained and processed using techniques as described herein and mRNA isolated. The resulting mRNA is reverse transcribed using ABFs High Capacity cDNA Archive Kit and the cDNA is then used for quantitative RT-PCR so as to collect molecular marker data for application to a logistic regression model. Amplification primers are designed for each of the 212 molecular markers. Preferably primers are chosen which amplify across an intronjunction. Quantitative Real Time PCR is performed using Qiagen's QuantiTect™ Sybr Green RT-PCR kit and data corresponding to the level of RNA for each of the molecular markers Steps 214-218.

From the 212 candidate molecular markers selected, an exhaustive analysis of all possible combinations of molecular markers using the molecular marker data obtained using quantitative RT-PCR data is tested using logistic regression so as to develop multiple classifiers. Each classifier is ranked on the basis of area under the curve using the training population. Those classifiers ranking with an ROC area under curve of greater than 0.8 are further evaluated using a scoring population which is not the training population. Those classifiers resulting in an ROC area under the curve of greater than 0.7 as determined using the scoring population are selected. Each of The selected classifiers is comprised of a combination of molecular markers from one of Tables IY, 4C and 4D.

Use of the Selected Classifier to Diagnose an Individual as Having Mild Osteoarthritis.

Any of the selected classifiers can be used to diagnose an individual as having mild osteoarthritis. A blood sample from a test individual is processed using techniques as described herein to isolate mRNA. mRNA is reverse transcribed using ABFs High Capacity cDNA Archive Kit and the cDNA is then used for quantitative RT-PCR. Amplification primers are designed for each of the molecular markers in the classifier selected which amplify across an intronjunction. Quantitative Real Time PCR is performed using Qiagen's QuantiTect™ Sybr Green RT-PCR kit and data corresponding to the level of RNA for each of the molecular markers of the selected classifier obtained. The data is then used in conjunction with the logistic regression classifier so as to convert the data resulting from the Quantitative RT-PCR into a single number. If the number is greater than 0—the test individual is diagnosed as having mild osteoarthritis is the number is less than 0 the test individual is diagnosed as not having osteoarthritis.

7. REFERENCES CITED

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that comprises a computer program mechanism embedded in a computer readable storage medium. For instance, the computer program product could contain the program modules shown in FIG. 1. These program modules may be stored on a CD-ROM, DVD, magnetic disk storage product, or any other computer readable data or program storage product. The software modules in the computer program product can also be distributed electronically, via the Internet or otherwise, by transmission of a computer data signal (in which the software modules are embedded) on a carrier wave.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

---

Lengthy table referenced here

US07991557-20110802-T00001

Please refer to the end of the specification for access instructions.

---

Lengthy table referenced here

US07991557-20110802-T00002

Please refer to the end of the specification for access instructions.

---

LENGTHY TABLES

The patent contains a lengthy table section. A copy of the table is available in electronic form from the USPTO web site (http://seqdata.uspto.gov/?pageRequest=docDetail&DocID=US07991557B2). An electronic copy of the table will also be available from the USPTO upon request and payment of the fee set forth in 37 CFR 1.19(b)(3).

---

What is claimed:

1. A method for profiling gene expression in a human test subject, the method comprising:
    a) measuring a level of expression in a blood sample of said test subject of each gene of a set of genes consisting of heat shock protein 90 kDa alpha (cytosolic), class A member 1 (HSP90AA1); inhibitor of kappa light polypeptide gene enhancer in B-cells, kinase complex-associated protein (IKBKAP); interleukin 13 receptor, alpha 1 (IL13RA1); laminin, gamma 1 (LAMC1); v-maf musculoaponeurotic fibrosarcoma oncogene homolog B (MAFB); and platelet factor 4 (PF4), thereby obtaining a sample dataset; and
    b) applying a classifier to said sample dataset to thereby classify said test subject into a class representing human subjects having mild osteoarthritis or a class representing human subjects not having osteoarthritis, wherein said classifier is able to discriminate between human subjects having mild osteoarthritis and human subjects not having osteoarthritis, and wherein said classifier is derived from data representing a level of expression of each gene of said set of genes in blood samples of human subjects having mild osteoarthritis and in blood samples of human subjects not having osteoarthritis, thereby profiling gene expression in a human test subject.

2. The method of claim 1, wherein said classifier is based on a multiple regression equation.

3. The method of claim 1, wherein said classifier has a format:

$$SCORE=-1.839+0.8*HSP90AA1-1.5525*IKBKAP+1.10184*IL13RA1+0.78923*LAMC1-1.3974*MAFB+1.0602*PF4, \text{ where}$$

SCORE, if positive, classifies said test subject into said class representing human subjects having mild osteoarthritis;

SCORE, if negative, classifies said test subject into said class representing human subjects not having osteoarthritis;

HSP90AA1 represents said level of expression of heat shock protein 90 kDa alpha cytosolic), class A member 1 (HSP90AA1) in said sample of said test subject;

IKBKAP represents said level of expression of inhibitor of kappa light polypeptide gene enhancer in B-cells, kinase complex-associated protein (IKBKAP) in said sample of said test subject;

IL13RA1 represents said level of expression of interleukin 13 receptor, alpha 1 (IL13RA1) in said sample of said test subject;

LAMC1 represents said level of expression of laminin, gamma in said sample of said test subject;

MAFB represents said level of expression of v-maf musculoaponeurotic fibrosarcoma oncogene homolog B (MAFB) in said sample of said test subject; and PF4 represents said level of expression of platelet factor 4 (PF4) in said sample of said test subject.

4. The method of claim 1, wherein said applying said classifier to said sample dataset comprises using a computer programmed to apply said classifier to a dataset representing a level of expression of each gene of said set of genes in a blood sample of a human individual to thereby classify said human individual into said class representing human subjects having mild osteoarthritis or said class representing human subjects not having osteoarthritis.

5. The method of claim 4, wherein said classifier is based on a multiple regression equation.

6. The method of claim 4, wherein said classifier has a format:

$$SCORE=-1.839+0.8*HSP90AA1-1.5525*IKBKAP+1.10184*IL13RA1+0.78923*LAMC1-1.3974*MAFB+1.0602*PF4, \text{ where}$$

SCORE, if positive, classifies said test subject into said class representing human subjects having mild osteoarthritis;

SCORE, if negative, classifies said test subject into said class representing human subjects not having osteoarthritis;

HSP90AA1 represents said level of expression of heat shock protein 90 kDa alpha (cytosolic), class A member 1 (HSP90AA1) in said sample of said test subject;

IKBKAP represents said level of expression of inhibitor of kappa light polypeptide gene enhancer in B-cells, kinase complex-associated protein (IKBKAP) in said sample of said test subject;

IL13RA1 represents said level of expression of interleukin 13 receptor, alpha 1 (IL13RA1) in said sample of said test subject;

LAMC1 represents said level of expression of laminin, gamma 1 (LAMC1) in said sample of said test subject;

MAFB represents said level of expression of v-maf musculoaponeurotic fibrosarcoma oncogene homolog B (MAFB) in said sample of said test subject; and PF4 represents said level of expression of platelet factor 4 (PF4) in said sample of said test subject.

7. A method for profiling gene expression in a human test subject, the method comprising:

a) obtaining a sample dataset representing a level of expression in a blood sample of said test subject of each gene of a set of genes consisting of heat shock protein 90 kDa alpha (cytosolic), class A member 1 (HSP90AA1); inhibitor of kappa light polypeptide gene enhancer in B-cells, kinase complex-associated protein (IKBKAP); interleukin 13 receptor, alpha 1 (IL13RA1); laminin, gamma 1 (LAMC1); v-maf musculoaponeurotic fibrosarcoma oncogene homolog B (MAFB); and platelet factor 4 (PF4); and b) using a computer, applying a classifier to said sample dataset to thereby classify said test subject into a class representing human subjects having mild osteoarthritis or a class representing human subjects not having osteoarthritis, wherein said classifier is able to discriminate between human subjects having mild osteoarthritis and human subjects not having osteoarthritis, wherein said classifier is derived from data representing a level of expression of each marker of said marker set in blood samples of human subjects having mild osteoarthritis and in blood samples of human subjects not having osteoarthritis, and wherein said computer is programmed to apply said classifier to a dataset representing a level of expression of each gene of said set of genes in a blood sample of a human individual to thereby classify said test individual into said class representing human subjects having mild osteoarthritis or said class representing human subjects not having osteoarthritis, thereby profiling gene expression in a human test subject.

8. The method of claim 7, wherein said classifier is based on a multiple regression equation.

9. The method of claim 7, wherein said classifier has a format:

$$SCORE=-1.839+0.8*HSP90AA1-1.5525*IKBKAP+1.10184*IL13RA1+0.78923*LAMC1-1.3974*MAFB+1.0602*PF4, \text{ where}$$

SCORE, if positive, classifies said test subject into said class representing human subjects having mild osteoarthritis;

SCORE, if negative, classifies said test subject into said class representing human subjects not having osteoarthritis;

HSP90AA1 represents said level of expression of heat shock protein 90 kDa alpha (cytosolic), class A member 1 (HSP90AA1) in said sample of said test subject;

IKBKAP represents said level of expression of inhibitor of kappa light polypeptide gene enhancer in B-cells, kinase complex-associated protein (IKBKAP) in said sample of said test subject;

IL13RA1 represents said level of expression of interleukin 13 receptor, alpha 1 (IL13RA1) in said sample of said test subject;

LAMC1 represents said level of expression of laminin, gamma 1 (LAMC1) in said sample of said test subject:

MAFB represents said level of expression of v-maf musculoaponeurotic fibrosarcoma oncogene homolog B (MAFB) in said sample of said test subject; and PF4 represents said level of expression of platelet factor 4 (PF4) in said sample of said test subject.

10. The method of claim 7, wherein said obtaining said sample dataset comprises measuring said level of expression of each gene of said set of genes in said blood sample of said test subject.

11. The method of claim 10, wherein said classifier is based on a multiple regression equation.

12. The method of claim 10, wherein said classifier has a format:

$$SCORE=-1.839+0.8*HSP90AA1-1.5525*IKBKAP+1.10184*IL13RA1+0.78923*LAMC1-1.3974*MAFB+1.0602*PF4, \text{ where}$$

SCORE, if positive, classifies said test subject into said class representing human subjects having mild osteoarthritis;

SCORE, if negative, classifies said test subject into said class representing human subjects not having osteoarthritis;

HSP90AA1 represents said level of expression of heat shock protein 90 kDa alpha (cytosolic), class A member 1 (HSP90AA1) in said sample of said test subject;

IKBKAP represents said level of expression of inhibitor of kappa light polypeptide gene enhancer in B-cells, kinase complex-associated protein (IKBKAP) in said sample of said test subject;

IL13RA1 represents said level of expression of interleukin 13 receptor, alpha 1 (IL13RA1) in said sample of said test subject;

LAMC1 represents said level of expression of laminin, gamma 1 (LAMC1) in said sample of said test subject;

MAFB represents said level of expression of v-maf musculoaponeurotic fibrosarcoma oncogene homolog B (MAFB) in said sample of said test subject; and PF4 represents said level of expression of platelet factor 4 (PF4) in said sample of said test subject.

13. A method for profiling gene expression in a human test subject, the method comprising:

using a computer, applying a classifier to a sample dataset representing a level of expression in a blood sample of said test subject of each gene of a set of genes consisting of heat shock protein 90 kDa alpha (cytosolic), class A member 1 (HSP90AA1); inhibitor of kappa light polypeptide gene enhancer in B-cells, kinase complex-associated protein (IKBKAP); interleukin 13 receptor, alpha 1 (IL13RA1); laminin, gamma 1 (LAMC1); v-maf musculoaponeurotic fibrosarcoma oncogene homolog B (MAFB); and platelet factor 4 (PF4), to thereby classify said test subject into a class representing human subjects having mild osteoarthritis or a class representing human subjects not having osteoarthritis, wherein said classifier is able to discriminate between human subjects having mild osteoarthritis and human subjects not having osteoarthritis, wherein said classifier is derived from data representing a level of expression of each marker of said marker set in blood samples of human subjects having mild osteoarthritis and in blood samples of human subjects not having osteoarthritis, and wherein said computer is programmed to apply said classifier to a dataset representing a level of expression of each gene of said set of genes in a blood sample of a human individual to thereby classify said human individual into said class representing human subjects having osteoarthritis or said class representing human subjects not having osteoarthritis, thereby profiling gene expression in a human test subject.

14. The method of claim 13, wherein said classifier is based on a multiple regression equation.

15. The method of claim 13, wherein said classifier has a format:

$$SCORE=-1.839+0.8*HSP90AA1-1.5525*IKBKAP+1.10184*IL13RA1+0.78923*LAMC1-1.3974*MAFB+1.0602*PF4, \text{ where}$$

SCORE, if positive, classifies said test subject into said class representing human subjects having mild osteoarthritis;

SCORE, if negative, classifies said test subject into said class representing human subjects not having osteoarthritis;

HSP90AA1 represents said level of expression of heat shock protein 90 kDa alpha (cytosolic), class A member 1 (HSP90AA1) in said sample of said test subject;

IKBKAP represents said level of expression of inhibitor of kappa light polypeptide gene enhancer in B-cells, kinase complex-associated protein (IKBKAP) in said sample of said test subject;

IL13RA1 represents said level of expression of interleukin 13 receptor, alpha 1 (IL13RA1) in said sample of said test subject;

LAMC1 represents said level of expression of laminin, gamma 1 (LAMC1) in said sample of said test subject;

MAFB represents said level of expression of v-maf musculoaponeurotic fibrosarcoma oncogene homolog B (MAFB) in said sample of said test subject; and PF4 represents said level of expression of platelet factor 4 (PF4) in said sample of said test subject.

16. The method of claim 13, further comprising obtaining said sample dataset by measuring said level of expression of each gene of said set of genes in said blood sample of said test subject, prior to applying said classifier to said sample dataset.

17. The method of claim 16, wherein said classifier is based on a multiple regression equation.

18. The method of claim 16, wherein said classifier has a format:

$$SCORE=-1.839+0.8*HSP90AA1-1.5525*IKBKAP+1.10184*IL13RA1+0.78923*LAMC1-1.3974*MAFB+1.0602*PF4, \text{ where}$$

SCORE, if positive, classifies said test subject into said class representing human subjects having mild osteoarthritis;

SCORE, if negative, classifies said test subject into said class representing human subjects not having osteoarthritis;

HSP90AA1 represents said level of expression of heat shock protein 90 kDa alpha (cytosolic), class A member 1 (HSP90AA1) in said sample of said test subject;

IKBKAP represents said level of expression of inhibitor of kappa light polypeptide gene enhancer in B-cells, kinase complex-associated protein (IKBKAP) in said sample of said test subject;

IL13RA1 represents said level of expression of interleukin 13 receptor, alpha 1 (IL13RA1) in said sample of said test subject;

LAMC1 represents said level of expression of laminin, gamma 1 (LAMC1) in said sample of said test subject;

MAFB represents said level of expression of v-maf musculoaponeurotic fibrosarcoma oncogene homolog B (MAFB) in said sample of said test subject; and PE4 represents said level of expression of platelet factor 4 (PF4) in said sample of said test subject.

* * * * *